United States Patent
Miyajima et al.

(10) Patent No.: US 12,128,072 B2
(45) Date of Patent: Oct. 29, 2024

(54) HEPATOCYTES AND HEPATIC NON-PARENCHYMAL CELLS, AND METHODS FOR PREPARATION THEREOF

(71) Applicant: The University of Tokyo, Tokyo (JP)

(72) Inventors: Atsushi Miyajima, Tokyo (JP); Taketomo Kido, Tokyo (JP); Yuta Koui, Tokyo (JP); Ayaka Kobayashi, Tokyo (JP)

(73) Assignee: The University of Tokyo, Tokyo (JP)

( * ) Notice: Subject to any disclaimer, the term of this patent is extended or adjusted under 35 U.S.C. 154(b) by 980 days.

(21) Appl. No.: 16/685,761

(22) Filed: Nov. 15, 2019

(65) Prior Publication Data
US 2020/0188444 A1    Jun. 18, 2020

Related U.S. Application Data

(63) Continuation of application No. 15/558,879, filed as application No. PCT/JP2016/058411 on Mar. 16, 2016, now abandoned.
(Continued)

(51) Int. Cl.
*A61K 35/407* (2015.01)
*C12N 5/077* (2010.01)
*G01N 33/50* (2006.01)

(52) U.S. Cl.
CPC .......... *A61K 35/407* (2013.01); *C12N 5/0652* (2013.01); *G01N 33/5014* (2013.01);
(Continued)

(58) Field of Classification Search
CPC ............. A61K 35/407; G01N 33/5067; G01N 33/5014; C12N 2506/14; C12N 5/0652;
(Continued)

(56) References Cited

U.S. PATENT DOCUMENTS

| | | |
|---|---|---|
| 2006/0154235 A1 | 7/2006 | Ochiya et al. |
| 2012/0009672 A1* | 1/2012 | Sancho-Bru ........... C12N 5/067 435/353 |

(Continued)

FOREIGN PATENT DOCUMENTS

| | | |
|---|---|---|
| EP | 1424391 A1 | 6/2004 |
| EP | 2671944 A1 | 12/2013 |

(Continued)

OTHER PUBLICATIONS

Motoyama "Cytoglobin is expressed in hepatic stellate cells, but not in myofibroblasts, in normal and fibrotic human liver" Laboratory Investigation 94, 192-207 PUB Dec. 2, 2013 (Year: 2013).*

(Continued)

*Primary Examiner* — Marcia S Noble
*Assistant Examiner* — Lauren K Van Buren
(74) *Attorney, Agent, or Firm* — Kilpatrick Townsend & Stockton LLP

(57) ABSTRACT

The present invention pertains to hepatocytes, liver progenitor cells, cholangiocytes, liver sinusoidal endothelial progenitor cells, liver sinusoidal endothelial cells, hepatic stellate progenitor cells, hepatic stellate cells, and liver cellular tissue models, as well as to methods for preparing these cells. The present invention also pertains to a cell fraction comprising liver progenitor cells, liver sinusoidal endothelial progenitor cells, or hepatic stellate progenitor cells. The present invention also pertains to a pharmaceutical composition or kit comprising the above-mentioned cells, a liver cellular tissue model, or a cell fraction. The present invention also pertains to: a method for screening liver disease treatment agents; a method for evaluating the hepatotoxicity of drugs, hepatocytes for infectious disease models, and a method for preparing the same; infectious disease model tissues and a method for preparing the same; as well as a (Continued)

method for screening infectious liver disease treatment agents.

4 Claims, 40 Drawing Sheets

Specification includes a Sequence Listing.

Related U.S. Application Data

(60) Provisional application No. 62/287,993, filed on Jan. 28, 2016, provisional application No. 62/134,899, filed on Mar. 18, 2015.

(52) U.S. Cl.
CPC ..... *G01N 33/5067* (2013.01); *C12N 2320/10* (2013.01); *C12N 2503/02* (2013.01); *C12N 2503/04* (2013.01); *C12N 2506/13* (2013.01); *C12N 2506/14* (2013.01); *Y02A 50/30* (2018.01)

(58) Field of Classification Search
CPC ............ C12N 2320/10; C12N 2503/02; C12N 2503/04; C12N 2506/13
See application file for complete search history.

(56) References Cited

U.S. PATENT DOCUMENTS

| | | | | |
|---|---|---|---|---|
| 2014/0243227 | A1* | 8/2014 | Clevers | A61P 3/10 506/10 |
| 2018/0147242 | A1 | 5/2018 | Miyajima et al. | |

FOREIGN PATENT DOCUMENTS

| | | |
|---|---|---|
| JP | 2006-254896 A | 9/2006 |
| WO | 2007/140243 A2 | 12/2007 |
| WO | 2011/154552 A1 | 12/2011 |
| WO | 2011/158125 A2 | 12/2011 |
| WO | 2016/148216 A1 | 9/2016 |

OTHER PUBLICATIONS

Yu et al. "Hepatic Stellate Cells Secreted Hepatocyte Growth Factor Contributes to the Chemoresistance of Hepatocellular Carcinoma" Sep. 2013, vol. 8, Issue 9 (Year: 2013).*
Suskind et al. "Searching for common stem cells of hepatic and hematopoietic systems in the human fetal liver" CD34 cytokeratin 7/8 express markers for stellate cells Journal of Hepatology 40 (2004), 261-268 (Year: 2004).*
Blaner "Hepatic stellate cell lipid droplets: A specialized lipid droplet for retinoid storage" Biochimica et Biophysica Acta 1791, (2009), 467-473 (Year: 2009).*
Asahina et al., "Mesenchymal Origin of Hepatic Stellate Cells, Submesothelial Cells, and Perivascular Mesenchymal Cells During Mouse Liver Development," Hepatology, 2009, vol. 49, No. 3, pp. 998-1011.
Asahina, Kinji: "Hepatic stellate cell progenitor cells," Journal of Gastroenterology and Hepatology, vol. 27, No. Suppl. 2, Sp. Iss. SI, Mar. 2012, pp. 80-84, pp. 1440-1746.
European Application No. 16765045.6, Extended European Search Report mailed Aug. 14, 2018, 9 pages.
Hristov et al., "Endothelial Progenitor Cells. Mobilization, Differentiation, and Homing," Arterioscler Thromb Vasc Biol., 2003, vol. 23, pp. 1185-1189.
Ikeda et al., "Involvement of Rho/Rho kinase pathway in regulation of apoptosis in rat hepatic stellate cells," Am J Physiol Gastrointest Liver Physiol., 2003, vol. 285, pp. G880-G886.
International Application No. PCT/JP2016/058411, International Search Report mailed Jun. 21, 2016, 12 pages.
Ishida, Seiichi, "Development of Hepatocyte Co-culture System with Liver Nonparenchymal Cells," Advances in Pharmaceuticals Sciences Kenkyu Seika Hokokushu, Mar. 1, 2013, vol. 29, pp. 51-54.
Kordes et al., "CD133+ hepatic stellate cells are progenitor cells", Biochemical and Biophysical Research Communications, vol. 352, No. 2, 2007, pp. 410-417.
Mousavi et al., "Receptor-Mediated Endocytosis of Immune Complexes in Rat Liver Sinusoidal Endothelial Cells Is Mediated by FγRIIb2," Hepatology, Sep. 2007, vol. 46, No. 3, pp. 871-884.
Murata et al., "Inhibitory effect of Y-27632, a ROCK inhibitor, on progression of rat liver fibrosis in association with inactivation of hepatic stellate cells", Journal of Hepatology, vol. 35, No. 4, Oct. 1, 2001, pp. 474-481.
Ogawa et al., "Three-dimensional culture and cAMP signaling promote the maturation of human pluripotent stem cell-derived hepatocytes," Development, 2013, vol. 140 (15), pp. 3285-3296.
Si-Tayeb et al., "Highly Efficient Generation of Human Hepatocyte-like Cells from Induced Pluripotent Stem Cells," Hepatology, 2010, 51(1), pp. 297-305.
Suzuki et al., "p75 Neurotrophin Receptor Is a Marker for Precursors of Stellate Cells and Portal Fibroblasts in Mouse Fetal Liver," Gastroenterology, Jul. 1, 2008, vol. 135, No. 1, pp. 270-281.
Taguchi et al., "Redefining the In Vivo Origin of Metanephric Nephron Progenitors Enables Generation of Complex Kidney Structures from Pluripotent Stem Cells," Cell Stem Cell, 2014, 14(1), pp. 53-67.
Takayama et al., "Generation of metabolically functioning hepatocytes from human pluripotent stem cells by FOXA2 and HNF1α transduction," Journal of Hepatology, 2012, vol. 57, pp. 628-636.
Van Beuge et al., "Reduction of Fibrogenesis by Selective Delivery of a Rho Kinase Inhibitor to Hepatic Stellate Cells in Mice," The Journal of Pharmacology and Experimental Therapeutics, vol. 337, No. 3, Jun. 2011, pp. 628-635.
Wang et al., "Differentiation of human induced pluripotent stem cells to mature functional Purkinje neurons," Sci. Rep., 2015, 5: 9232, DOI: 10.1038/srep09232.
Wang et al., "Liver sinusoidal endothelial cell progenitor cells promote liver regeneration in rats," The Journal of Clinical Investigation, 2012, vol. 122, No. 4, pp. 1567-1573.
Yin et al., "Hepatic stellate cells in liver development, regeneration, and cancer," The Journal of Clinical Investigation, vol. 123, No. 5, May 2013, pp. 1902-1910.
Yoshida et al., "Involvement of signaling of VEGF and TGF-β in differentiation of sinusoidal endothelial cells during culture of fetal rat liver cells," Cell Tissue Res, 2007, vol. 329, pp. 273-282.

* cited by examiner

FIG. 5
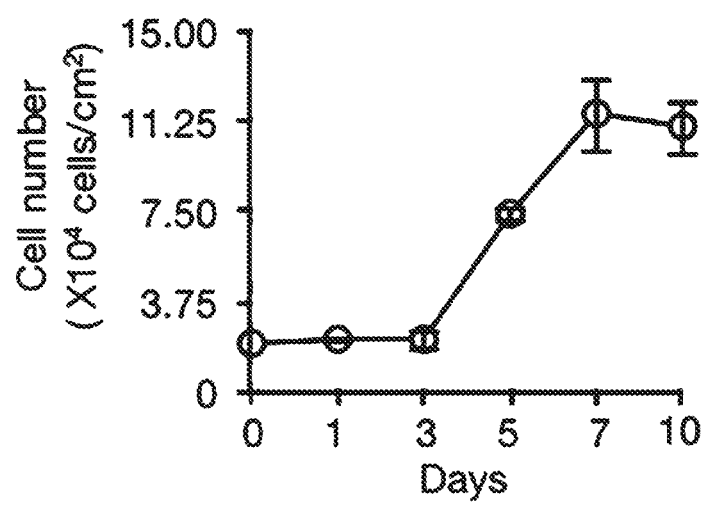
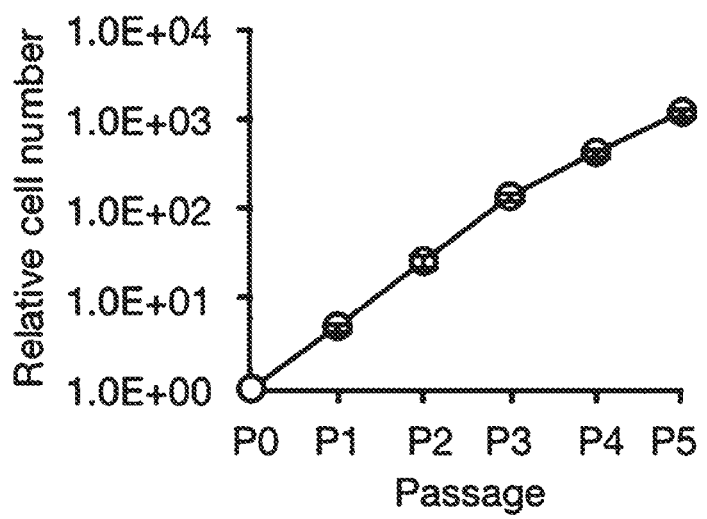

FIG. 12
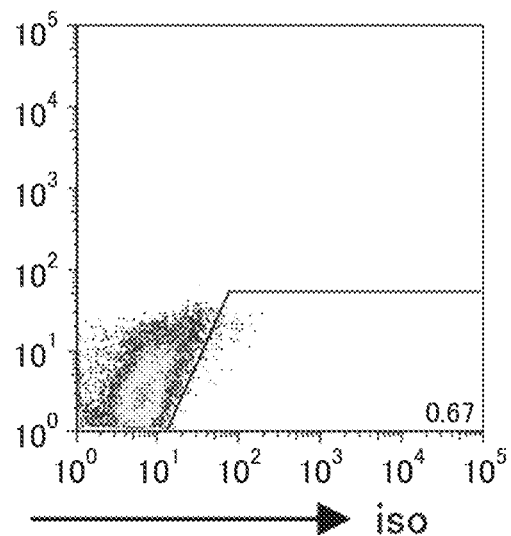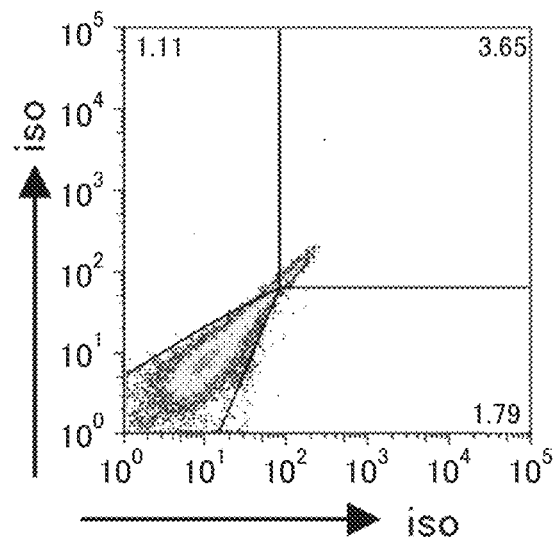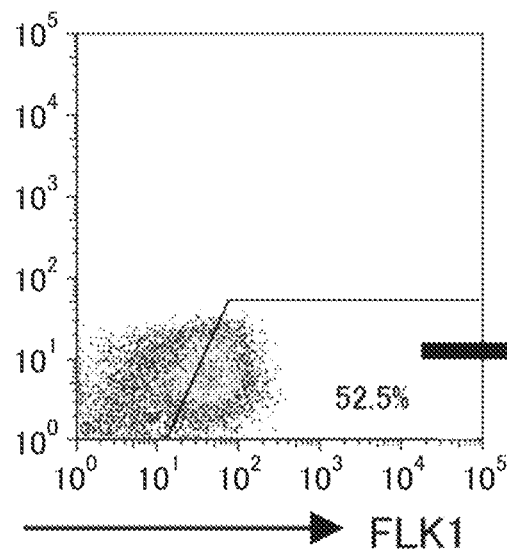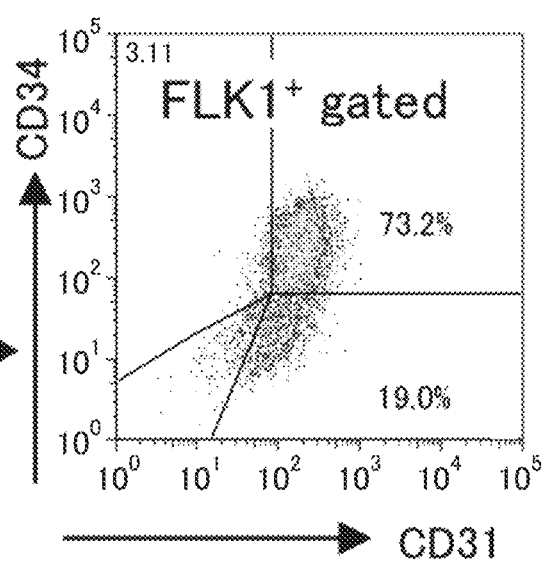

FIG. 23
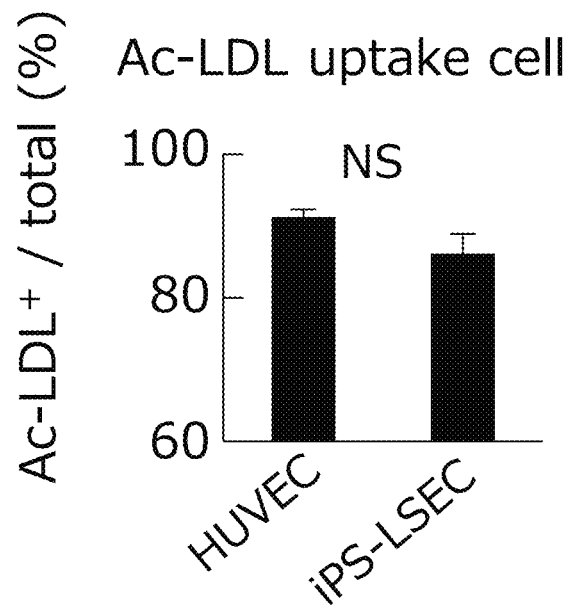
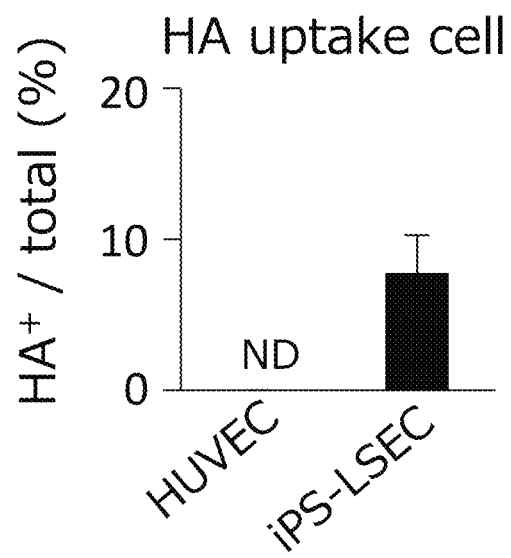

FIG. 24
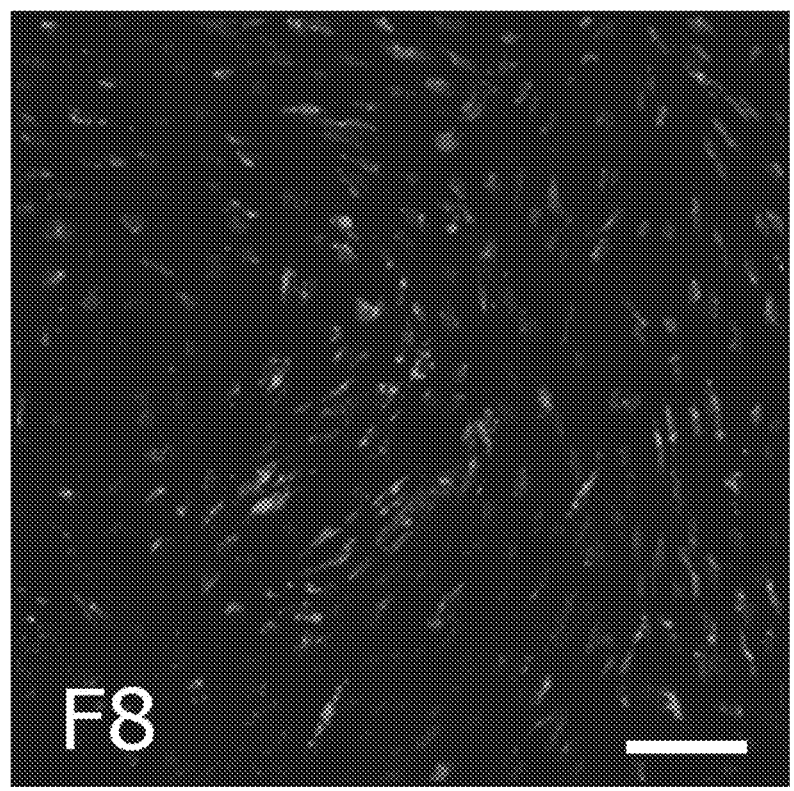
FIG. 25
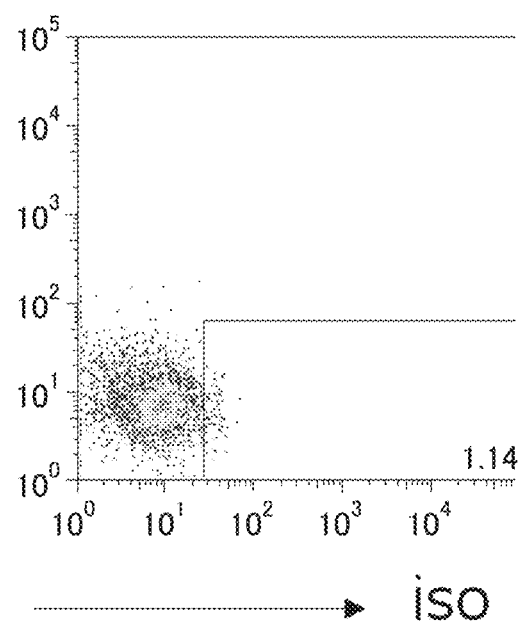
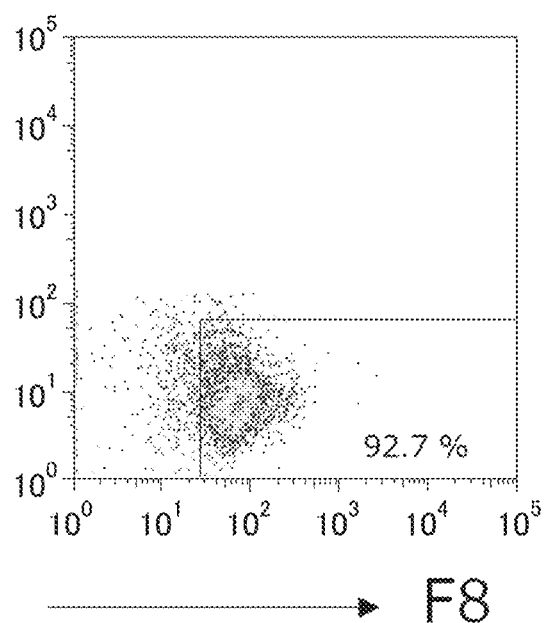

FIG. 26
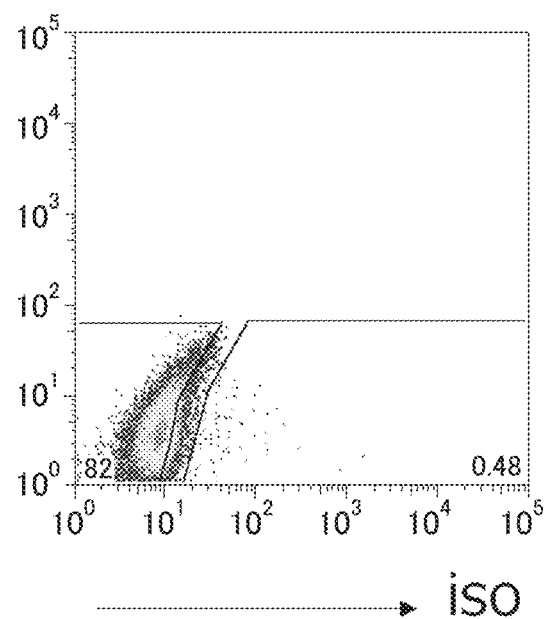
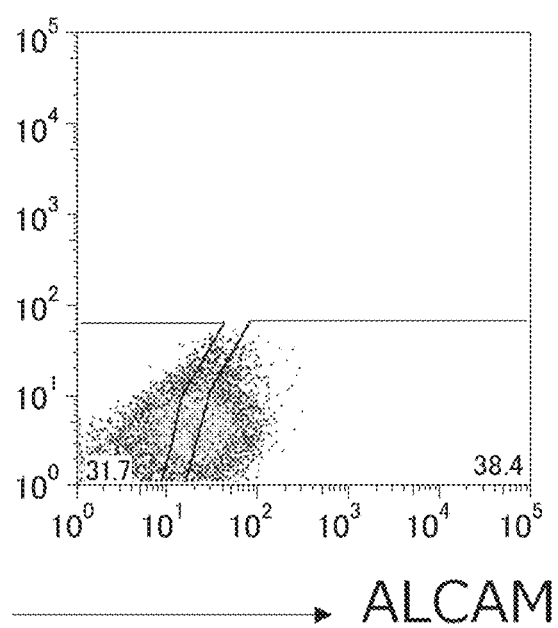

HEPATOCYTES AND HEPATIC NON-PARENCHYMAL CELLS, AND METHODS FOR PREPARATION THEREOF

CROSS-REFERENCE TO RELATED APPLICATIONS

The current application is a continuation of U.S. patent application Ser. No. 15/558,879 filed Sep. 15, 2017, pending, which is a National Phase entry of International Application No. PCT/JP2016/058411, filed Mar. 16, 2016, which claims priority to U.S. Provisional Pat. Appl. No. 62/287,933, filed Jan. 28, 2016 and U.S. Provisional Pat. Appl. No. 62/134,899 filed Mar. 18, 2015, the disclosures of which are hereby incorporated by reference in their entireties for all purposes.

REFERENCE TO A "SEQUENCE LISTING"

The Sequence Listing written in file SequenceListing_093803-004010US-1166953.txt created on Nov. 15, 2019, 19,734 bytes, machine format IBM-PC, MS-Windows operating system, is hereby incorporated by reference in its entirety for all purposes.

TECHNICAL FIELD

The present invention relates to hepatocytes, liver progenitor cells, cholangiocytes, liver sinusoidal endothelial progenitor cells, liver sinusoidal endothelial cells, hepatic stellate progenitor cells, hepatic stellate cells and liver cellular tissue models, as well as to methods for preparation of the same. The invention further relates to a cell fraction that comprises liver progenitor cells, liver sinusoidal endothelial progenitor cells or hepatic stellate progenitor cells. The invention still further relates to a pharmaceutical composition or kit that comprises the aforementioned cells, liver cellular tissue model or cell fraction. The invention yet further relates to a method for screening liver disease treatment agents, to a method of evaluating hepatotoxicity of drugs, to hepatocytes for infectious liver disease models and a method for preparing them, to infectious liver disease model tissue and a method of preparing it, and to a method for screening infectious liver disease treatment agents.

BACKGROUND ART

The liver is an organ that performs a wide variety of functions including metabolism, detoxification and serum protein synthesis, and is essential for maintaining biological homeostasis. Hepatic parenchymal cells (hepatocytes), as the parenchymal cells in the liver, carry out these multiple liver functions. Because they express a large number of metabolic enzymes such as the cytochrome P450 (CYP) enzyme group, hepatocytes are utilized in innovative drug development and research including drug toxicity testing.

In addition, liver transplant is the only means of complete treatment of serious liver diseases (such as fulminant hepatitis, hepatic cirrhosis and hepatic cancer) and the like, but it is associated with problems such as a lack of donors and the need for lifelong immunosuppression treatment, and therefore development of new methods of treatment as alternatives to liver transplant is desired. One of these alternatives is cell transplantation therapy.

However, hepatocytes that have been isolated from live liver tissue rapidly lose their metabolic enzyme activity when cultured. Moreover, it is difficult to provide human hepatocytes in large quantities from human organs.

Recent years have seen rising expectations for human pluripotent stem cells that include human Embryonic Stem cells (ES cells) and induced Pluripotent Stem cells (iPS cells) as new hepatocyte sources. Numerous attempts to induce hepatocytes from pluripotent stem cells have been reported (NPLs 1 to 3).

Hepatocytes exist in a condition of close contact with Liver Sinusoidal Endothelial Cells (LSEC) that form sinusoids as the capillaries of the liver, and Hepatic Stellate Cells (HSC) that are pericytes. These hepatic non-parenchymal cells are known to contribute significantly to development and differentiation of the liver by interaction with hepatocytes.

In recent research on inducing differentiation utilizing stem cells, there has been increasing interest in regeneration of tissue, with focus on the interaction between cells, instead of merely inducing cells of a single function. Most organs in the body are not composed of a single cell type, but instead different types of cells develop and differentiate via interaction of humoral factors, cell adhesion and the like. Successful regeneration of functional cells and tissue has been reported, by forming a three-dimensional structure by co-culturing cells of different types induced from stem cells (NPLs 4 and 5).

CITATION LIST

Non-Patent Literature

[NPL 1] Ogawa et al., Development 2013, 140(15), 3285-3296
[NPL 2] Si-Tayeb et al., Hepatology 2010, 51(1), 297-305
[NPL 3] Takayama et al., J Hepatol. 2012, 57(3), 628-36
[NPL 4] Wang et al., Sci Rep., 2015, 5, 9232
[NPL 5] Taguchi et al., Cell Stem Cell, 2014, 14(1), 53-67

SUMMARY OF INVENTION

Technical Problem

The conventionally known methods of inducing human hepatocytes from human pluripotent stem cells have required multistage differentiation inducement, and it has been difficult to prepare large homogeneous volumes of hepatocytes in short periods. Moreover, it is currently the case that with human hepatocytes obtained by such methods, the expression level of CYP, an enzyme involved in drug metabolism, is lower than hepatocytes taken directly from the body, and at the current time, inducement of hepatocytes with physiological function equivalent to hepatocytes taken directly from the body has yet to be achieved.

Moreover, it is believed that it will be possible to induce functional hepatocytes and liver tissue by faithfully reproducing in vitro the intercellular interaction that takes place during liver development. However, it is difficult to obtain non-parenchymal cells that interact with hepatocytes during liver development, in a stable manner and in large quantities from the human body.

It is therefore an object of the present invention to provide a method of preparing homogeneous highly functional hepatocytes, hepatic non-parenchymal cells and their precursor cells at high purity and in an efficient manner.

Solution to Problem

As a result of diligent research in light of these problems, the present inventors have found that it is possible to selectively separate off liver progenitor cells from a cell fraction that comprises liver progenitor cells, by using the carboxypeptidase M (CPM)-positive phenotype as the marker, and to prepare homogeneous, highly functional hepatocytes by inducing differentiation of the obtained liver progenitor cells.

The present inventors also found that it is possible to prepare homogeneous, highly functional liver sinusoidal endothelial cells by selectively separating off homogeneous, highly functional liver sinusoidal endothelial progenitor cells from a cell fraction that comprises liver sinusoidal endothelial progenitor cells, using the FLK1-positive, CD34-positive and CD31-positive phenotype as the marker, and inducing differentiation of the obtained liver sinusoidal endothelial progenitor cells.

The present inventors still further found that it is possible to selectively separate off homogeneous, highly functional hepatic stellate progenitor cells from a cell fraction that comprises hepatic stellate progenitor cells, by using the activated leukocyte cell adhesion molecule (ALCAM)-positive phenotype as the marker.

The present inventors still further found that it is possible to induce differentiation of hepatic stellate progenitor cells to hepatic stellate cells by using a Rho kinase (Rho-associated protein kinase: ROCK) inhibitor.

The present inventors still further found that it is possible to promote differentiation of liver progenitor cells to hepatocytes by co-culturing the obtained liver progenitor cells mentioned above with hepatic non-parenchymal cells.

The present inventors still further found that it is possible to prepare hepatocytes for an infectious liver disease model from the obtained liver progenitor cells and hepatocytes mentioned above.

Specifically, the invention has the following aspects.

[1]
A method of preparing liver progenitor cells, comprising a step of separating off liver progenitor cells from a cell fraction that comprises liver progenitor cells, by using the CPM-positive phenotype as the marker.

[2]
The method according to [1], further comprising a step of inducing differentiation of embryonic endoderm cells or hepatic endoderm cells to prepare a cell fraction that comprises liver progenitor cells.

[3]
The method according to [1], further comprising a step of inducing differentiation of pluripotent stem cells to prepare the embryonic endoderm cells or hepatic endoderm cells.

[4]
The method according to [2] or [3], wherein the pluripotent stem cells are human iPS cells.

[5]
Liver progenitor cells that can be prepared by the method according to any one of [1] to [4], having the CPM-positive phenotype, having proliferation potency, and having differentiation potency to hepatocytes or cholangiocytes.

[6]
Liver progenitor cells according to [5], wherein the proliferation potency of the liver progenitor cells after cryopreservation and thawing does not decrease compared to the proliferation potency of the liver progenitor cells before cryopreservation.

[7]
A cell fraction that comprises liver progenitor cells at 90% or greater with respect to the total cells, wherein the liver progenitor cells have the CPM-positive phenotype, have proliferation potency, and have differentiation potency to hepatocytes or cholangiocytes.

[8]
A method of preparing hepatocytes, comprising a step of inducing differentiation of liver progenitor cells according to [5] or [6] to hepatocytes.

[9]
Hepatocytes having proliferation potency, that can be prepared by the method according to [8].

[10]
A method of preparing cholangiocytes, comprising a step of inducing differentiation of liver progenitor cells according to [5] or [6] to cholangiocytes.

[11]
Cholangiocytes having proliferation potency, that can be prepared by the method according to [10].

[12]
A method of preparing liver sinusoidal endothelial progenitor cells, comprising a step of separating off liver sinusoidal endothelial progenitor cells from a cell fraction that comprises liver sinusoidal endothelial progenitor cells, using the FLK1-positive, CD34-positive and CD31-positive phenotype as the marker.

[13]
The method according to [12], further comprising a step of inducing differentiation of mesodermal cells to prepare a cell fraction that comprises liver sinusoidal endothelial progenitor cells.

[14]
The method according to [13], further comprising a step of inducing differentiation of pluripotent stem cells to prepare the mesodermal cells.

[15]
The method according to [14], wherein the pluripotent stem cells are human iPS cells.

[16]
Liver sinusoidal endothelial progenitor cells that can be prepared by the method according to any one of [12] to [15], having the FLK1-positive, CD34-positive and CD31-positive phenotype, having proliferation potency, and having differentiation potency to liver sinusoidal endothelial cells.

[17]
A cell fraction that comprises liver sinusoidal endothelial progenitor cells at 90% or greater with respect to the total cells, wherein the liver sinusoidal endothelial progenitor cells have the FLK1-positive, CD34-positive and CD31-positive phenotype, have proliferation potency, and have differentiation potency to liver sinusoidal endothelial cells.

[18]
A method of preparing liver sinusoidal endothelial cells, comprising the steps of:
 (1) inducing differentiation of liver sinusoidal endothelial progenitor cells according to [16] using a TGF-β inhibitor to prepare a cell fraction that comprises liver sinusoidal endothelial cells, and
 (2) separating off liver sinusoidal endothelial cells from a cell fraction that comprises liver sinusoidal endothelial cells, using the CD31-positive and FcγR II-positive phenotype as the marker.

[19]
Liver sinusoidal endothelial cells that can be prepared by the method according to [18], having the CD31-positive and FcγR II-positive phenotype, and having proliferation potency.

[20]
A method of preparing hepatic stellate progenitor cells, comprising a step of separating off hepatic stellate progenitor cells from a cell fraction that comprises hepatic stellate progenitor cells, using the ALCAM-positive phenotype as the marker.

[21]

A method of preparing hepatic stellate progenitor cells, further comprising a step of inducing differentiation of pluripotent stem cells to prepare a cell fraction that comprises hepatic stellate progenitor cells.

[22]

The method according to [21], wherein the pluripotent stem cells are human iPS cells.

[23]

Hepatic stellate progenitor cells that can be prepared by the method according to any one of [20] to [22], having the ALCAM-positive phenotype, having proliferation potency, and having differentiation potency to hepatic stellate cells.

[24]

A cell fraction that comprises hepatic stellate progenitor cells at 90% or greater with respect to the total cells, wherein the hepatic stellate progenitor cells have the ALCAM-positive phenotype, have proliferation potency, and have differentiation potency to hepatic stellate cells.

[25]

A method of preparing hepatic stellate cells, comprising a step of inducing differentiation of hepatic stellate progenitor cells to hepatic stellate cells using ROCK inhibitor.

[26]

The method according to [25], wherein the hepatic stellate progenitor cells are hepatic stellate progenitor cells according to [23].

[27]

Hepatic stellate cells having proliferation potency, that can be prepared by the method according to [25] or [26].

[28]

A method of preparing a liver cellular tissue model, comprising a step of co-culturing liver progenitor cells according to [5] or [6] with at least one type of hepatic non-parenchymal cells selected from the group consisting of liver sinusoidal endothelial cells, hepatic stellate cells and liver mesothelial cells.

[29]

The method according to [28], wherein the liver sinusoidal endothelial cells are liver sinusoidal endothelial cells according to [19].

[30]

The method according to [28] or [29], wherein the hepatic stellate cells are hepatic stellate cells according to [27].

[31]

A liver cellular tissue model comprising hepatocytes, and at least one type of hepatic non-parenchymal cells selected from the group consisting of liver sinusoidal endothelial cells, hepatic stellate cells and liver mesothelial cells, that can be prepared by a method according to any one of [28] to [30]. [32]

A pharmaceutical composition comprising liver progenitor cells according to [5] or [6], a cell fraction according to [7], hepatocytes according to [9], cholangiocytes according to [11], liver sinusoidal endothelial progenitor cells according to [16], a cell fraction according to [17], liver sinusoidal endothelial cells according to [19], hepatic stellate progenitor cells according to [23], a cell fraction according to [24], hepatic stellate cells according to [27], or a liver cellular tissue model according to [31].

[33]

A method for screening liver disease treatment agents, comprising administering a candidate liver disease treatment agent to hepatocytes according to [9] or a liver cellular tissue model according to [31].

[34]

A method of evaluating hepatotoxicity of a drug, comprising administering a drug to hepatocytes according to [9] or a liver cellular tissue model according to [31].

[35]

A method of preparing hepatocytes for an infectious disease model, comprising the steps of:
(1) infecting liver progenitor cells according to [5] or [6] or liver progenitor cells in a cell fraction according to [7] with a pathogen, and
(2) inducing differentiation of the liver progenitor cells that have been infected with the pathogen to prepare hepatocytes for a pathogen-infectious disease model.

[36]

A method of preparing hepatocytes for an infectious disease model, comprising a step of infecting hepatocytes according to [9] with a pathogen.

[37]

The method according to [35] or [36], wherein the pathogen is a hepatitis virus or malaria protozoan.

[38]

Hepatocytes for an infectious disease model that can be prepared by the method according to [35] to [37].

[39]

A method of preparing infectious disease model tissue, comprising the steps of:
(1) infecting liver progenitor cells according to [5] or [6] or liver progenitor cells in a cell fraction according to [7] with a pathogen, and
(2) co-culturing the pathogen-infected liver progenitor cells with at least one type of hepatic non-parenchymal cells selected from the group consisting of liver sinusoidal endothelial cells, hepatic stellate cells and liver mesothelial cells.

[40]

The method according to [39], wherein the pathogen is a hepatitis virus or malaria protozoan.

[41]

An infectious disease model tissue that can be prepared by the method according to [39] or [40].

[42]

A method for screening infectious liver disease treatment agents, comprising administering a candidate infectious liver disease treatment agent to hepatocytes for an infectious disease model according to [38] or an infectious disease model tissue according to [41].

[43]

A kit comprising liver progenitor cells according to [5] or [6], a cell fraction according to [7], hepatocytes according to [9], cholangiocytes according to [11], liver sinusoidal endothelial progenitor cells according to [16], a cell fraction according to [17], liver sinusoidal endothelial cells according to [19], hepatic stellate progenitor cells according to [23], a cell fraction according to [24], hepatic stellate cells according to [27], or a liver cellular tissue model according to [31].

Advantageous Effects of Invention

According to the invention it is possible to prepare homogeneous, highly functional hepatocytes, hepatic non-parenchymal cells and their precursor cells at high purity and in an efficient manner. The obtained hepatocytes can be utilized for innovative drug screening, for example. Also, the obtained hepatocytes, hepatic non-parenchymal cells and their precursor cells can be used for cell therapy, for example. The obtained hepatocytes, hepatic non-parenchymal cells and their precursor cells can also be used to prepare disease models.

BRIEF DESCRIPTION OF DRAWINGS

FIG. 5 shows proliferation potency of CPM-positive cells (top), and relative cell counts after several subculturings of CPM-positive cells (bottom). The error bars indicate mean±SEM for four independent experiments.

FIG. 12 shows the results of flow cytometry analysis of cell groups comprising human liver sinusoidal endothelial progenitor cells obtained by inducing differentiation of human mesodermal cells. $CD31^+CD34^{+/-}$ cells (right) are present in the $FLK1^+$ cell fraction (left).

FIG. 23 shows the proportions of cells taking up acetylated LDL (Ac-LDL) and hyaluronic acid (HA), among the human iPS cell-derived CD31-positive, FcRγII-positive liver sinusoidal endothelial cells (iPS-LSEC). HUVEC were used as a control. n=3. mean±SEM. NS: No significant difference. ND: Not detected.

FIG. 24 shows an immunocytochemical staining image of human iPS cell-derived CD31-positive, FcRγII-positive liver sinusoidal endothelial cells. Blue: nuclei, red: factor VIII (F8).

FIG. 25 shows the results of flow cytometry analysis of an intracellular protein (factor VIII: F8) of human iPS cell-derived CD31-positive, FcRγII-positive liver sinusoidal endothelial cells.

FIG. 26 shows the results of flow cytometry analysis of human iPS cell-derived mesodermal cells.

DESCRIPTION OF EMBODIMENTS

Figure 1:
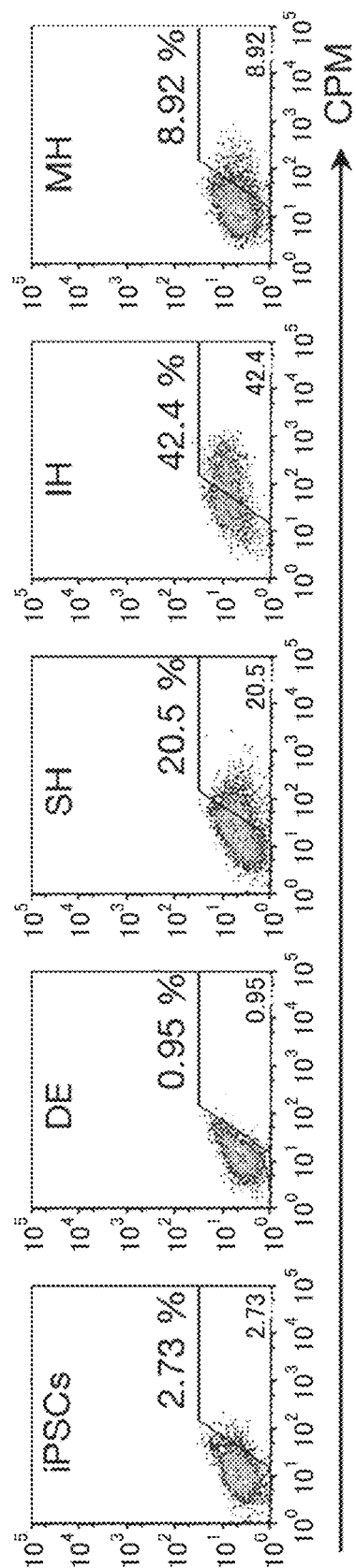
FIG. 1 shows the results of flow cytometry analysis indicating the time-dependent change in the CPM-positive cell fraction after inducing differentiation from human iPS cells to hepatocytes. In the graphs, "iPSCs" stands for "human iPS cells". "DE" (definitive endoderm) represents a cell group comprising embryonic endoderm cells. "SH" (specified hepatic) represents a cell group comprising hepatic endoderm cells. "IH" (immature hepatocytes) represents a cell group comprising liver progenitor cells. "MH" represents a cell group comprising mature hepatocytes. The percentages in the graphs indicate the percentages of CPM-positive cells in the cell groups.

Throughout the present specification, "hepatocytes" refers to hepatic parenchymal cells that perform the major functions of the liver including production of bile and metabolism of various substances. Hepatocytes express the drug metabolizing enzyme CYP. Hepatocytes also have albumin-producing ability and glycogen-storage capacity.

Throughout the present specification, the term "hepatic non-parenchymal cells" refers to another cell group other than hepatic parenchymal cells (hepatocytes) composing the liver, and it includes liver sinusoidal endothelial cells, hepatic stellate cells, mesothelial cells, cholangiocytes, pit cells and Kupffer cells.

Throughout the present specification, the term "pluripotent stem cells" refers to cells with self-renewal ability and pluripotency, the cells having the ability to form different types of cells composing the body. The term "self-renewal ability" means the ability to produce identical undifferentiated cells from a single cell. The term "differentiation potency" means the ability for a cell to differentiate. Examples of pluripotent stem cells include embryonic stem cells (ES cells), Muse cells (Multi-lineage differentiating Stress Enduring cells), germline stem cells (GS cells), embryonic germ cells (EG cells) and induced pluripotent stem cells (iPS cells), with no limitation to these. Pluripotent stem cells may be from a mammal, bird, fish, reptile or amphibian, with no particular limitations. Mammals include primates (humans, monkeys, etc.), rodents (mice, rats, guinea pigs, etc.), cats, dogs, rabbits, sheep, pigs, cows, horses, donkeys, goats and ferrets.

Throughout the present specification, the term "embryonic endoderm cells" refers to cells of the blastoderm that govern formation of organs of the entire intestinal tract including the esophagus, stomach, small intestine and large intestine, as well as organs derived from the intestinal tract including the lungs, thymus, parathyroid gland, thyroid gland, gallbladder and pancreas. Moreover, throughout the present specification, the term "hepatic endoderm cells" refers to cells differentiated from embryonic endoderm cells, i.e. cells having differentiation potency to liver progenitor cells. Throughout the present specification, the terms "embryonic endoderm cells" and "liver progenitor cells" include not only those present in the body but also those obtained by differentiation from pluripotent stem cells.

Throughout the present specification, the term "mesodermal cells" refers to cells of the blastoderm that govern formation of the mesothelium, muscles, skeleton, skin dermis, connective tissue, heart, blood vessels (including the vascular endothelium), blood (including blood cells), lymphatic vessels, spleen, kidneys, ureter and gonads (testes, uterus, gonadal epithelium). Throughout the present specification, the term "mesodermal cells" includes not only those present in the body but also those obtained by differentiation from pluripotent stem cells.

Throughout the present specification, the term "liver progenitor cells" refers to cells derived from embryonic endoderm cells, and having self-renewal ability and differentiation potency to hepatocytes or cholangiocytes. Throughout the present specification, the term "liver progenitor cells" includes not only those present in the body but also those obtained by differentiation from pluripotent stem cells.

Throughout the present specification, the term "liver sinusoidal endothelial progenitor cells" refers to cells derived from mesodermal cells, and having self-renewal ability and differentiation potency to liver sinusoidal endothelial cells. Throughout the present specification, the term "liver sinusoidal endothelial progenitor cells" includes not only those present in the body but also those obtained by differentiation from pluripotent stem cells.

Throughout the present specification, the term "hepatic stellate progenitor cells" refers to cells derived from mesodermal cells, and having self-renewal ability and differentiation potency to hepatic stellate cells. Throughout the present specification, the term "hepatic stellate progenitor cells" includes not only those present in the body but also those obtained by differentiation from pluripotent stem cells.

Throughout the present specification, the term "proliferation potency" means the ability of cells to proliferate. Unless otherwise specified, the state of proliferation referred to herein is the potential to proliferate at steady state. The term "steady state" means ordinary conditions in the body, i.e. a state in which biological homeostasis is maintained. Such a state can be easily determined by a person skilled in the art. For example, analysis of cell density allows confirmation based on whether the cell density is essentially constant and unchanging, or on whether cell proliferation marker expression is found. Throughout the present specification, "high proliferation potency" means having proliferation potency at steady state.

Throughout the present specification, the term "cell fraction" refers to the cell group that comprises a fixed amount of cells to be separated, isolated or concentrated. The cell fraction may comprise cells other than the cells to be separated, isolated or concentrated, and/or one or more chemical substances. The form of the cell fraction is not particularly restricted, and for example, it may be a cell-containing liquid, the liquid optionally being frozen.

One aspect of the invention relates to a method of preparing liver progenitor cells that comprises a step of separating off liver progenitor cells from a cell fraction that comprises liver progenitor cells, by using the CPM-positive phenotype as the marker. This will hereunder also be referred to as "method of preparing liver progenitor cells of the invention".

The "cell fraction that comprises liver progenitor cells" to be used in the "method of preparing liver progenitor cells of the invention" is not particularly restricted, and it may be prepared from a starting material consisting of any desired cells that differentiate to liver progenitor cells. For example, it may be prepared by inducing differentiation of embryonic endoderm cells or hepatic endoderm cells. The cell fraction may also be prepared by extraction from a living body. For example, it may be prepared from an animal embryo liver. According to one embodiment of the method of preparing liver progenitor cells of the invention, the preparation method further comprises a step of preparing a cell fraction that comprises liver progenitor cells.

When the "cell fraction that comprises liver progenitor cells" to be used in the "method of preparing liver progenitor cells of the invention" is to be prepared by inducing differentiation of embryonic endoderm cells or hepatic endoderm cells, the embryonic endoderm cells or hepatic endoderm cells may be prepared by extraction from a living body, or they may be prepared by inducing differentiation of pluripotent stem cells. When the preparation is to be by inducing differentiation of pluripotent stem cells, the pluripotent stem cells used are not particularly restricted, but are preferably mammalian pluripotent stem cells, more preferably pluripotent stem cells of a primate (human, monkey, etc.), rodent (mouse, rat, guinea pig, etc.), cat, canine, rabbit, sheep, pig, cow, horse, donkey, goat or ferret, even more preferably human pluripotent stem cells, and most preferably human iPS cells.

Differentiation inducement from pluripotent stem cells to liver progenitor cells via embryonic endoderm cells and hepatic endoderm cells may employ any publicly known method, with no particular restrictions. For example, it may be carried out by the same procedure as for inducing differentiation of human liver progenitor cells from human iPS cells, as described in NPL 2 (Si-Tayeb et al., Hepatology 2010, 51(1), 297-305).

Carboxypeptidase M (CPM) is a member of the carboxypeptidase family. CPM is expressed on cell membrane surfaces, and it cleaves arginine and lysine residues from the C-terminus of a peptide or protein. Surprisingly, it has been found that CPM is a liver progenitor cell-specific marker molecule. CPM is highly expressed in liver progenitor cells, but is not expressed in undifferentiated pluripotent stem cells and differentiated hepatocytes or cholangiocytes. Conventionally, α-fetoprotein (AFP) and HNF4a have been known as liver progenitor cell-specific markers. However, these are intracellular factors, and when such markers are used as indicators it is not possible to collect the liver progenitor cells without lysing the cells. CPM, on the other hand, is a membrane protein, and it can be collected as a marker without lysing the liver progenitor cells.

The step of separating off liver progenitor cells by using the CPM-positive phenotype as the marker is not particularly restricted, and for example, it may be carried out by Fluorescence Activated Cell Sorting (FACS) or Magnetic Cell Sorting (MACS).

According to one embodiment of the "method of preparing liver progenitor cells of the invention", the preparation method may further comprise a step of proliferating the separated liver progenitor cells. The conditions of cell culturing in the proliferation step are not particularly restricted so long as they do not inhibit proliferation of the liver progenitor cells.

One aspect of the invention relates to a method of isolating liver progenitor cells that comprises a step of separating off liver progenitor cells from a cell fraction that comprises liver progenitor cells, by using the CPM-positive phenotype as the marker. Another aspect of the invention relates to a method of concentrating liver progenitor cells that comprises a step of separating off liver progenitor cells from a cell fraction that comprises liver progenitor cells, by using the CPM-positive phenotype as the marker.

One aspect of the invention relates to liver progenitor cells that can be prepared by the method of preparing liver progenitor cells of the invention, having the CPM-positive phenotype, having proliferation potency and having differentiation potency to liver cells or cholangiocytes. This will hereunder also be referred to as "liver progenitor cells of the invention".

The "liver progenitor cells of the invention" may be cryopreserved. The proliferation potency of the liver progenitor cells of the invention after freezing and thawing does not decline compared to the proliferation potency of the liver progenitor cells of the invention before cryopreservation. The "liver progenitor cells of the invention" may be preserved, for example, at −80° C., for 3 months or longer, 6 months or longer, 9 months or longer or 12 months or longer. The high proliferation potency and cryopreservability of the liver progenitor cells of the invention allows culturing of the liver progenitor cells by thawing as necessary.

The "liver progenitor cells of the invention" may be subcultured.

The "liver progenitor cells of the invention" express α-fetoprotein (AFP), HNF4α, HNF1α, PROX1, TBX3, CD13, EpCAM and HHEX, which are known as liver progenitor cell markers.

One aspect of the invention relates to a cell fraction that comprises liver progenitor cells at 90% or greater with respect to the total cells, wherein the liver progenitor cells have the CPM-positive phenotype, have proliferation potency, and have differentiation potency to hepatocytes or cholangiocytes. This will hereunder also be referred to as "cell fraction that comprises liver progenitor cells of the invention".

The "cell fraction that comprises liver progenitor cells of the invention" comprises liver progenitor cells at 90% or greater, and preferably 91% or greater, 92% or greater, 93% or greater, 94% or greater, 95% or greater, 96% or greater, 97% or greater, 98% or greater or 99% or greater, of the total cells in the fraction. The "cell fraction that comprises liver progenitor cells of the invention" also encompasses a concentrated fraction of the liver progenitor cells of the invention, and a cell group obtained by culturing the concentrated fraction.

The "cell fraction that comprises liver progenitor cells of the invention" may be prepared by the method of preparing liver progenitor cells of the invention described above, for example, with no particular restrictions.

One aspect of the invention relates to a method of preparing hepatocytes that comprises a step of inducing differentiation of the liver progenitor cells of the invention to hepatocytes. This will hereunder also be referred to as "method of preparing hepatocytes of the invention".

One embodiment of the "method of preparing hepatocytes of the invention" relates to a method of preparing hepatocytes comprising the steps of (1) separating liver progenitor cells from a cell fraction that comprises liver progenitor cells, by using the CPM-positive phenotype as the marker, and (2) inducing differentiation of the separated liver progenitor cells to hepatocytes.

The differentiation inducement from liver progenitor cells to hepatocytes may employ a publicly known method, with no particular restrictions. For example, as described in NPL 2 (Si-Tayeb et al., Hepatology 2010, 51(1), 297-305), it may be carried out by treatment of medium containing human liver progenitor cells, using oncostatin M which is known as an interleukin-6 (IL-6) family cytokine.

According to one embodiment of the "method of preparing hepatocytes of the invention", the preparation method may further comprise a step of proliferating hepatocytes obtained by inducing differentiation. The conditions of cell culturing in the proliferation step are not particularly restricted so long as they do not inhibit proliferation of the hepatocytes.

One aspect of the invention relates to hepatocytes that can be prepared by the method of preparing hepatocytes of the invention, and that have proliferation potency. These will hereunder also be referred to as "hepatocytes of the invention".

The "hepatocytes of the invention" express CYP drug metabolizing enzymes (for example, CYP3A4, CYP2C19, CYP2C18, CYP2D6, CYP1A and CYP2C8) at high levels. For example, hepatocytes of the invention prepared by inducing differentiation of separated liver progenitor cells from a cell fraction that comprises liver progenitor cells by using the CPM-positive phenotype as the marker, can express CYP3A4 to at least twice the level of hepatocytes prepared by a step of inducing differentiation to a cell fraction of the same composition as the cell fraction described above, but without separating the liver progenitor cells by using the CPM-positive phenotype as the marker.

The "hepatocytes of the invention" have higher albumin producing ability and glycogen storage capacity than liver progenitor cells before inducing differentiation. Preferably, hepatocytes of the invention prepared by inducing differentiation of separated liver progenitor cells from a cell fraction that comprises liver progenitor cells by using the CPM-positive phenotype as the marker, have higher albumin producing ability and glycogen storage capacity than hepatocytes prepared by a step of inducing differentiation to a cell fraction of the same composition as the cell fraction described above, but without separating the liver progenitor cells by using the CPM-positive phenotype as the marker.

One aspect of the invention relates to a cell fraction that comprises "hepatocytes of the invention". The "cell fraction" preferably comprises the "hepatocytes of the invention" at 90% or greater, 91% or greater, 92% or greater, 93% or greater, 94% or greater, 95% or greater, 96% or greater, 97% or greater, 98% or greater or 99% or greater, of the total cells.

One aspect of the invention relates to a method of preparing cholangiocytes that comprises a step of inducing differentiation of the liver progenitor cells of the invention to cholangiocytes. This will hereunder also be referred to as "method of preparing cholangiocytes of the invention".

One embodiment of the "method of preparing cholangiocytes of the invention" relates to a method of preparing cholangiocytes comprising the steps of (1) separating liver progenitor cells from a cell fraction that comprises liver progenitor cells, by using the CPM-positive phenotype as the marker, and (2) inducing differentiation of the separated liver progenitor cells to cholangiocytes.

In the "method of preparing cholangiocytes of the invention", differentiation inducement from liver progenitor cells of the invention to cholangiocytes may employ a publicly known method, without any particular restrictions. For example, it may be carried out by a three-dimensional gel culturing method as described in Tanimizu et al., Mol Biol Cell, 2007, 18(4), 1472-1479 or Yanagida et al., PloS ONE 8, e67541.

According to one embodiment of the "method of preparing cholangiocytes of the invention", the preparation method may further comprise a step of proliferating cholangiocytes obtained by inducing differentiation. The conditions of cell culturing in the proliferation step are not particularly restricted so long as they do not inhibit proliferation of the cholangiocytes.

One aspect of the invention relates to cholangiocytes that can be prepared by the method of preparing cholangiocytes of the invention, and that have proliferation potency. These will hereunder also be referred to as "cholangiocytes of the invention".

The "cholangiocytes of the invention" express CK7, CFTR, AQP1, TGRS, SOX9 and HNF6, which are known as cholangiocyte markers.

One aspect of the invention relates to a cell fraction that comprises "cholangiocytes of the invention". The "cell fraction" preferably comprises the "cholangiocytes of the invention" at 90% or greater, 91% or greater, 92% or greater, 93% or greater, 94% or greater, 95% or greater, 96% or greater, 97% or greater, 98% or greater or 99% or greater, of the total cells.

One aspect of the invention relates to a method of preparing liver sinusoidal endothelial progenitor cells, comprising a step of separating off liver sinusoidal endothelial progenitor cells from a cell fraction that comprises liver sinusoidal endothelial progenitor cells, using the FLK1-positive, CD34-positive and CD31-positive phenotype as the marker. This will hereunder also be referred to as "method of preparing liver sinusoidal endothelial progenitor cells of the invention".

The "cell fraction that comprises liver sinusoidal endothelial progenitor cells" to be used in the "method of preparing liver sinusoidal endothelial progenitor cells of the invention" is not particularly restricted, and it may be prepared from any desired cells that differentiate to liver sinusoidal endothelial progenitor cells as a starting material. For example, it may be prepared by inducing differentiation of mesodermal cells. Also, for example, it may be prepared by inducing differentiation of hematopoietic stem cells. The cell fraction may also be prepared by extraction from a living body. For example, it may be prepared from an animal embryo liver. According to one embodiment of the method of preparing liver sinusoidal endothelial progenitor cells of the invention, the preparation method further comprises a step of preparing a cell fraction that comprises liver sinusoidal endothelial progenitor cells.

When the "cell fraction that comprises liver sinusoidal endothelial progenitor cells" to be used in the "method of preparing liver sinusoidal endothelial progenitor cells of the invention" is to be prepared by inducing differentiation of mesodermal cells, the mesodermal cells may be prepared by extraction from a living body, or they may be prepared by inducing differentiation of pluripotent stem cells. Differentiation from pluripotent stem cells to mesodermal cells may be carried out by a publicly known method. For example, it may be a method via an embryoid body (EB). It may also be carried out, for example, by the method described in Kattman S J, et al., Cell Stem Cell, 2011, 8, 228-40. The pluripotent stem cells are not particularly restricted, but are preferably mammalian pluripotent stem cells, more preferably pluripotent stem cells of a primate (human, monkey, etc.), rodent (mouse, rat, guinea pig, etc.), cat, canine, rabbit, sheep, pig, cow, horse, donkey, goat or ferret, even more preferably human pluripotent stem cells, and most preferably human iPS cells.

The differentiation inducement of mesodermal cells to liver sinusoidal endothelial progenitor cells may employ a publicly known method, with no particular restrictions. It may also be carried out, for example, by the method described in Kattman S J, et al., Cell Stem Cell, 2011, 8, 228-40.

One embodiment of the "method of preparing liver sinusoidal endothelial progenitor cells of the invention" relates to a method of preparing liver sinusoidal endothelial progenitor cells comprising the steps of (1) inducing differentiation of mesodermal cells to prepare a cell fraction that comprises liver sinusoidal endothelial progenitor cells, and (2) separating the liver sinusoidal endothelial progenitor cells by using the FLK1-positive, CD34-positive and CD31-positive phenotype as the marker.

FLK1, CD34 and CD31 are known as vascular endothelial cell markers. Surprisingly, the combination of FLK1, CD34 and CD31 has been demonstrated to be a specific marker for liver sinusoidal endothelial progenitor cells.

The step of separating off liver sinusoidal endothelial progenitor cells by using the FLK1-positive, CD34-positive and CD31-positive phenotype as the marker is not particularly restricted, and for example, it may be carried out by Fluorescence Activated Cell Sorting (FACS) or Magnetic Cell Sorting (MACS).

According to one embodiment of the "method of preparing liver sinusoidal endothelial progenitor cells of the invention", the preparation method may further comprise a step of proliferating the separated liver sinusoidal endothelial progenitor cells. The conditions of cell culturing in the proliferation step are not particularly restricted so long as they do not inhibit proliferation of the liver sinusoidal endothelial progenitor cells.

One aspect of the invention relates to a method of isolating liver sinusoidal endothelial progenitor cells, comprising a step of separating off liver sinusoidal endothelial progenitor cells from a cell fraction that comprises liver sinusoidal endothelial progenitor cells, using the FLK1-positive, CD34-positive and CD31-positive phenotype as the marker. Another aspect of the invention relates to a method of concentrating liver sinusoidal endothelial progenitor cells, comprising a step of separating off liver sinusoidal endothelial progenitor cells from a cell fraction that comprises liver sinusoidal endothelial progenitor cells, using the FLK1-positive, CD34-positive and CD31-positive phenotype as the marker.

One aspect of the invention relates to liver sinusoidal endothelial progenitor cells that can be prepared by the method of preparing liver sinusoidal endothelial progenitor cells of the invention, having the FLK1-positive, CD34-positive and CD31-positive phenotype, having proliferation potency, and having differentiation potency to liver sinusoidal endothelial cells. This will hereunder also be referred to as "liver sinusoidal endothelial progenitor cells of the invention".

The "liver sinusoidal endothelial progenitor cells of the invention" may be cryopreserved. The proliferation potency of the liver sinusoidal endothelial progenitor cells of the invention after freezing and thawing does not decline compared to the proliferation potency of the liver sinusoidal endothelial progenitor cells of the invention before cryopreservation. The "liver sinusoidal endothelial progenitor cells of the invention" may be preserved, for example, at −80° C., for 3 months or longer, 6 months or longer, 9 months or longer or 12 months or longer. The excellent proliferation potency and cryopreservability of the liver sinusoidal endothelial progenitor cells of the invention allows liver sinusoidal endothelial progenitor cells to be mass cultured as appropriate when necessary.

The "liver sinusoidal endothelial progenitor cells of the invention" may be subcultured.

One aspect of the invention relates to a cell fraction that comprises liver sinusoidal endothelial progenitor cells at 90% or greater with respect to the total cells, wherein the liver sinusoidal endothelial progenitor cells have the FLK1-positive, CD34-positive and CD31-positive phenotype, have proliferation potency, and have differentiation potency to liver sinusoidal endothelial cells. This will hereunder also be referred to as "cell fraction that comprises liver sinusoidal endothelial progenitor cells of the invention".

The "cell fraction that comprises liver sinusoidal endothelial progenitor cells of the invention" comprises liver sinusoidal endothelial progenitor cells at 90% or greater, and preferably 91% or greater, 92% or greater, 93% or greater, 94% or greater, 95% or greater, 96% or greater, 97% or greater, 98% or greater or 99% or greater, of the total cells in the fraction. The "cell fraction that comprises liver sinusoidal endothelial progenitor cells of the invention" also encompasses a concentrated fraction of the liver sinusoidal endothelial progenitor cells of the invention, and a cell group obtained by culturing the concentrated fraction.

The "cell fraction that comprises liver sinusoidal endothelial progenitor cells of the invention" may be prepared by the "method of preparing liver sinusoidal endothelial progenitor cells of the invention" described above, for example, with no particular restrictions.

One aspect of the invention relates to a method of preparing liver sinusoidal endothelial cells, comprising the steps of (1) inducing differentiation of liver sinusoidal endothelial progenitor cells of the invention using a TGF-β inhibitor to prepare a cell fraction that comprises liver sinusoidal endothelial cells, and (2) separating off liver sinusoidal endothelial cells from a cell fraction that comprises liver sinusoidal endothelial cells, using the CD31-positive and FcγR II-positive phenotype as the marker. This will hereunder also be referred to as "method of preparing liver sinusoidal endothelial cells of the invention".

One embodiment of the "method of preparing liver sinusoidal endothelial cells of the invention" relates to a method of preparing liver sinusoidal endothelial cells comprising the steps of (1) separating liver sinusoidal endothelial progenitor cells from a cell fraction that comprises liver sinusoidal endothelial progenitor cells using the FLK1-positive, CD34-positive and CD31-positive phenotype as the marker, (2) inducing differentiation of liver sinusoidal endothelial progenitor cells of the invention using a TGF-β inhibitor to prepare liver sinusoidal endothelial progenitor cells, and (3) separating liver sinusoidal endothelial cells from the liver sinusoidal endothelial cell-containing cell fraction using the CD31-positive and FcγR II-positive phenotype as the marker.

Throughout the present specification, the term "TGF-β inhibitor" refers to a drug for inhibiting the function or signal transduction of the transforming growth factor TGF-β, and it may be in the form of a low molecular compound, an antibody, an antisense compound, or the like. The TGF-β inhibitor to be used for the method of preparing liver sinusoidal endothelial cells of the invention is not particularly restricted, and examples include A83-01 (3-(6-methyl-2-pyridinyl)-N-phenyl-4-(4-quinolinyl)-1H-pyrazolo-1-carbothioamide), 1616451 (3-(pyridin-2-yl)-4-(4-quinonyl))-1H-pyrazole), LDN193189 (4-(6-(4-(piperazin-1-yl)phenyl) pyrazolo[1,5-a]pyrimidin-3-yl)quinoline), SB431542 (4-[4-(1,3-benzodioxol-5-yl)-5-pyridin-2-yl-1H-imidazol-2-yl] benzamide), SB-505124 (2-(5-benzo[1,3]dioxol-5-yl-2-tert-butyl-3H-imidazol-4-yl)-6-methylpyridine hydrochloride hydrate), SD-208 (2-(5-chloro-2-fluorophenyl)pteridin-4-yl)pyridin-4-yl-amine), SB-525334 (6-[2-(1,1-dimethyl-ethyl)-5-(6-methyl-2-pyridinyl)-1H-imidazol-4-yl]quinoxaline), LY-364947 (4-[3-(2-pyridinyl)-1H-pyrazol-4-yl]-quinoline), LY2157299 (4-[2-(6-methyl-pyridin-2-yl)-5,6-dihydro-4H-pyrrolo[1,2-b]pyrazol-3-yl]-quinoline-6-carboxylic acid amide) and D4476 (4-[4-(2,3-dihydro-1,4-benzodioxin-6-yl)-5-(2-pyridinyl)-1H-imidazol-2-yl] benzamide). It is preferably A83-01.

The step of separating off liver sinusoidal endothelial cells using the CD31-positive and FcγR II-positive phenotype as the marker is not particularly restricted, and for example, it may be carried out by Fluorescence Activated Cell Sorting (FACS) or Magnetic Cell Sorting (MACS).

According to one embodiment of the "method of preparing liver sinusoidal endothelial cells of the invention", the preparation method may further comprise a step of proliferating liver sinusoidal endothelial cells obtained by inducing differentiation. The conditions of cell culturing in the proliferation step are not particularly restricted so long as they do not inhibit proliferation of the liver sinusoidal endothelial cells.

One aspect of the invention relates to liver sinusoidal endothelial cells that can be prepared by the "method of preparing liver sinusoidal endothelial cells of the invention", having the CD31-positive and FcγR II-positive phenotype, and having proliferation potency. This will hereunder also be referred to as "liver sinusoidal endothelial cells of the invention".

The liver sinusoidal endothelial cells of the invention express Stab2, Lyve1 and factor VIII, which are known as liver sinusoidal endothelial cell markers.

The "liver sinusoidal endothelial cells of the invention" have the ability to take up acetylated LDL, as a characteristic function of vascular endothelial cells. The liver sinusoidal endothelial cells of the invention also have the ability to take up hyaluronic acid, as a characteristic function of liver sinusoidal endothelial cells. The "liver sinusoidal endothelial cells of the invention" also have the ability to form blood vessel-like structures.

Loss or reduced activity of factor VIII is considered a cause of hemophilia. For example, hemophilia can be treated by transplanting liver sinusoidal endothelial cells of the invention into a hemophilia patient.

One aspect of the invention relates to a cell fraction that comprises "liver sinusoidal endothelial cells of the invention". The "cell fraction" preferably comprises the "liver sinusoidal endothelial cells of the invention" at 90% or greater, 91% or greater, 92% or greater, 93% or greater, 94% or greater, 95% or greater, 96% or greater, 97% or greater, 98% or greater or 99% or greater, of the total cells.

One aspect of the invention relates to a cell fraction that comprises liver sinusoidal endothelial cells at 90% or greater with respect to the total cells, wherein the liver sinusoidal endothelial cells have the CD31-positive and FcγR II-positive phenotype and have proliferation potency. The cell fraction preferably comprises the liver sinusoidal endothelial cells at 91% or greater, 92% or greater, 93% or greater, 94% or greater, 95% or greater, 96% or greater, 97% or greater, 98% or greater or 99% or greater.

One aspect of the invention relates to a method of preparing hepatic stellate progenitor cells that comprises a step of separating off hepatic stellate progenitor cells from a cell fraction that comprises hepatic stellate progenitor cells, by using the ALCAM-positive phenotype as the marker. This will hereunder also be referred to as "method of preparing hepatic stellate progenitor cells of the invention".

The "cell fraction that comprises hepatic stellate progenitor cells" to be used in the "method of preparing hepatic stellate progenitor cells of the invention" is not particularly restricted, and it may be prepared from a starting material consisting of any desired cells that differentiate to hepatic stellate progenitor cells. For example, it may be prepared from a mesodermal cell cluster comprising hepatic stellate progenitor cells. It may also be prepared, for example, by inducing differentiation of mesenchymal stem cells (MSC). The cell fraction may also be prepared by extraction from a living body. For example, it may be prepared from an animal embryo liver. According to one embodiment of the method of preparing hepatic stellate progenitor cells of the invention, the preparation method further comprises a step of preparing a cell fraction that comprises liver progenitor cells.

When the "cell fraction that comprises hepatic stellate progenitor cells" to be used in the "method of preparing hepatic stellate progenitor cells of the invention" is to be prepared from mesodermal cells, the mesodermal cells may be prepared by extraction from a living body, or they may be prepared by inducing differentiation from pluripotent stem cells. Differentiation from pluripotent stem cells to mesodermal cells may be carried out by a publicly known method. For example, it may be a method via an embryoid body (EB). It may also be carried out, for example, by the method described in Kattman S J, et al., Cell Stem Cell, 2011, 8, 228-40. The pluripotent stem cells are not particularly restricted, but are preferably mammalian pluripotent stem cells, more preferably pluripotent stem cells of a primate (human, monkey, etc.), rodent (mouse, rat, guinea pig, etc.), cat, canine, rabbit, sheep, pig, cow, horse, donkey, goat or ferret, even more preferably human pluripotent stem cells, and most preferably human iPS cells.

Activated Leukocyte Cell Adhesion Molecule (ALCAM) is known as a marker for mesenchymal cells in the transverse septum mesenchyme. Surprisingly, it has been found that ALCAM is a hepatic stellate progenitor cell-specific marker molecule.

The step of separating off hepatic stellate progenitor cells by using the ALCAM-positive phenotype as the marker is not particularly restricted, and for example, it may be carried out by Fluorescence Activated Cell Sorting (FACS) or Magnetic Cell Sorting (MACS).

According to one embodiment of the "method of preparing hepatic stellate progenitor cells of the invention", the preparation method may further comprise a step of proliferating the separated hepatic stellate progenitor cells. The conditions of cell culturing in the proliferation step are not particularly restricted so long as they do not inhibit proliferation of the hepatic stellate progenitor cells.

One aspect of the invention relates to a method of isolating hepatic stellate progenitor cells that comprises a step of separating off hepatic stellate progenitor cells from a cell fraction that comprises hepatic stellate progenitor cells, by using the ALCAM-positive phenotype as the marker. Another aspect of the invention relates to a method of concentrating hepatic stellate progenitor cells that comprises a step of separating off hepatic stellate progenitor cells from a cell fraction that comprises hepatic stellate progenitor cells, by using the ALCAM-positive phenotype as the marker.

One aspect of the invention relates to hepatic stellate progenitor cells that can be prepared by the method of preparing hepatic stellate progenitor cells of the invention, having the ALCAM-positive phenotype, having proliferation potency and having differentiation potency to hepatic stellate cells. These will hereunder also be referred to as "hepatic stellate progenitor cells of the invention".

The "hepatic stellate progenitor cells of the invention" may be cryopreserved. The proliferation potency of the hepatic stellate progenitor cells of the invention after freezing and thawing does not decline compared to the proliferation potency of the hepatic stellate progenitor cells of the invention before cryopreservation. The "hepatic stellate progenitor cells of the invention" may be preserved, for example, at −80° C., for 3 months or longer, 6 months or longer, 9 months or longer or 12 months or longer. The excellent proliferation potency and cryopreservability of the hepatic stellate progenitor cells of the invention allows hepatic stellate progenitor cells to be mass cultured as appropriate when necessary.

One aspect of the invention relates to a cell fraction that comprises hepatic stellate progenitor cells at 90% or greater with respect to the total cells, wherein the hepatic stellate progenitor cells have the ALCAM-positive phenotype, have proliferation potency, and have differentiation potency to hepatic stellate cells. This will hereunder also be referred to as "cell fraction that comprises hepatic stellate progenitor cells of the invention".

The "cell fraction that comprises hepatic stellate progenitor cells of the invention" comprises hepatic stellate progenitor cells at 90% or greater, and preferably 91% or greater, 92% or greater, 93% or greater, 94% or greater, 95% or greater, 96% or greater, 97% or greater, 98% or greater or 99% or greater, of the total cells in the fraction. The "cell fraction that comprises hepatic stellate progenitor cells of the invention" also encompasses a concentrated fraction of the hepatic stellate progenitor cells of the invention, and a cell group obtained by culturing the concentrated fraction.

The "cell fraction that comprises hepatic stellate progenitor cells of the invention" may be prepared by the "method of preparing hepatic stellate progenitor cells of the invention" described above, for example, with no particular restrictions.

One aspect of the invention relates to a method of preparing hepatic stellate cells, comprising a step of inducing differentiation of hepatic stellate progenitor cells to hepatic stellate cells using ROCK inhibitor. This will hereunder also be referred to as "method of preparing hepatic stellate cells of the invention".

Rho kinase (Rho-associated protein kinase: ROCK) is a serine-threonine protein kinase identified as a target protein of the low molecular weight GTP-binding protein Rho, and it is known to contribute to various physiological functions such as unstriated muscle contraction and morphological changes in cells. Throughout the present specification, the term "ROCK inhibitor" refers to a drug for inhibiting the function of ROCK, and it may be in the form of a low molecular compound, an antibody, an antisense compound, or the like. The ROCK inhibitor to be used for the method of preparing hepatic stellate cells of the invention is not particularly restricted, and examples include Y27632 ((R)-(+)-trans-N-(4-pyridyl)-4-(1-aminoethyl)-cyclohexanecarboxamide), Fasudil (hexahydro-1-(5-isoquinolinesulfonyl)-1H-1,4-diazepine) and H-1152 ((S)-(+)-2-methyl-1-[(4-methyl-5-isoquinolinyl)sulfonyl]-hexahydro-1H-1,4-diazepine). It is preferably Y27632.

The hepatic stellate progenitor cells to be used in the "method of preparing hepatic stellate cells of the invention" is not particularly restricted, and it may be prepared from any desired cells that differentiate to hepatic stellate progenitor cells as a starting material. For example, it may be prepared from a mesodermal cell cluster comprising hepatic stellate progenitor cells. It may also be prepared by the "method of preparing hepatic stellate progenitor cells of the invention" described above, for example. The hepatic stellate progenitor cells may also be prepared by extraction from a living body. According to one embodiment of the method of preparing hepatic stellate cells of the invention, the preparation method further comprises a step of preparing hepatic stellate progenitor cells.

One embodiment of the method of preparing hepatic stellate cells of the invention relates to a method of preparing hepatic stellate cells comprising the steps of (1) separating off hepatic stellate progenitor cells from a cell fraction that comprises hepatic stellate progenitor cells, by using the ALCAM-positive phenotype as the marker, and (2) inducing differentiation of the hepatic stellate progenitor cells to hepatic stellate cells using a ROCK inhibitor. According to another embodiment of the method of preparing hepatic stellate cells of the invention, the hepatic stellate progenitor cells that are used are "hepatic stellate progenitor cells of the invention".

According to one embodiment of the method of preparing hepatic stellate cells of the invention, the preparation method may further comprise a step of proliferating hepatic stellate cells obtained by inducing differentiation. The conditions of cell culturing in the proliferation step are not particularly restricted so long as they do not inhibit proliferation of the hepatic stellate cells.

One aspect of the invention relates to hepatic stellate cells that can be prepared by the method of preparing hepatic stellate cells of the invention, and that have proliferation potency. This will hereunder also be referred to as "hepatic stellate cells of the invention".

One aspect of the invention relates to a cell fraction that comprises "hepatic stellate cells of the invention". The "cell fraction" preferably comprises the "hepatic stellate cells of the invention" at 90% or greater, 91% or greater, 92% or greater, 93% or greater, 94% or greater, 95% or greater, 96% or greater, 97% or greater, 98% or greater or 99% or greater, of the total cells.

One aspect of the invention relates to a method of preparing a hepatocyte tissue model, comprising a step of co-culturing the liver progenitor cells of the invention with at least one type of hepatic non-parenchymal cells selected from the group consisting of liver sinusoidal endothelial cells, hepatic stellate cells and liver mesothelial cells. This will hereunder also be referred to as "method of preparing a liver cellular tissue model of the invention".

Liver sinusoidal endothelial cells to be used in the "method of preparing a liver cellular tissue model of the invention" may be any liver sinusoidal endothelial cells from a mammal, bird, fish, reptile or amphibian, without any particular restrictions. They are preferably mammalian liver sinusoidal endothelial cells, more preferably liver sinusoidal endothelial cells of a primate (human, monkey, etc.), rodent (mouse, rat, guinea pig, etc.), cat, canine, rabbit, sheep, pig, cow, horse, donkey, goat or ferret, and most preferably human liver sinusoidal endothelial cells. The liver sinusoidal endothelial cells may also be liver sinusoidal endothelial cells of the invention. The liver sinusoidal endothelial cells may be prepared from a starting material consisting of any desired cells that differentiate to liver sinusoidal endothelial cells. For example, they may be prepared by inducing differentiation of pluripotent stem cells, mesodermal cells or liver sinusoidal endothelial cells. The liver sinusoidal endothelial cells may also be prepared by extraction from a living body. For example, they may be prepared from an animal embryo liver. The liver sinusoidal endothelial cells may also be prepared by the "method of preparing liver sinusoidal endothelial cells of the invention".

Hepatic stellate cells to be used in the "method of preparing a liver cellular tissue model of the invention" may be any hepatic stellate cells from a mammal, bird, fish, reptile or amphibian, without any particular restrictions. They are preferably mammalian hepatic stellate cells, more preferably hepatic stellate cells of a primate (human, monkey, etc.), rodent (mouse, rat, guinea pig, etc.), cat, canine, rabbit, sheep, pig, cow, horse, donkey, goat or ferret, and most preferably human hepatic stellate cells. The hepatic stellate cells may also be hepatic stellate cells of the invention. The hepatic stellate cells may be prepared from a starting material consisting of any desired cells that differentiate to hepatic stellate cells. For example, they may be prepared by inducing differentiation of pluripotent stem cells, mesodermal cells or hepatic stellate progenitor cells. The cell fraction may also be prepared by extraction from a living body. For example, it may be prepared from an animal embryo liver. The hepatic stellate cells may also be prepared by the "method of preparing hepatic stellate cells of the invention".

Liver mesothelial cells to be used in the "method of preparing a liver cellular tissue model of the invention" may be any liver mesothelial cells from a mammal, bird, fish, reptile or amphibian, without any particular restrictions. They are preferably mammalian liver mesothelial cells, and more preferably liver mesothelial cells of a primate (human, monkey, etc.), rodent (mouse, rat, guinea pig, etc.), cat, canine, rabbit, sheep, pig, cow, horse, donkey, goat or ferret. The liver mesothelial cells may be prepared from a starting material consisting of any desired cells that differentiate to liver mesothelial cells. For example, they may be prepared by inducing differentiation of pluripotent stem cells. The liver mesothelial cells may also be prepared by extraction from a living body. For example, it may be prepared from an animal embryo liver.

In the "method of preparing a liver cellular tissue model of the invention", the conditions for the co-culturing step are not particularly restricted so long as they promote differentiation inducement of liver progenitor cells, and for example, two-dimensional culturing (plate culturing) or three-dimensional culturing is carried out. Three-dimensional culturing is preferred.

One aspect of the invention relates to a liver cellular tissue model that comprises hepatocytes and at least one type of hepatic non-parenchymal cells selected from the group consisting of liver sinusoidal endothelial cells, hepatic stellate cells and liver mesothelial cells, and that can be prepared by the "method of preparing a liver cellular tissue model of the invention. This will hereunder also be referred to as "liver cellular tissue model of the invention".

One aspect of the invention relates to a pharmaceutical composition comprising liver progenitor cells of the invention, a cell fraction that comprises liver progenitor cells of the invention, hepatocytes of the invention, cholangiocytes of the invention, liver sinusoidal endothelial progenitor cells of the invention, a cell fraction that comprises liver sinusoidal endothelial progenitor cells of the invention, liver sinusoidal endothelial cells of the invention, hepatic stellate progenitor cells of the invention, a cell fraction that comprises hepatic stellate progenitor cells of the invention, hepatic stellate cells of the invention or a liver cellular tissue model of the invention. This will hereunder also be referred to as "pharmaceutical composition of the invention".

The "pharmaceutical composition of the invention" may further comprise a pharmaceutically acceptable carrier, diluent, buffering agent or excipient, or a combination thereof.

According to one embodiment of the "pharmaceutical composition of the invention", the pharmaceutical composition is a cell grafting treatment material or cell grafting treatment composition, or a regenerative medicine material or regenerative medicine composition.

The site of administration of the pharmaceutical composition of the invention is not particularly restricted, and the administration may be intrahepatic, intrasplenic, intraportal, intraintestinal, intraperitoneal, or into the kidney capsules or lymph nodes.

One aspect of the invention relates to a method for screening liver disease treatment agents, comprising administering a candidate liver disease treatment agent to hepatocytes of the invention or to a liver cellular tissue model of the invention. This will hereunder also be referred to as "liver disease treatment agent screening method of the invention".

The liver disease target of the "liver disease treatment agent screening method of the invention" is not particularly restricted, and examples include phenylketonuria and other aminoacidemias, hemophilia and other coagulation factor deficiencies, familial hypercholesterolemia and other lipid metabolism disorders, urea cycle disorder, glycogen storage disease, galactosemia, levulosemia, tyrosinemia, protein/carbohydrate metabolism deficiencies, organic acidemia, mitochondrial disease, peroxisome/lysosome defects, protein synthesis defects, hepatocyte transporter defects, glycosylation disorders, hepatitis, hepatic cirrhosis, inborn errors of metabolism, acute liver failure, acute liver infection, acute chemical toxicity, chronic liver failure, cholangitis, biliary cirrhosis, Alagille syndrome, α-1-antitrypsin deficiency, autoimmune hepatitis, biliary atresia, hepatic cancer, liver cystic disease, fatty liver, galactosemia, biliary calculus, Gilbert's syndrome, hemochromatosis, hepatitis A, hepatitis B, hepatitis C and other hepatitis virus infections, porphyria, primary sclerosing cholangitis, Reye's syndrome, sarcoidosis, tyrosinemia, glycogen storage disease type I and Wilson's disease.

One aspect of the invention relates to a method of evaluating drug hepatotoxicity, comprising administering a drug to "hepatocytes of the invention" or to a "liver cellular tissue model of the invention". This will hereunder also be referred to as "method of evaluating drug hepatotoxicity of the invention".

The "method of evaluating drug hepatotoxicity of the invention" comprises, for example, examining inhibiting activity of CYP (such as CYP3A4, CYP2C19, CYP2C18, CYP2D6, CYP1A and CYP2C8), with no particular restrictions.

One aspect of the invention relates to a method of preparing hepatocytes for an infectious liver disease model, comprising the steps of (1) infecting "liver progenitor cells of the invention" or "liver progenitor cells in a "cell fraction that comprises liver progenitor cells of the invention" with a pathogen, and (2) inducing differentiation of the pathogen-infected liver progenitor cells to prepare hepatocytes for an infectious disease model. Another aspect of the invention relates to a method of preparing hepatocytes for an infectious disease model, comprising a step of infecting liver cells of the invention with a pathogen. These preparation methods will hereunder also be referred to as "method of preparing hepatocytes for an infectious disease model of the invention".

The pathogen to be used for the "method of preparing hepatocytes for an infectious disease model of the invention" is not particularly restricted, and examples include hepatitis virus (for example, hepatitis A virus (HAV), hepatitis B virus (HBV), hepatitis C virus (HCV), hepatitis D virus (HDV), hepatitis E virus (HEV), hepatitis F virus (HFV), hepatitis G virus (HGV), hepatitis TT virus (HTTV), and malaria protozoa.

In the "method of preparing hepatocytes for an infectious disease model of the invention", the "infectious disease" depends on the infecting pathogen, but examples include hepatitis (for example, hepatitis A, hepatitis B, hepatitis C, hepatitis D, hepatitis E, hepatitis F, hepatitis G and hepatitis TT) and malaria.

One aspect of the invention relates to hepatocytes for an infectious disease model, that can be prepared by the method of preparing hepatocytes for an infectious disease model of the invention. These will hereunder also be referred to as "hepatocytes for an infectious disease model of the invention".

One aspect of the invention relates to a method of preparing infectious disease model tissue, comprising the steps of (1) infecting liver progenitor cells of the invention with a pathogen, and (2) co-culturing the pathogen-infected liver progenitor cells with at least one type of hepatic non-parenchymal cells selected from the group consisting of liver sinusoidal endothelial cells, hepatic stellate cells and liver mesothelial cells. This will hereunder also be referred to as "method of preparing infectious disease model tissue of the invention".

The liver sinusoidal endothelial cells, hepatic stellate cells and liver mesothelial cells to be used in the "method of preparing infectious liver disease model tissue of the invention" are not particularly restricted, and may be the same as those mentioned above for the "method of preparing a liver cellular tissue model of the invention".

The pathogen to be used in the "method of preparing infectious disease model tissue of the invention" and its associated disease are not particularly restricted, and they may be the same as mentioned for the "hepatocytes for an infectious disease model of the invention".

One aspect of the invention relates to infectious disease model tissue that can be prepared by the method of preparing infectious disease model tissue of the invention. This will hereunder also be referred to as "infectious disease model tissue of the invention".

One aspect of the invention relates to a method for screening infectious liver disease treatment agents, comprising administering a candidate infectious liver disease treatment agent to "hepatocytes for an infectious disease model of the invention" or to "infectious disease model tissue of the invention".

One aspect of the invention relates to a kit comprising liver progenitor cells of the invention, a cell fraction that comprises liver progenitor cells of the invention, hepatocytes of the invention, cholangiocytes of the invention, liver sinusoidal endothelial progenitor cells of the invention, a cell fraction that comprises liver sinusoidal endothelial progenitor cells of the invention, liver sinusoidal endothelial cells of the invention, hepatic stellate progenitor cells of the invention, a cell fraction that comprises hepatic stellate progenitor cells of the invention, hepatic stellate cells of the invention or a liver cellular tissue model of the invention. This will hereunder also be referred to as "kit of the invention".

The kit of the invention is not particularly restricted, and for example, it may be used for preparation of hepatocytes of the invention, cholangiocytes of the invention, liver sinusoidal endothelial cells of the invention, hepatic stellate cells of the invention or a liver cellular tissue model of the invention, for preparation of a pharmaceutical composition of the invention, for a liver disease treatment agent screening method of the invention, for a method of evaluating drug hepatotoxicity of the invention, for preparation of hepatocytes for an infectious disease model of the invention, for preparation of infectious disease model tissue of the invention, or for a method for screening infectious liver disease treatment agents. The kit of the invention may also comprise a kit instruction manual.

EXAMPLES

The present invention will now be explained in further detail with reference to examples, with the understanding that the scope of the invention is naturally not limited to the examples.

<Cytoplasm Protein Flow Cytometry Analysis>

A Cytofix/cytoperm fixation/permeabilization kit (BD Biosciences) was used to fix and permeabilize cells, and the cytoplasm proteins were labeled by an antigen-antibody method. A MoFlo XDP cell sorter (Beckman Coulter, Inc.) was then used for flow cytometry analysis.

<Quantitative RT-PCR>

TRIzol reagent (Life Technologies) or NucleoSpin RNA XS (MACHEREY-NAGAL, Duren, Germany) was used to extract the RNA. The remaining genomic DNA was digested using DNaseI (Life Technologies), and then a PrimeScript II 1st strand cDNA Synthesis Kit (Takara Bio, Shiga, Japan) was used to synthesize single-stranded cDNA. The quantitative RT-PCR was carried out using SYBR Premix EX TaqII (Takara Bio, Shiga, Japan), and the data were calculated according to the ddCt method with β-actin as the standardization control.

The primers used in the quantitative RT-PCR were as follows.

TABLE 1

| | | Left Primer | SEQ ID NO | Right Primer | SEQ ID NO. |
|---|---|---|---|---|---|
| Mouse | Actb | TTCTTTGGAGCTCCTTCGTT | 1 | ATGGAGGGGAATACAGCCC | 2 |
| | CD34 | TGGGTAGCTCTCTGCCTGAT | 3 | TGGTAGGAACTGATGGGGAT | 4 |
| | Stab2 | TGTCCAGACGGCTACATCAA | 5 | CCAGGGATATCCAGGAGGTA | 6 |
| | Flt4 | CTCTGCCTCGGACTCCTC | 7 | CCCCGGTGTCAATCACATA | 8 |
| | Lyve1 | CCTCCAGCCAAAAGTTCAAA | 9 | TCCAACACCGGGTAAAATGT | 10 |
| | CD31 | CTGGTGCTCTATGCAAGCCT | 11 | AGTTGCTGCCCATTCATCAC | 12 |
| | F8 | TCATGTATAGCCTGGATGGGA | 13 | GATGAGTCCACATTGCCAAA | 14 |
| | Cpm | CCCGTTTAGAACCAACAAGC | 15 | CACTCGTGTCCAGGGACTGT | 16 |

TABLE 1-continued

| | | Left Primer | SEQ ID NO | Right Primer | SEQ ID NO. |
|---|---|---|---|---|---|
| Human | ACTB | GCACAGAGCCTCGCCTT | 17 | GTTGTCGACGACGAGCG | 18 |
| | OCT4 | GAAGGAGAAGCTGGAGCAAA | 19 | CTTCTGCTTCAGGAGCTTGG | 20 |
| | MESP1 | GATGGAGCCAAGCCCAC | 21 | CTCAGGCAGCCACTCCAG | 22 |
| | CD31 | CGGGGAATTCCAGTATCAC | 23 | AGGCCCCAATACACTTCACA | 24 |
| | VE Cad | TGGAGAAGTGGCATCAGTCAACA | 25 | TCTACAATCCCTTGCAGTGTGAG | 26 |
| | STAB2 | CCTGTGAAACCTGTGCTGAC | 27 | CCATCGCCATCTAGTCCACTG | 28 |
| | LYVE1 | ACTTCCATCTGGACCA | 29 | CCTTTTTGCTCACAAG | 30 |
| | FLK1 | CGGCTCTTTCGCTTACTGTT | 31 | CCTGTATGGAGGAGGAGGAA | 32 |
| | CD34 | GCCATTCAGCAAGACAACAC | 33 | AAGGGTTGGGCGTAAGAGAT | 34 |
| | Fc γ RIIB | AGTTTCAGCACAGCCTTTGG | 35 | AGCCTTGGGGTCATATGCTT | 36 |
| | FB | CTTTTGCGATTCTGCTTTAGTGC | 37 | TAGGACGAAATCTTGCGTCCA | 38 |
| | ALCAM | CTTCTGCCTCTTGATCTCCG | 39 | AGGTACGTCAAGTCGGCAAG | 40 |
| | HGF | CGGTGGGAGTACTGTGCAAT | 41 | CCCTGTAGCCTTCTCCTTGA | 42 |
| | CYGB | TCTATGCCAACTGCGAGGAC | 43 | TCCTCCATGTGCTTGAACTG | 44 |
| | NGFR | CTGCTGCTGTTGCTGCTTCT | 45 | CAGGCTTTGCAGCACTCAC | 46 |
| | DES | GAAGCTGCTGGAGGGAGAG | 47 | ATGGACCTCAGAACCCCTTT | 48 |
| | LRAT | TACTGCAGATATGGGAGCCC | 49 | CCAAGACTGCTGAAGCAAGA | 50 |
| | HNF4 α | GCAGGCTCAAGAAA TGCTTC | 51 | GGCTGCTGTCCTCATAGCTT | 52 |
| | AFP | AGAGGAGATGTGCTGGATTG | 53 | GTGGTCAGTTTGCAGCATTC | 54 |
| | ALB | TGCTGATGAGTCAGCTGAAAA | 55 | TCAGCCATTTCACCATAGGTT | 56 |
| | CPM | GCATCGAAGCGTTTTTGAAG | 57 | CCACAACAAGAACCCACAGG | 58 |
| | CYP3A4 | TTTTGTCCTACCATAAGGGCTTT | 59 | CACAGGCTGTTGACCATCAT | 60 |
| | CYP2C19 | TTGCTTCCTGATCAAAATGG | 61 | GTCTCTGTCCCAGCTCCAAG | 62 |
| | CYP2C18 | ATGAACAGTGCTCGGGACTT | 63 | TGGCTATCAAGCTTTCAACAG | 64 |
| | CYP2D6 | TGGACTTCCAGAACACACCA | 65 | CCCATTGAGCACGACCAC | 66 |
| | CYPIA2 | CTTCGTAAACCAGTGGCAGG | 67 | AGGGCTTGTTAATGGCAGTG | 68 |
| | CYP2C8 | CTCGGGACTTTATGGATTGC | 69 | CAGTGCCAACCAAGTTTTCA | 70 |
| | CK7 | CTGCCTACATGAGCAAGGTG | 71 | GGGACTGCAGCTCTGTCAAC | 72 |
| | AQP1 | CTCTCAGGCATCACCTCCTC | 73 | GGAGGGTCCCGATGATCT | 74 |
| | CFTR | ACAGAAGCGTCATCAAAGCA | 75 | CCACTCAGTGTGATTCCACCT | 76 |
| | SOX9 | GACGCTGGGCAAGCTCT | 77 | GTAATCCGGGTGGTCCTTCT | 78 |
| | HNFt α | CCTCAAAGAGCTGGAGAACCT | 79 | GACTTGACCATCTTCGCCAC | 80 |
| | PROX1 | ACAGGGCTCTGAACATGCAC | 81 | CGCATTGAAAAACTCCCGTA | 82 |
| | TBX3 | CTTCCACGTCCAGCAGCA | 83 | GCCATGTACGTGTAGGGGTA | 84 |
| | CD13 | AACCTCATCCAGGCAGTGAC | 85 | AAGCCTCTTTCCTCGTTGTC | 86 |
| | CD133 | CCATTGGGATTCTCTTTGAA | 87 | TTTGGATTCATATGCCTTCTGT | 88 |
| | EpCAM | CTGAATTCTCAATGCAGGGTC | 89 | CCCATCTCCTTTATCTCAGCC | 90 |
| | HHEX | CCTCTGTACCCCTTCCCG | 91 | GGGGCTCCAGAGTAGAGGTT | 92 |
| | ABCBI1 | TTCCAGGAAAAGCATGTGTG | 93 | CATTTCGCTCTCGATGTTCA | 94 |
| | CEBPA | GAGGGACCGGAGTTATGACA | 95 | TTCACATTGCACAAGGCACT | 96 |
| | CPSI | GGAAAAGACACTGAAAGGGCT | 97 | CCCAAGGCATTTTGAAATCT | 98 |
| | qhCD81 | TCGTCTTCAATTTCGTCTTCTG | 99 | CTCCCAGCTCCAGATACAGG | 100 |
| | qhSLC10A1 | ATCTTGGTCTGTGGCTGCTC | 101 | AGAAGGTGGAGCAGGTGGT | 102 |
| | qhCLDN1 | GGCAGATCCAGTGCAAACTC | 103 | TCACTCCCAGGAGGATGC | 104 |
| | qhOCLN | CATTTATGATGAGCAGCCCC | 105 | TAGTCAGATGGGGGTGAAGG | 106 |
| | qhSCARBI | CATCAAGCAGCAGGTCCTTA | 107 | AGACGGAGAGATAGAAGGGGA | 108 |

<Immunocytochemical Staining>

The cultured cells were fixed for 10 minutes with 10% formalin solution (Wako Pure Chemical Industries, Ltd.), and then they were permeabilized for 15 minutes with 0.2% Triton-X100 (Wako Pure Chemical Industries, Ltd.). After blocking with a 5% skim milk solution (BD Biosciences), the primary antibody was reacted overnight at 4° C. After rinsing with PBS, the fluorescently labeled secondary antibody was reacted for 2 hours at room temperature, and contrast stained with Hoechst33342 (Sigma-Aldrich Corporation, St. Louis, US).

<Separation of Cells with Automatic Magnetic Cell Separator>

Separation of the liver sinusoidal endothelial progenitor cells in Example 4(2), separation of the liver sinusoidal endothelial cells in Example 5(1) and separation of the hepatic stellate progenitor cells in Example 6 were carried out as follows.

The cells were dissociated using 0.05% trypsin/0.5 mM EDTA or Accumax (Innovative Cell Technologies, Inc.), and suspended with 0.03% BSA-PBS. The prepared cells were blocked for 20 minutes with FcR block reagent (Miltenyi Biotech, Bergisch-Gladbach, Germany), and labeled for 30 minutes with primary antibody recognizing antigen specific to each cell. After rinsing the cells, they were labeled for 20 minutes with anti-FITC microbeads (Miltenyi Biotech) and anti-PE microbeads (Miltenyi Biotech) as necessary, and the target cells were concentrated with an autoMACS Pro separator (Miltenyi Biotech). A MoFlo XDP cell sorter (Beckman Coulter, Inc.) was then used for separation.

The primary antibodies, secondary antibodies and microbeads used in the examples were as follows.

TABLE 2

| | Type | Manufacturer (Catalog #) |
|---|---|---|
| Primary antibody | | |
| AFP | Rabbit | Dako (A000829) |
| AFP | Mouse | Sigma-Aldrich (A8452) |
| ALB | Rabbit | Dako (A0001) |
| ALB | Mouse | Nippon bio-test laboratories (0902-1) |
| HNF4-α | Goat | SantaCruz (sc-6556) |
| CK7 | Mouse | Dako (M7018) |
| CD49f | Rat | BD Pharmingen (555734) |
| PKC | Rabbit | SantaCruz (sc-216) |

TABLE 2-continued

| | Type | Manufacturer (Catalog #) |
|---|---|---|
| CTNNB1 | Mouse | BD Pharmingen (61053) |
| AQP1 | Rabbit | SantaCruz (sc-20810) |
| OCT4 | Rabbit | SantaCruz (sc-9081) |
| GATA4 | Goat | SantaCruz (sc-1237) |
| FOXA2 | Goat | SantaCruz (sc-6554) |
| Anti-Carboxypeptidase M | Mouse | abcam (ab49278) |
| PE Anti-Human CD31 | Mouse | BD Bioscience (555446) |
| FITC anti-human CD34 Antibody | Mouse | BioLegend (343604) |
| CD309 (VEGFR-2/KDR)-APC antibody | Mouse | Miltenyi (130-093-601) |
| ALCAM CD166-Biotin antibody | Mouse | Miltenyi (130-106-617) |
| APC anti-human CD32 Antibody | Mouse | BioLegend (303208) |
| Anti-Factor VIII antibody Secondary antibody | Mouse | abcam (ab41187) |
| PE anti-Mouse IgG | Goat | BioLegend (405307) |
| APC Streptavidin | | BD Bioscience (554067) |
| Alexa Fluor 555 anti-mouse IgG Microbeads | Goat | Life Technologies (A21424) |
| Anti-PE-microbeads | Mouse | Miltenyi Biotec (130-048-801) |
| Anti-FITC microbeads | Mouse | Miltenyi Biotec (130-048-701) |

Example 1

(1) Preparation of Human Liver Progenitor Cells

Human iPS cells (454E2, RIKEN Cell Bank) were induced to differentiate into human liver progenitor cells by the following procedure described in NPL 2 (Si-Tayeb et al., Hepatology 2010, 51(1), 297-305). The human iPS cells were cultured for 5 days in RPMI medium containing B27 and 100 ng/ml activin A, in an environment of 5% $CO_2$, ambient oxygen. They were then cultured for 5 days in RPMI/B27 medium with addition of 20 ng/ml BMP4 and 10 ng/ml FGF2, in an environment of 4% $O_2$/5% $CO_2$. They were subsequently cultured in RPMI/B27 medium with addition of 20 ng/ml hepatocyte growth factor (HGF) in an environment of 4% $O_2$/5% $CO_2$ for at least 10 days, to obtain a cell group including human liver progenitor cells. A MoFlo XDP cell sorter (Beckman Coulter) was used to separate the human liver progenitor cells (CPM-positive cells) and CPM-negative cells from the cell group. The separation could also be carried out in the same manner using an autoMACS Pro Separator (Miltenyi Biotech).

Figure 2:
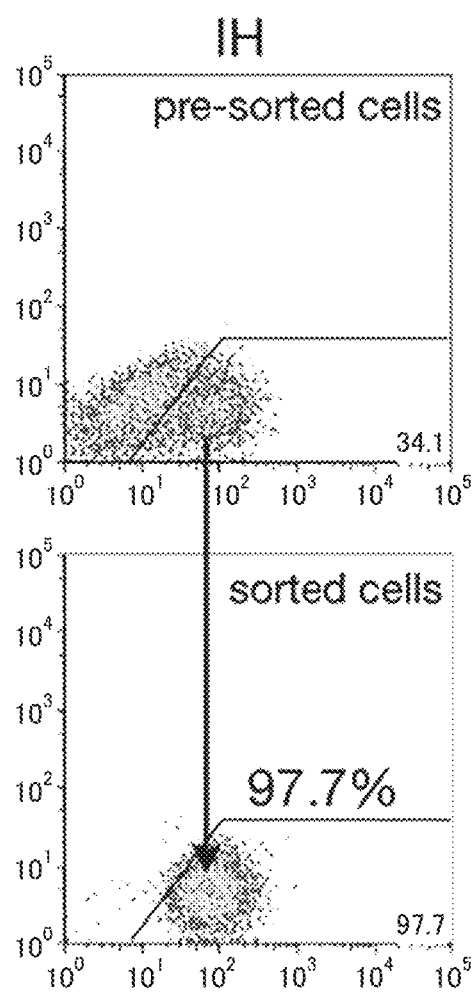
FIG. 2 shows the results of flow cytometry analysis when separating cells from a cell group comprising liver progenitor cells (immature hepatocytes: IH), by using CPM positivity as the marker. The cell separation successfully separated off 97.7% of the liver progenitor cells.
Figure 3:
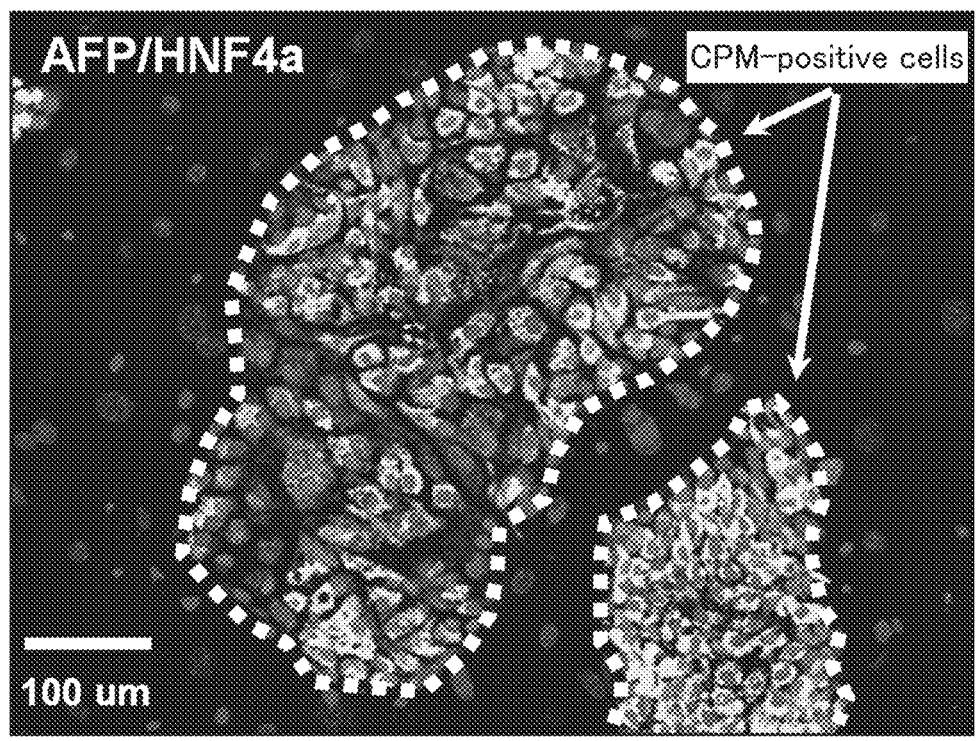
FIG. 3 shows the results of immunocytochemical staining of CPM-positive cells.

FIG. 1 shows the results of flow cytometry analysis indicating the time-dependent change in the CPM-positive cell fraction after inducing differentiation from human iPS cells to hepatocytes. FIG. 2 shows the results of flow cytometry analysis when separating cells from a cell group comprising liver progenitor cells (immature hepatocytes: IH), by using CPM positivity as the marker. Following the differentiation-inducing procedure described above, a cell fraction was obtained with a CPM-positive cell content of approximately 40% maximum. By separating only the CPM-positive cells from the cell fraction, a concentrated cell fraction was obtained with a CPM-positive cell content of 97.7%. When differentiation to mature hepatocytes was induced without separation of the CPM-positive cells, however, the CPM-positive cell content decreased. This indicates that CPM is a specific cell surface marker on liver progenitor cells. FIG. 3 shows the results of immunocytochemical staining of isolated CPM-positive cells. Expression of AFP and HNF4a, known as hepatocyte precursor markers, was observed.

Figure 4:
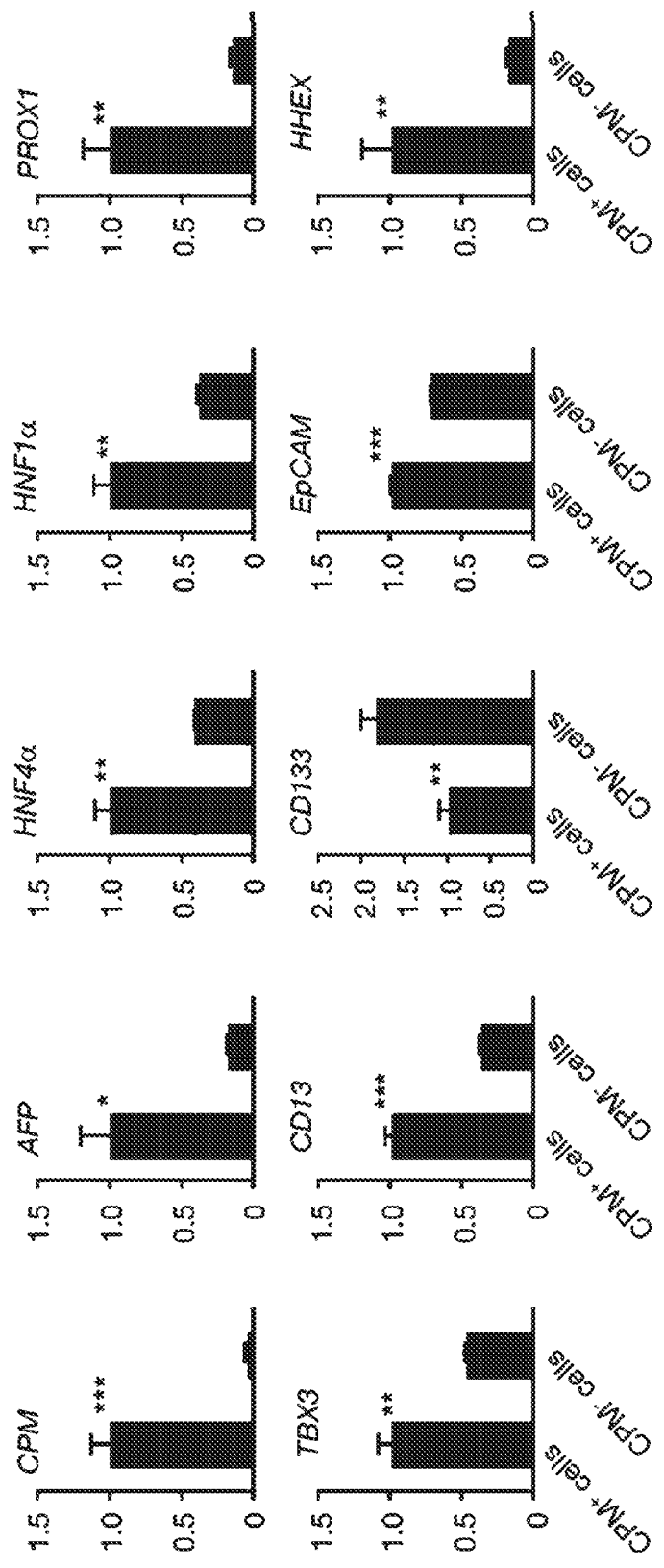
FIG. 4 shows the comparative results for the expression levels of liver progenitor cell markers in CPM-positive cells and CPM-negative cells. *$p<0.05$, $p<0.01$, *$p<0.001$. The results are expressed as mean±SEM for eight experiments.

FIG. 4 shows the comparative results for the expression levels of cell markers in CPM-positive cells and CPM-negative cells obtained by quantitative RT-PCR. The CPM-positive cells expressed AFP, HNF4α, HNF1α, PROX1, TBX3, CD13, EpCAM and HHEX, known as hepatocyte precursor markers, in significant amounts compared to the CMP-negative cells. On the other hand, the expression level of CD133, known as a cholangiocyte marker, was significantly lower in the CPM-positive cells compared to the CPM-negative cells.

(2) Proliferation of Human Liver Progenitor Cells

The separated CPM-positive cells were cultured in DMEM-F12 (Sigma-Aldrich) with addition of 10% FBS (JRH Biosciences), penicillin-streptomycin-glutamine, ITS, N-2 supplement, MEM non-essential amino acid solution, L-glutamine (Life Technologies), ascorbic acid (1 mM), nicotinamide (10 mM), N-acetyl-cysteine (0.2 mM) (Sigma-Aldrich), dexamethasone ($1\times10^{-7}$ M), HGF (20 ng/ml), EGF (10 ng/ml) (PeproTech), Y-27632(5 µM) (Wako) and A83-01(2.5 µM) (Tocris), on mitomycin C-treated MEF feeder cells ($2.0\times10^4$ cell/$cm^2$).

When cultured on the MEF feeder cells, the CPM-positive cells formed colonies. However, when the CPM-negative cells were cultured under the same conditions, no such colonies were formed. The CPM-positive cells were confluent by the 7th day after cell seeding (FIG. 5). The cells could be subcultured in vitro, reaching cell proliferation of ≥1000× by the 5th subculture (FIG. 5). The properties of the liver progenitor cells before cryopreservation were maintained even after cryopreservation of the cells for 6 months followed by thawing.

Example 2

(1) Inducing Differentiation from Human Liver Progenitor Cells to Human Hepatocytes.

As described in NPL 2, the CPM-positive cells that had been proliferated to confluency in Example 1(2) were incubated for 5 to 10 days in hepatocyte basal medium (Lonza) with addition of HCM Single Quots (excluding EGF) and oncostatin M (20 ng/ml) (PeproTech), to induce differentiation to human hepatocytes.

(2) Albumin Production and Glycogen Storage

Figure 6:
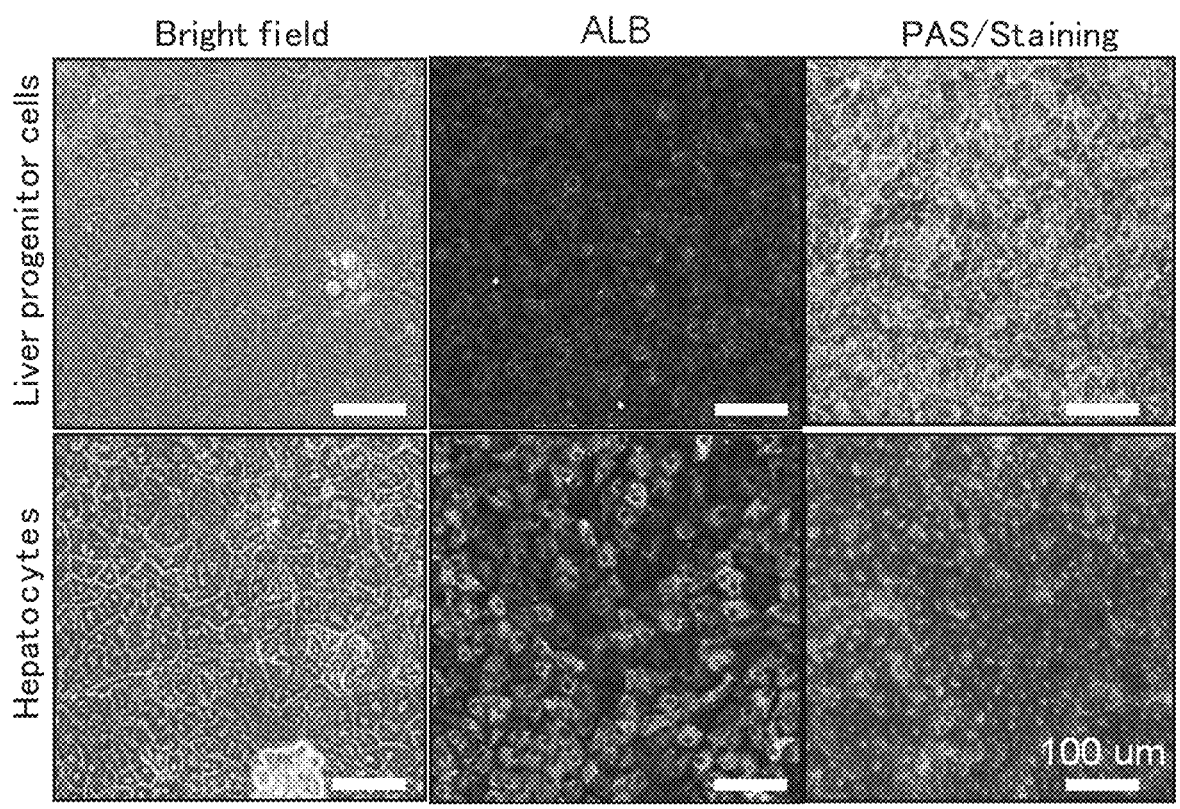
FIG. 6 shows observation of progenitor cells before differentiation inducement and hepatocytes obtained by differentiation inducement with a bright-field microscope, observation of albumin in the cells with immunocytochemical staining, and observation of glycogen accumulation in the cells with PAS staining.

Observation of progenitor cells before differentiation inducement and hepatocytes obtained by differentiation inducement with a bright-field microscope, observation of albumin in the cells with immunocytochemical staining, and observation of glycogen accumulation in the cells with PAS staining are shown in FIG. 6. The PAS staining was carried out according to standard protocol, using Cold Schiff's Reagent (Wako Pure Chemical Industries, Ltd.). Higher albumin production and higher glycogen accumulation were confirmed in the hepatocytes obtained by inducing differentiation, compared to the liver progenitor cells before inducing differentiation.

(3) CYP450 Expression

Figure 7:
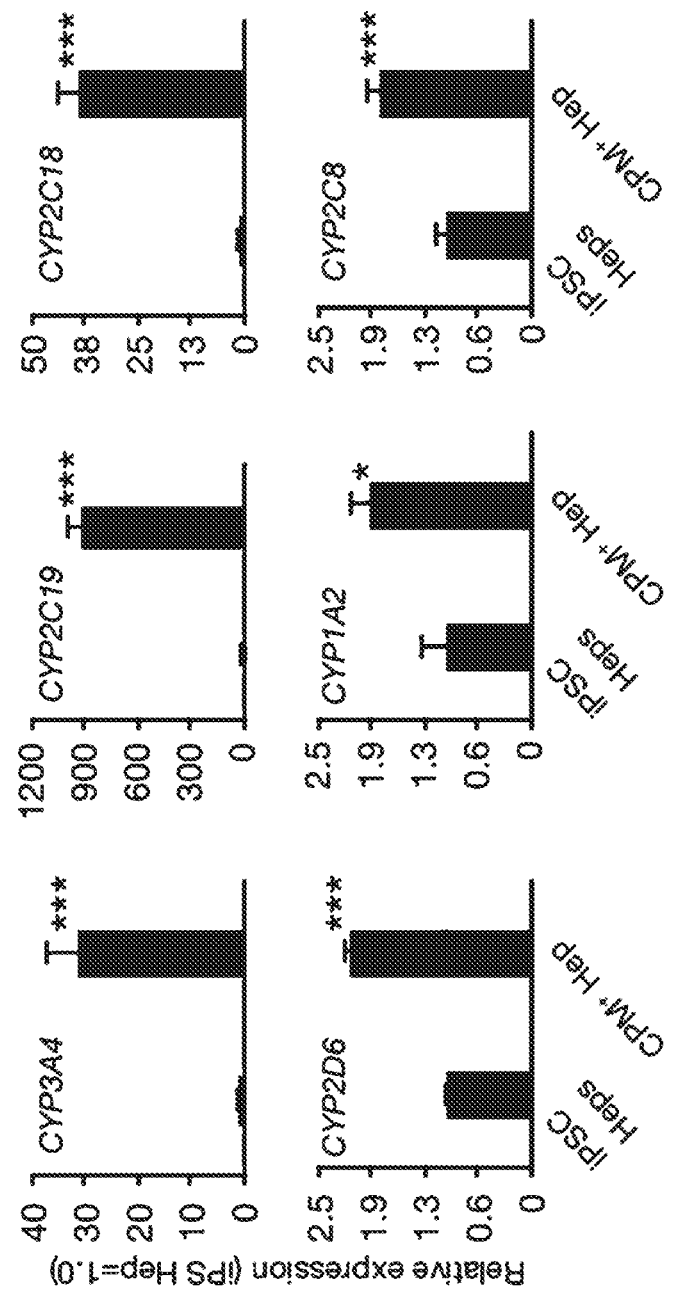
FIG. 7 shows the comparative results for CYP450 mRNA expression levels in human iPS cell-derived hepatocytes obtained by inducing differentiation of liver progenitor cells without separation using the CPM-positive marker (iPSC Heps), and human iPS cell-derived hepatocytes obtained by inducing differentiation of liver progenitor cells separated by using the CPM-positive marker (CPM+Heps). The results are expressed as mean±SEM for six independent experiments. *$p<0.05$, $p<0.01$, *$p<0.001$.
Figure 8:
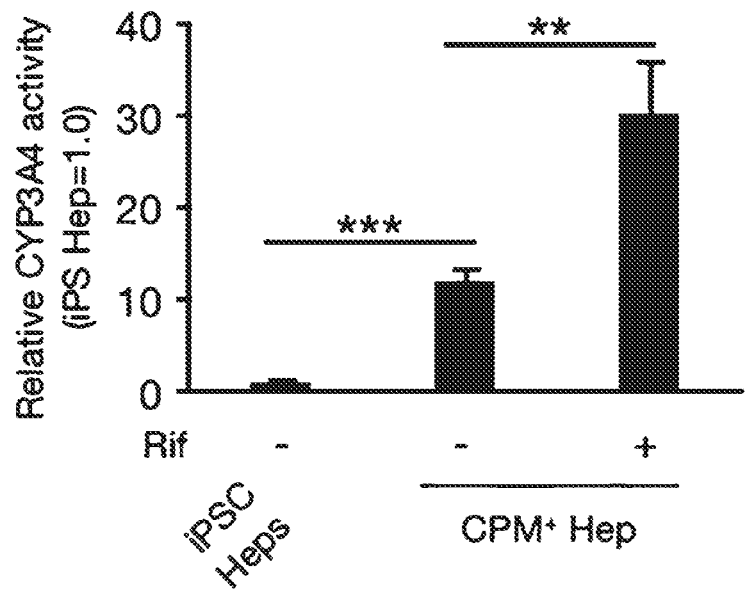
FIG. 8 shows the comparative results for CYP3A4 mRNA expression levels in human iPS cell-derived hepatocytes obtained by inducing differentiation of liver progenitor cells without separation using the CPM-positive marker (iPSC Heps), and human iPS cell-derived hepatocytes obtained by inducing differentiation of liver progenitor cells separated using the CPM-positive marker (CPM+Heps). The results are expressed as mean±SEM for at least three independent experiments. *$p<0.05$, $p<0.01$, *$p<0.001$. Rif stands for rifampicin.

CYP450 mRNA expression was analyzed by quantitative RT-PCR, for the human hepatocytes obtained in (1) above and human hepatocytes derived from human iPS cells by the procedure described in NPL 2 (Si-Tayeb et al., Hepatology 2010, 51(1), 297-305) as the conventional method (that is, human iPS cell-derived hepatocytes obtained by inducing differentiation of liver progenitor cells without separation using CPM-positivity as the marker. The results are shown in FIG. 7 and FIG. 8. The human hepatocytes obtained in (1) above exhibited higher expression of CYP3A4, CYP2C19, CYP2C18, CYP2D6, CYP1A2 and CYP2C8 compared to the human hepatocytes prepared by the conventional method. It was also found that addition of rifampicin further increased CYP3A4 expression. The human hepatocytes prepared by the method of the invention have properties distinct from those of human iPS cell-derived hepatocytes obtained by inducing differentiation of liver progenitor cells without separation using CPM-positivity as the marker.

Example 3

(1) Inducing Differentiation from Human Liver Progenitor Cells to Human Cholangiocytes The three-dimensional gel culturing method described in Tanimizu et al., Mol Biol Cell, 2007, 18(4), 1472-1479 and Yanagida et al., PloS ONE 8, e67541 was slightly modified for inducing differentiation to human cholangiocytes. After proliferating CPM-positive cells according to Example 1(2), the cells were collected and resuspended in gel composed of a 2:3 mixture of growth factor reduced Matrigel (Corning) and collagen type I (Nitta Gelatin), to a density of $1 \times 10^5$ cell/50 µl. The cell suspension was then added to a 24-well plate (Corning) and incubated at 37° C. for 2 hours until solid. The cells were then cultured for 7 days in the presence of R-spondin-1 (40 ng/ml) and WNT-3a (40 ng/ml) (Pepro-Tech), to induce differentiation to human cholangiocytes. The human cholangiocytes formed a cyst.

(2) Expression of Cell Markers

Figure 9:
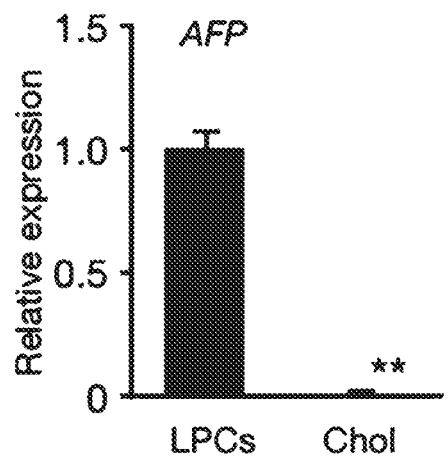
FIG. 9 shows the results of analysis using quantitative RT-PCR, for AFP mRNA expression in liver progenitor cells separated using the CPM-positive marker, and human cholangiocytes differentiated from liver progenitor cells. The label "LPCs" refers to liver progenitor cells prepared by the method of the invention, and the label "Chol" refers to human cholangiocytes differentiated from liver progenitor cells. The results are expressed as mean±SEM for four independent experiments. **$p<0.01$.
Figure 10:
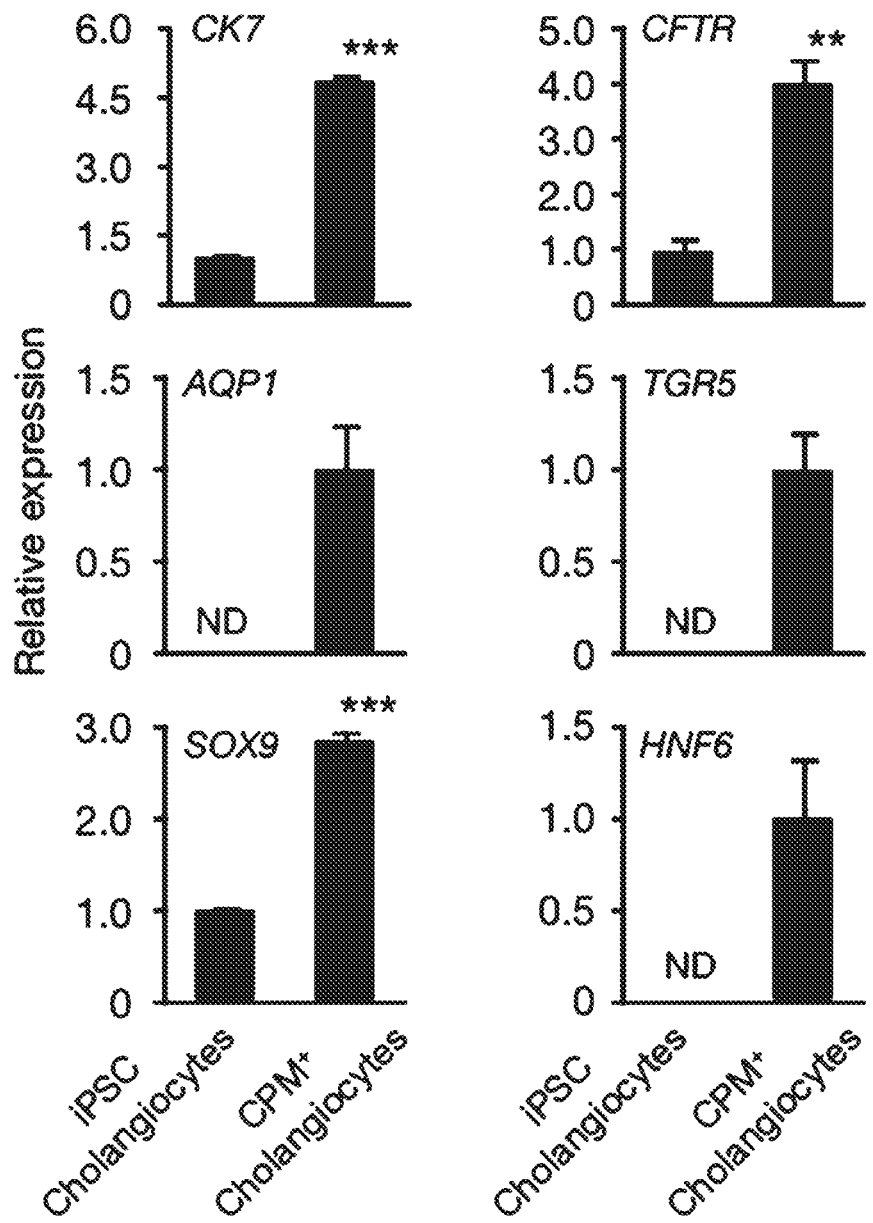
FIG. 10 shows the results of analysis using quantitative RT-PCR, for mRNA expression of cholangiocyte-specific markers in human cholangiocytes obtained by inducing differentiation of liver progenitor cells separated using the CPM-positive marker, and human cholangiocytes obtained by inducing differentiation of liver progenitor cells without separation using the CPM-positive marker. The label "CPM+Cholangiocytes" in the graphs refers to liver progenitor cells obtained by inducing differentiation of liver progenitor cells separated off using the CPM-positive marker, and the label "iPSC Cholangiocytes" in the graphs refers to human cholangiocytes obtained by inducing differentiation of liver progenitor cells without separation using the CPM-positive marker. The results are expressed as mean±SEM for four independent experiments. ND: Not detected, $p<0.01$, *$p<0.001$.

The expression level of AFP, a hepatocyte precursor marker, decreased in the obtained human cholangiocytes (FIG. 9). On the other hand, expression of the cholangiocyte-specific marker was confirmed (FIG. 10). Cholangiocyte marker mRNA expression in human cholangiocytes obtained by inducing differentiation of liver progenitor cells without separation using CPM-positivity as the marker, and human cholangiocytes prepared in (1) above, was analyzed using quantitative RT-PCR (FIG. 10). The human cholangiocytes obtained in (1) above exhibited higher expression of the cholangiocyte markers CK7, CFTR, AQP1, TGRS, SOX9 and HNF6 compared to the human cholangiocytes obtained by inducing differentiation of liver progenitor cells without separation using CPM-positivity as the marker.

Example 4

Preparation of Human Liver Sinusoidal Progenitor Cells (1) Inducing Differentiation from Human iPS Cells to Human Mesodermal Cells Human iPS cells (454E2, RIKEN Cell Bank) were cultured with mitomycin C-treated mouse embryo fibroblasts (MEF) as feeder cells. The MEF were prepared from embryonic mice (ICR mice, product of Japan SLC, Inc.). Before the start of differentiation inducement, the human iPS cells were reseeded in a gelatin-coated dish and incubated for 30 minutes to remove the MEF. In order to induce differentiation from human iPS cells to mesoderm, embryoid body formation culturing was carried out on an Ultra-Low Attachment plate (Corning). The embryoid body formation culturing was carried out with Stempro-34 SFM (Life Technologies) as the basal medium, adding 10 µM Y27632 (Wako Pure Chemical Industries, Ltd.) and 2 ng/ml BMP4 (Life Technologies) from day 0 to day 1 after starting inducement, adding 5 ng/ml activin A (Pepro Tech, New Jersey, US) and 5 ng/ml bFGF (Life Technologies) and 30 ng/ml BMP4 (Life Technologies) from day 1 to day 4 after starting inducement, and adding 10 ng/ml VEGF (Pepro Tech), 5.4 µM SB431542 (Tocris, Bristol, UK) and 0.5 µM dorsomorphin (Tocris) from day 4 to day 6 after starting inducement. Culturing was carried out for 6 days to induce differentiation to mesodermal cells.

(2) Inducing Differentiation from Human Mesodermal Cells to Human Liver Sinusoidal Endothelial Progenitor Cells The embryoid body obtained in (1) was transferred to a plate precoated with gelatin, and cultured for 7 days in endothelial cell medium comprising 50 ng/ml VEGF added to EGM-2 (Lonza, Basel, Switzerland). The CD31-positive, FLK1-positive and CD34-positive human liver sinusoidal endothelial progenitor cells were separated with a MoFlo XDP cell sorter (Beckman Coulter, Inc). All of the differentiation was induced in an environment of 5% $CO_2$, 4% $O_2$.

(3) Marker Molecule Expression Analysis at Different Differentiation Stages

Figure 11:
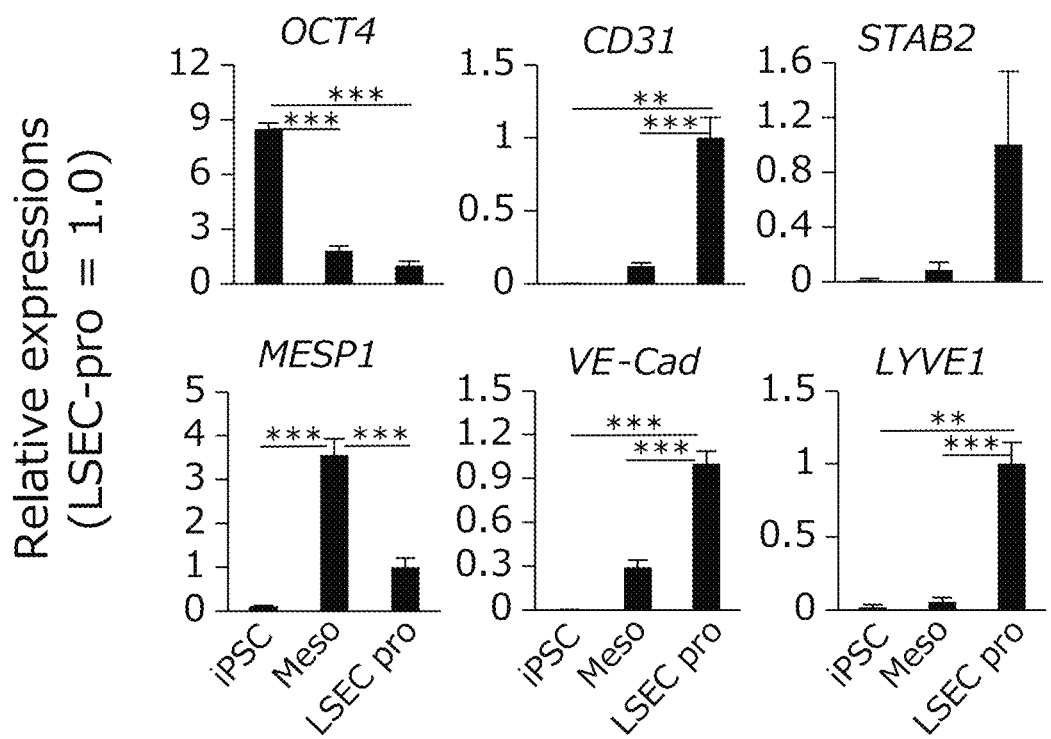
FIG. 11 shows gene expression levels of marker molecules, for human iPS cells (iPSC), human mesodermal cells (Meso) and human liver sinusoidal endothelial progenitor cells (LSEC pro) (before cell separation). n=3, 3, 5, $p<0.01$, *$p<0.001$.

The gene expression levels of marker molecules in the human iPS cells, the human mesodermal cells that had been induced in (1) above and the human liver sinusoidal endothelial progenitor cells induced in (2) above (before cell separation) were analyzed by quantitative RT-PCR. The results are shown in FIG. 11. The undifferentiated marker OCT4 was highly expressed in iPS cells, and decreased as differentiation progressed. The mesoderm marker MESP1 was expressed most highly at the differentiation stage of the mesodermal cells. The vascular endothelial cell marker molecules CD31 and VE-cadherin (VE-Cad) were highly expressed at the liver sinusoidal endothelial progenitor cell stage. The liver sinusoidal endothelial progenitor cell marker molecules STAB2 and LYVE1 were also highly expressed at the liver sinusoidal endothelial progenitor cell stage (FIG. 11). These results suggested that the induced cells included cells having the features of liver sinusoidal endothelial progenitor cells.

(4) Marker Molecule Expression Analysis at Different Differentiation Stages

Figure 13:
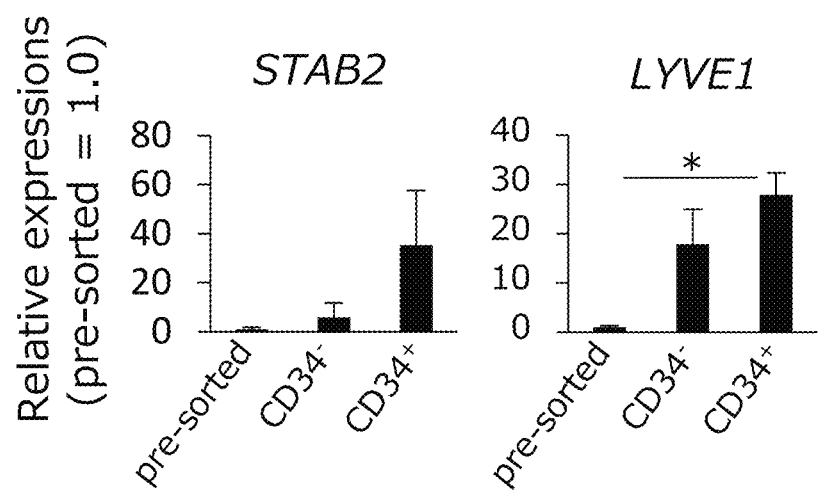
FIG. 13 shows expression levels of marker molecules (STAB2 and LYVE1) in human liver sinusoidal endothelial progenitor cells, for a cell group comprising human liver sinusoidal endothelial progenitor cells obtained by inducing differentiation of human mesodermal cells (pre-sorted), and $FLK1^+CD31^+CD34^+$ cells ($CD34^+$) and $FLK1^+CD31^+CD34^-$ cells (CD34), separated from the pre-sorted group. n=3, mean±SEM. *$p<0.05$, ***$p<0.001$.

The expression levels of human liver sinusoidal endothelial progenitor cell marker molecules (STAB2 and LYVE1) were analyzed by quantitative RT-PCR, for a cell group including human liver sinusoidal endothelial progenitor cells differentiated from human mesodermal cells (pre-sorted), and $FLK1^+CD31^+CD34^+$ cells ($CD34^+$) and $FLK1^+CD31^+CD34^-$ cells (CD34), separated from the pre-sorted group. The results are shown in FIG. 13. The $CD34^+$ cell group had higher expression of the liver sinusoidal endothelial progenitor cell marker molecules STAB2 and LYVE1 than the $CD34^-$ cell group. The results demonstrated that the $FLK1^+CD31^+CD34^+$ phenotype combination can be utilized as a marker for separating human liver sinusoidal endothelial progenitor cells.

Figure 14:
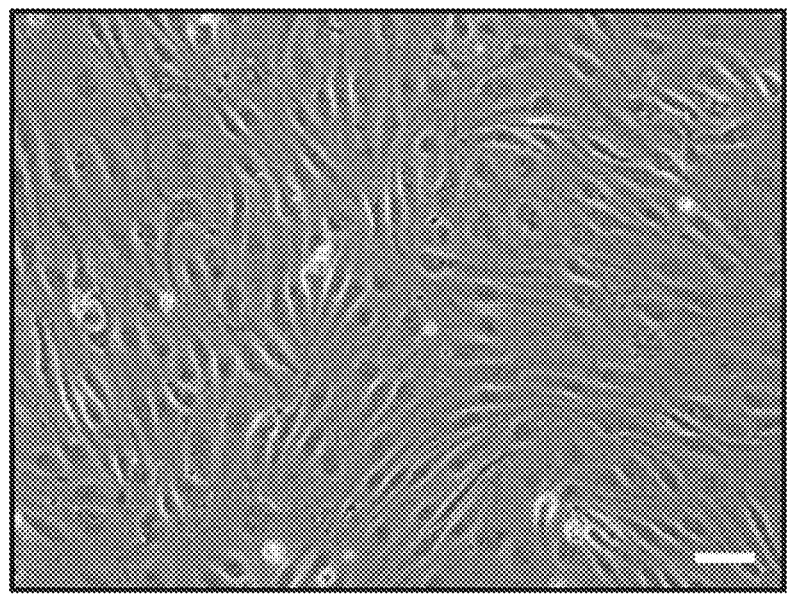
FIG. 14 shows a phase contrast microscope image of $FLK1^+CD31^+CD34^+$ human liver sinusoidal endothelial progenitor cells. Scale bar: 100 μm.
Figure 15:
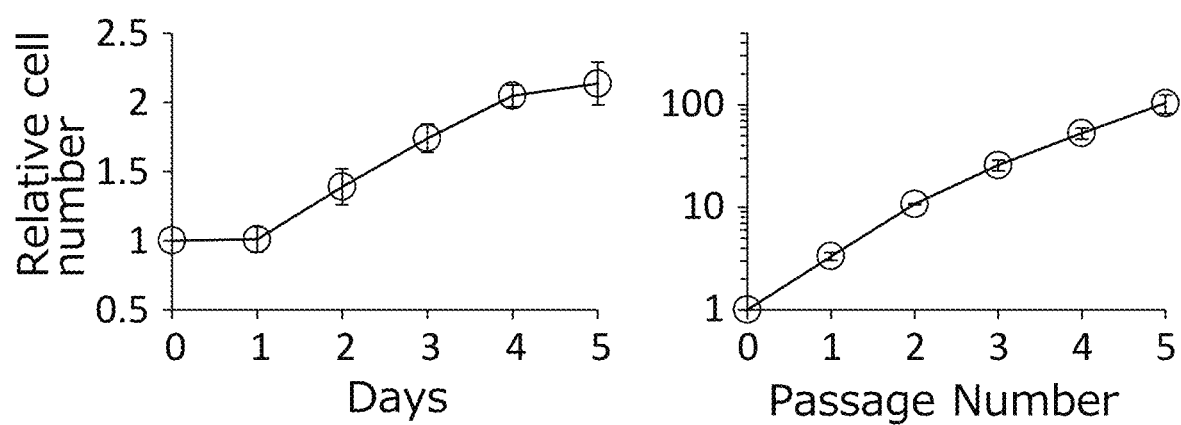
FIG. 15 shows proliferation of $FLK1^+CD31^+CD34^+$ human liver sinusoidal endothelial progenitor cells (left) and the results after subculturing (right). n=3. mean±SEM.
Figure 16:
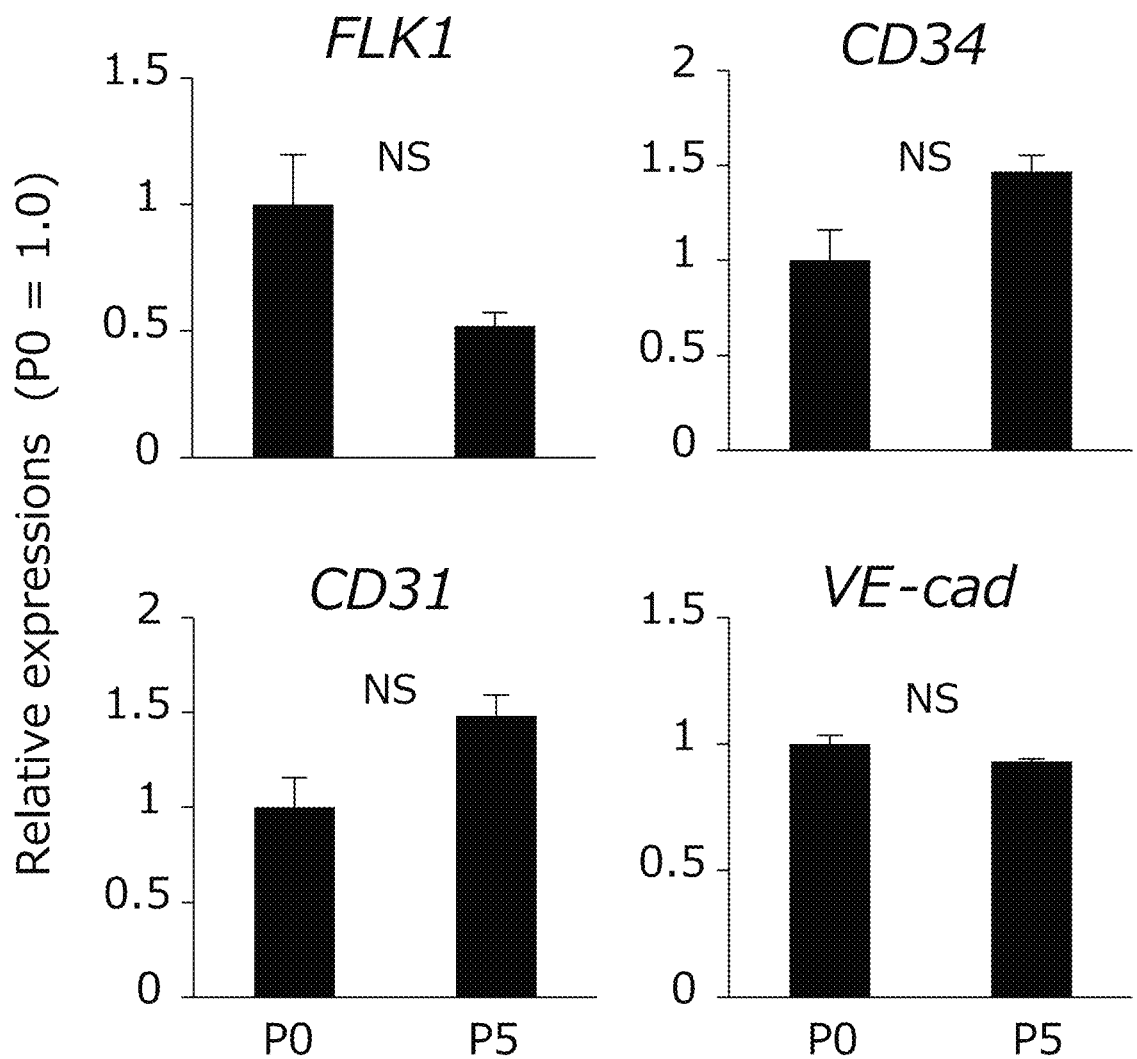
FIG. 16 shows expression levels of liver sinusoidal endothelial progenitor cell marker molecules in $FLK1^+CD31^+CD34^+$ cells after 5 subcultures. P0: 0 subcultures, P5: 5 subcultures. n=3. mean±SEM. NS: No significant difference.
Figure 17:
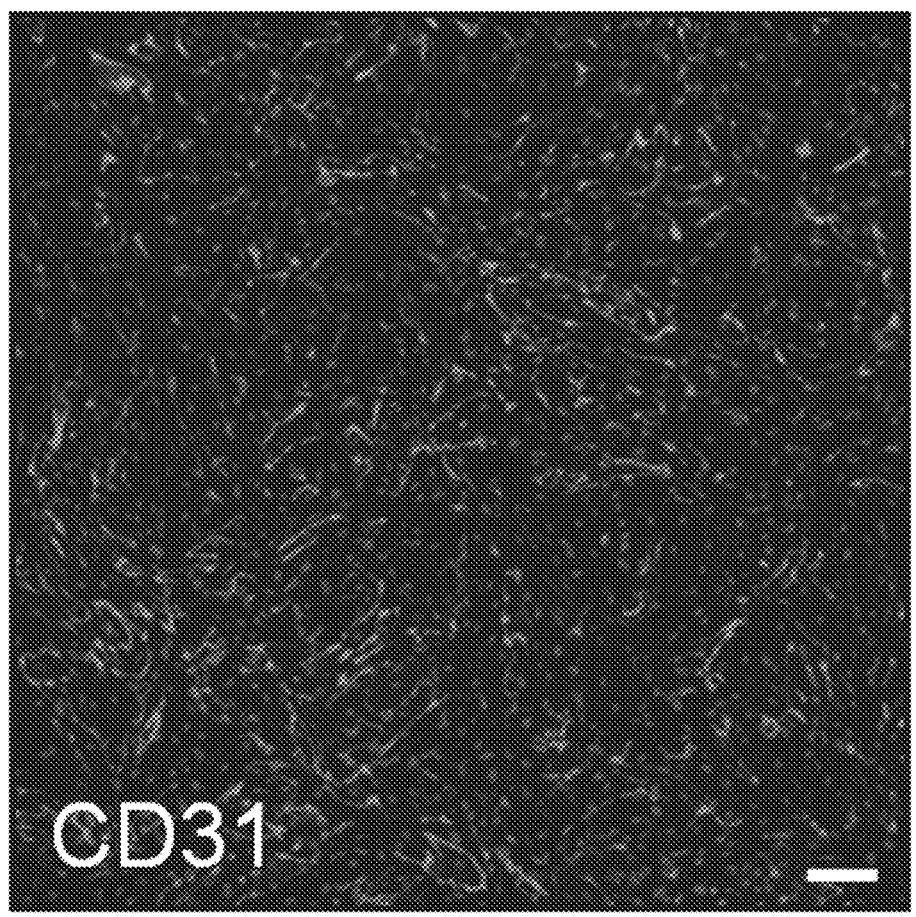
FIG. 17 shows an immunocytochemical staining image of $FLK1^+CD31^+CD34^+$ cells after cryopreservation. Blue: nuclei, Red: CD31. Scale bar: 100 μm.

(5) Proliferation Potency of Human Liver Sinusoidal Endothelial Progenitor Cells The $FLK1^+CD31^+CD34^+$ cells separated in Example 4(2) above were seeded in a fibronectin-coated plate to 15,000 cells/cm$^2$ and cultured in endothelial cell medium. The $FLK1^+CD31^+CD34^+$ cells maintained their endothelial cell forms (FIG. 14), had high proliferation potency (FIG. 15, top), and were also able to be subcultured several times (FIG. 15, bottom). The cell count was calculated using a hemocytometer, after dissociating the cells using 0.05% trypsin/0.5 mM EDTA. In addition, quantitative RT-PCR showed that the cells maintained their liver sinusoidal endothelial progenitor cell marker molecule expression even after 5 subcultures (FIG. 16). Prolonged cryopreservation was also possible, and CD31 was homogeneously expressed even after 30 days of cryopreservation (FIG. 17).

Example 5

(1) Preparation of Human Liver Sinusoidal Endothelial Cells

The human liver sinusoidal endothelial progenitor cells separated in Example 4(2) above were reseeded onto a fibronectin-coated plate to a density of 20,000 cells/cm$^2$, and cultured for 14 days in human liver sinusoidal endothelial cell-inducing medium comprising 50 ng/ml VEGF and the TGF-β inhibitor 1.5 µm A83-01 (Tocris) added to EGM-2 (Lonza, Basel, Switzerland), to obtain a cell fraction containing human liver sinusoidal endothelial cells. All of the differentiation was induced in an environment of 5% $CO_2$, 4% $O_2$. In order to induce mature liver sinusoidal endothelial cells with high efficiency, a MoFlo XDP cell sorter (Beckman Coulter, Inc) was subsequently used to separate CD31-positive, FcRγII-positive cells from this cell fraction.

(2) Marker Molecule Expression Analysis

Figure 18:
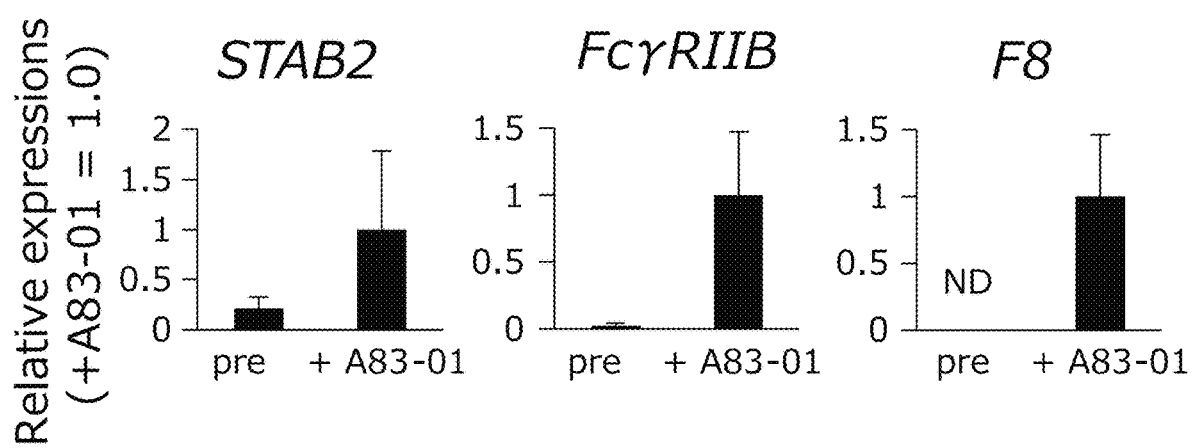
FIG. 18 shows expression levels of liver sinusoidal endothelial cell markers in $FLK1^+CD31^+CD34^+$ human liver sinusoidal endothelial progenitor cells and human liver sinusoidal endothelial cells induced from the precursor cells. In the graphs, "pre" represents the human liver sinusoidal endothelial progenitor cells. In the graphs, "+A83-01" represents the human liver sinusoidal endothelial cells. The label "F8" in the graphs indicates factor VIII. n=3, mean±SEM.
Figure 19:
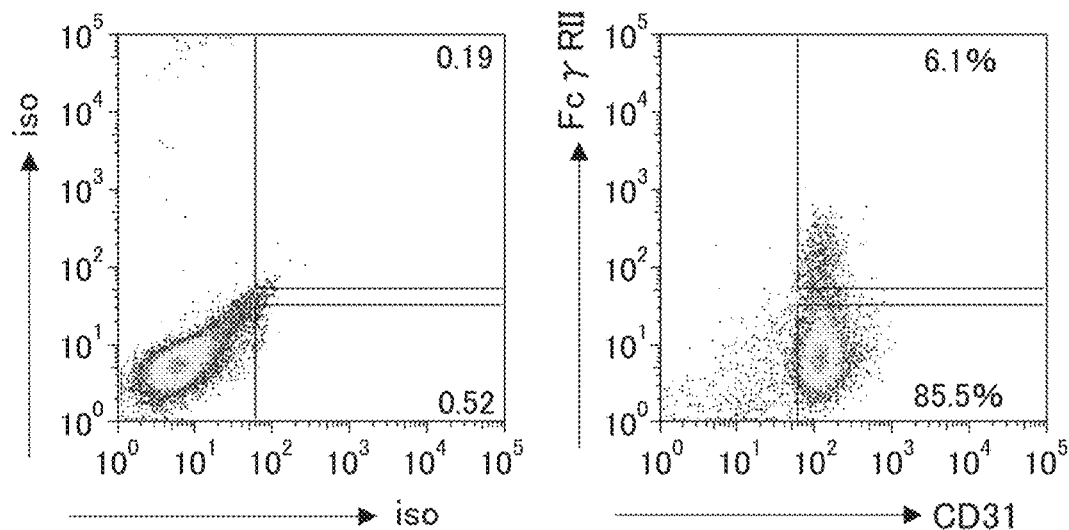
FIG. 19 shows the results of flow cytometry analysis of a cell fraction that includes human liver sinusoidal endothelial cells induced from human liver sinusoidal endothelial progenitor cells.

The expression levels of liver sinusoidal endothelial cells markers were analyzed by quantitative RT-PCR in the human liver sinusoidal endothelial progenitor cells separated in Example 4(2) above, and the human liver sinusoidal endothelial cells prepared in Example 5(1) (before separation). The results are shown in FIG. 18. Addition of a TGF-β inhibitor promoted expression of the liver sinusoidal endothelial cell markers STAB2, FcRγIIB and F8.

(3) Properties of Human Liver Sinusoidal Endothelial Cells

Figure 20:
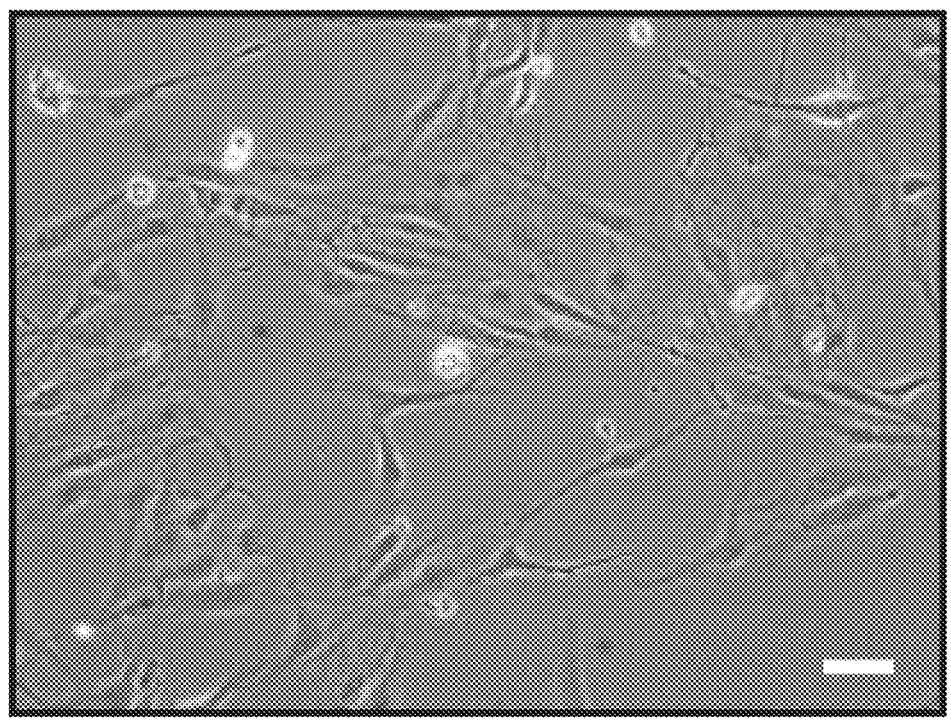
FIG. 20 shows a phase contrast microscope image of CD31-positive, FcRγII-positive cells. Scale bar: 100 μm.
Figure 21:
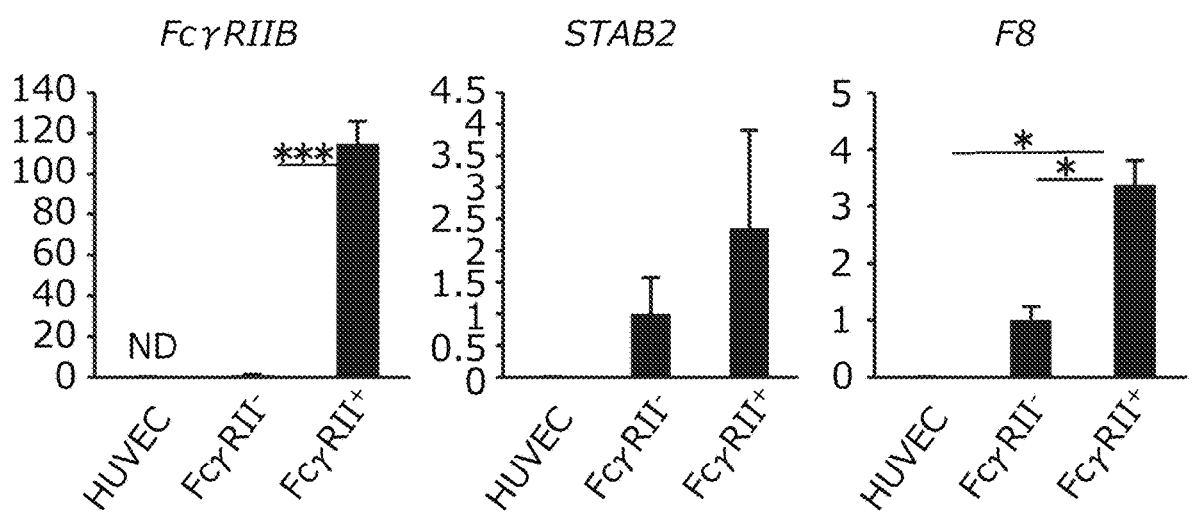
FIG. 21 shows expression analysis of human liver sinusoidal endothelial cell marker molecules in CD31$^+$FcRγII$^-$ cells and CD31$^+$FcRγII$^+$ cells. Human umbilical vein epithelial cells (HUVEC) were used as a control. n=3. mean±SEM. ND: Not detected. *p<0.05, p<0.01, *p<0.001.

The CD31-positive, FcRγII-positive liver sinusoidal endothelial cells separated in Example 5(1) above exhibited an endothelial cell-like morphology (FIG. 20). In addition, the CD31-positive, FcRγII-positive cells had higher expression of STAB2, FcRγIIB and blood dotting factor VIII (factor VIII), compared to the CD31-positive, FcRγII-negative cells and HUVEC (FIG. 21).

(4) Uptake of Acetylated LDL and Hyaluronic Acid

Figure 22:
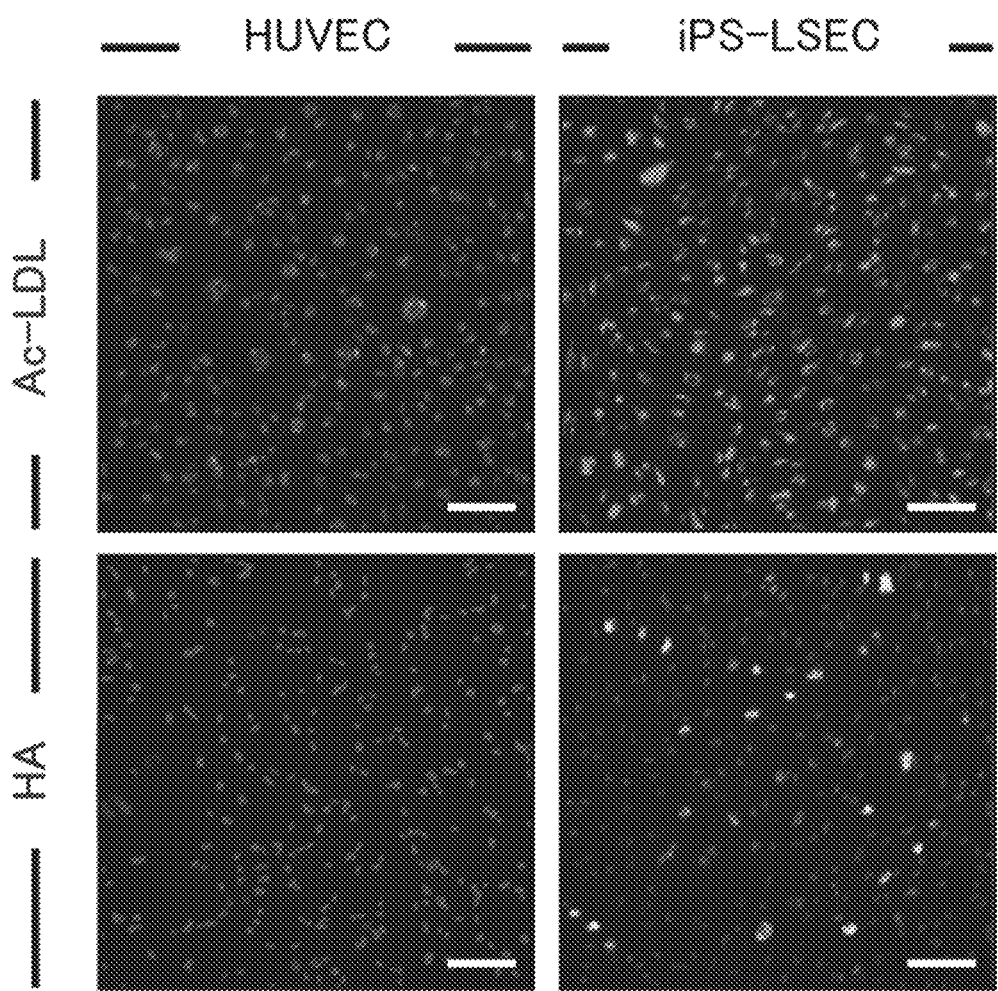
FIG. 22 is an immunocytochemical staining image showing acetylated LDL (Ac-LDL) and hyaluronic acid (HA) uptake by human iPS cell-derived CD31-positive, FcRγII-positive liver sinusoidal endothelial cells (iPS-LSEC). HUVEC were used as a control. Blue: nuclei, red: acetylated LDL, green: hyaluronic acid, scale bar: 100 μm.

To culturing medium containing CD31-positive, FcRγII-positive liver sinusoidal endothelial cells there was added 5 µg/ml DiI-Ac-LDL (AlfaAesar, Massachusetts, US) or 25 µg/ml fluoresceinamine-labeled sodium hyaluronate (FAHA-L1) (PG Research, Tokyo, Japan), and the cells were incubated at 30° C. for 4 hours. After 4 hours, the cells were rinsed with PBS and contrast stained with Hoechst33342. The results are shown in FIG. 22 and FIG. 23. The uptake of acetylated LDL by the liver sinusoidal endothelial cells was equivalent to HUVEC, but uptake of hyaluronic acid via STAB2 was confirmed only in the liver sinusoidal endothelial cells.

(5) Expression of Factor VIII

Expression of factor VIII on the protein level was found by immunocytochemical staining and flow cytometry analysis (FIGS. 24 and 25).

Example 6

Preparation of Human Hepatic Stellate Progenitor Cells

Figure 27:
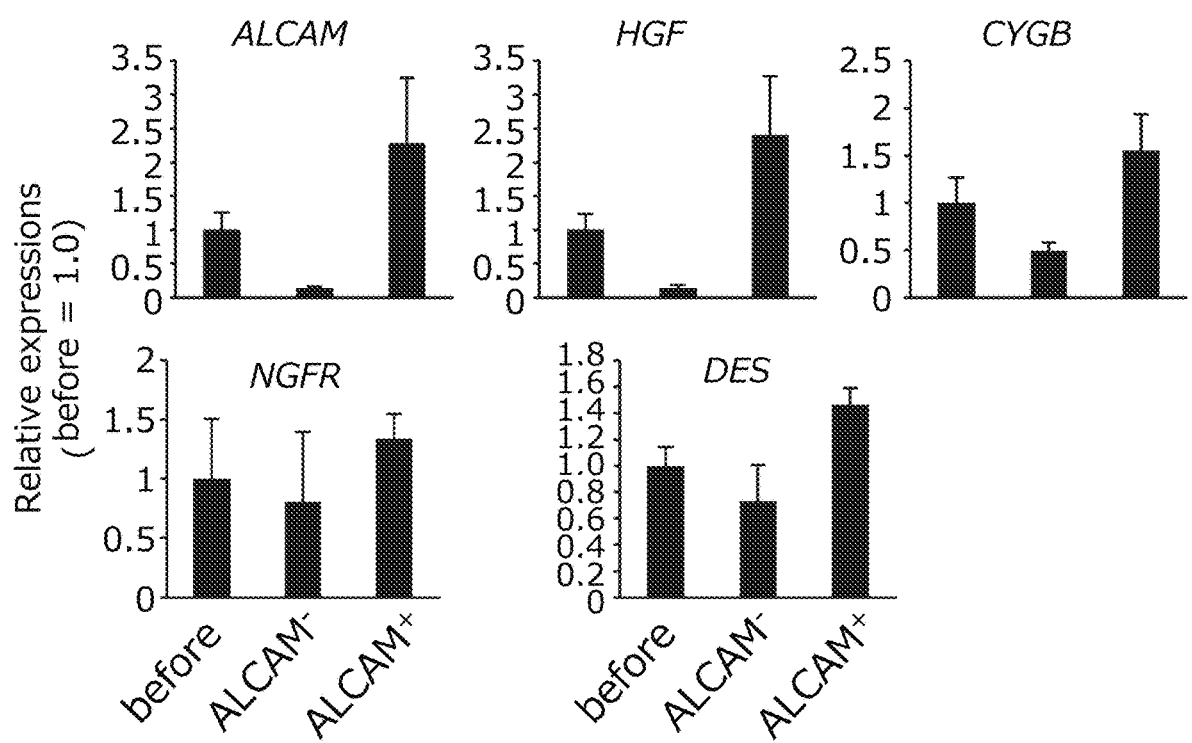
FIG. 27 shows expression levels of hepatic stellate progenitor cell marker molecules before separation of iPS cell-derived mesodermal cells (before), and for ALCAM-positive cells (ALCAM$^+$) and ALCAM negative cells (ALCAM$^-$). n=3. mean±SEM.

Human mesodermal cells were differentiated from human iPS cells by the same procedure as described in Example 4(1). The human hepatic stellate progenitor cells in the mesodermal cell cluster were separated into ALCAM-positive cells (human hepatic stellate progenitor cells) and ALCAM-negative cells with a MoFlo XDP cell sorter (Beckman Coulter, Inc), with ALCAM-positivity as the marker. The expression levels of hepatic stellate progenitor cell marker molecules in the ALCAM-positive cells and ALCAM-negative cells before separation of the iPS cell-derived mesodermal cells were analyzed by quantitative RT-PCR. The results are shown in FIG. 27. The ALCAM-positive cells had higher expression of the hepatic stellate progenitor cell-specific marker molecules HGF, CYGB, NGFR and desmin (DES), compared to the ALCAM-negative cells.

Example 7

(1) Preparation of Human Hepatic Stellate Cells

A plate coated with cell matrix TypeI-C(Nitta Gelatin, Osaka, Japan) was seeded with the human hepatic stellate progenitor cells prepared in Example 6 at a density of 15,000 cells/cm$^2$, and cultured for 5 days in hepatic stellate cell-inducing medium comprising ROCK inhibitor 10 µM Y27632 added to MSCGM (Lonza), to induce differentiation and obtain human hepatic stellate cells. The differentiation was induced in an environment of 5% $CO_2$, 20% 02.

(2) Marker Molecule Expression Analysis

Figure 28:
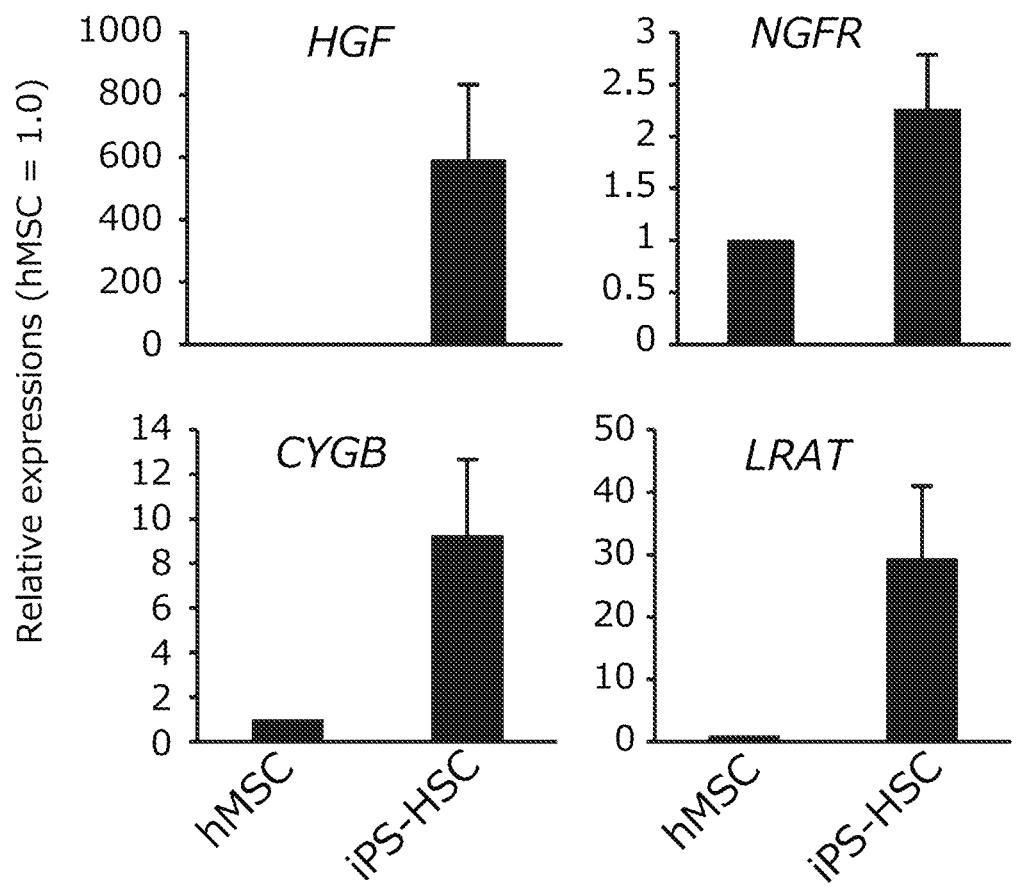
FIG. 28 shows the results of expression analysis of hepatic stellate cell marker molecules for human iPS cell-derived human hepatic stellate cells (iPS-HSC). Human bone marrow-derived mesenchymal stem cells (hMSC) were used as a control. n=3. mean±SEM.

The expression levels of hepatic stellate cell marker molecules in the human iPS cell-derived hepatic stellate cells prepared in Example 7(1) above were analyzed by quantitative RT-PCR. The results are shown in FIG. 28. The human iPS cell-derived hepatic stellate cells had higher expression of HGF, NGFR, CYGB and LRAT, which are specifically expressed by hepatic stellate cells, compared to human bone marrow-derived mesenchymal stem cells (hMSC).

(3) Uptake of Vitamin A

Figure 29:
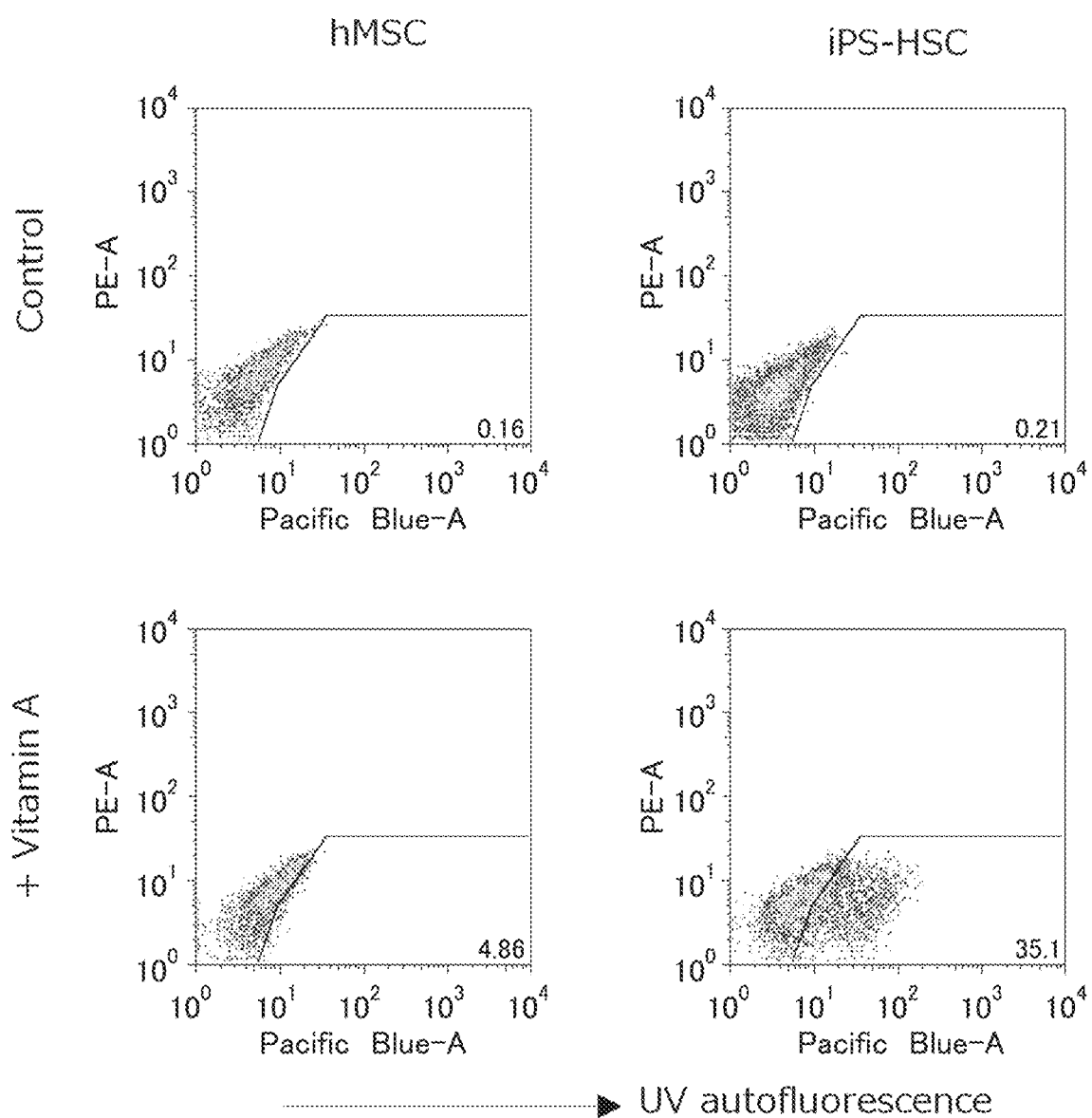
FIG. 29 shows the results of flow cytometry analysis of human iPS cell-derived human hepatic stellate cells (iPS-HSC) and human bone marrow-derived mesenchymal stem cells (hMSC). Intracellular vitamin A was detected by autologous fluorescence.

Hepatic stellate cells are known to take up and store vitamin A intracellularly. Vitamin A was therefore added to the medium and the uptake was analyzed. Vitamin A (retinoid (Sigma-Aldrich Corporation, St. Louis, US)) was added in an amount of 10 µM to the human iPS cell-derived hepatic stellate cell culturing system. The cells were separated using 0.05% trypsin/0.5 mM EDTA, and a CantoII (BD Biosciences) was used to detect autologous fluorescence of vitamin A in the cells by flow cytometry. hMSC were used as a control. Autologous fluorescence was detected only in the human iPS cell-derived hepatic stellate cells, confirming intracellular uptake of vitamin A (FIG. 29).

Figure 30:
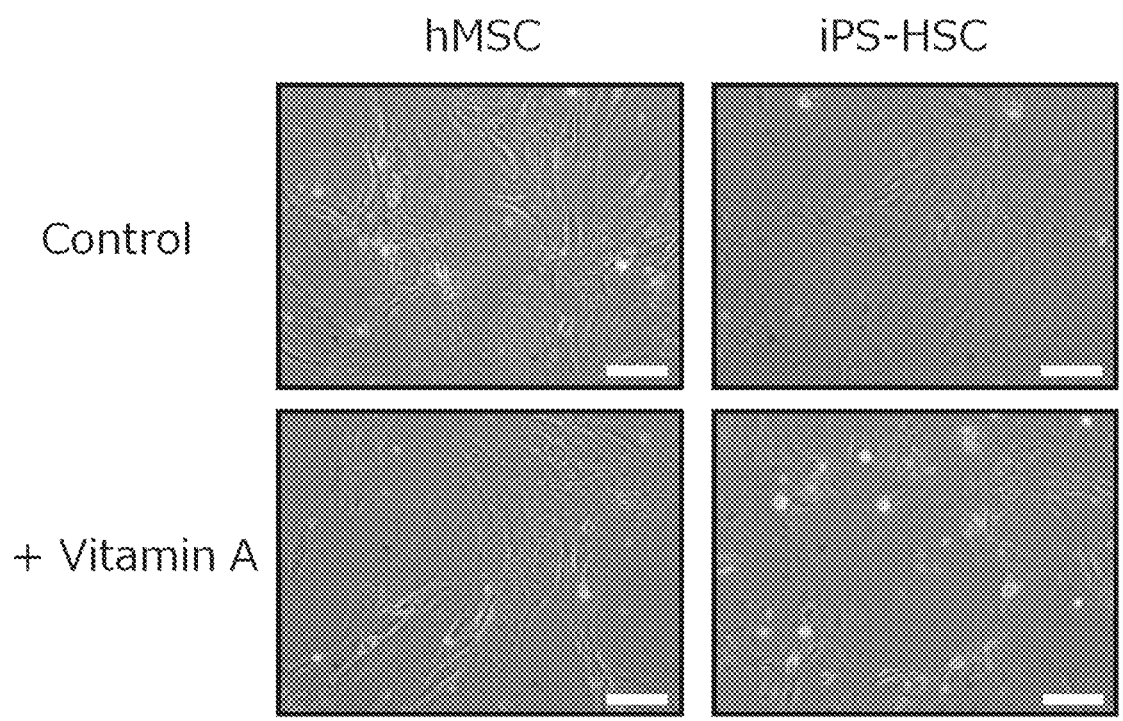
FIG. 30 shows a phase contrast microscope image of human iPS cell-derived human hepatic stellate cells (iPS-HSC) and human bone marrow-derived mesenchymal stem cells (hMSC) after addition of vitamin A. Scale bar: 100 μm.

In addition, based on a phase contrast microscope image, more fat droplets were confirmed in the human iPS cell-derived hepatic stellate cells prepared in Example 7(1) above, compared to the hMSC (FIG. 30).

Example 8

Preparation of Human Liver Cellular Tissue Model (Co-Culturing of Human Hepatic Non-Parenchymal Cells and Human Liver Progenitor Cells)

The human liver sinusoidal endothelial cells prepared in Example 5 and the human hepatic stellate cells prepared in Example 7 were seeded on a plate coated with cell matrix Type I-C(Nitta Gelatin, Osaka, Japan) until confluent, to create feeder cells. The feeder cells were treated with mitomycin C on the following day. As a control for the feeder cells there were used human umbilical vein endothelial cells (HUVEC, obtained from Lonza) and human bone marrow-derived mesenchymal stem cells (hMSC, obtained from Lonza). The liver progenitor cells prepared in Example 1 were seeded in the feeder cells and co-cultured for 10 days.

Figure 31:
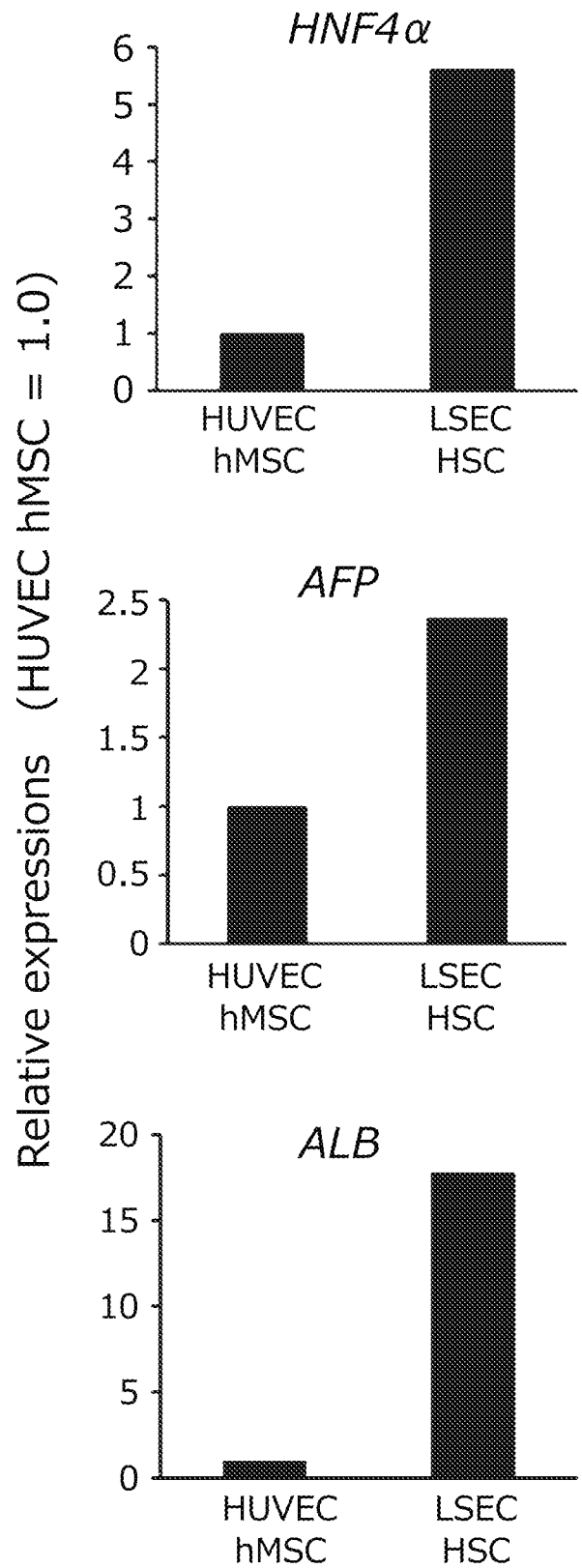
FIG. 31 shows expression of a liver progenitor cell marker (LSEC HSC), when co-culturing with human iPS cell-derived CPM$^+$ liver progenitor cells, using human iPS cell-derived liver sinusoidal endothelial cells and human iPS cell-derived hepatic stellate cells as feeder cells. As a control, HUVEC and hMSC were used as feeder cells (HUVEC hMSC). n=1.

Compared to using HUVEC and hMSC as feeder cells, using the human iPS cell-derived liver sinusoidal endothelial cells and hepatic stellate cells as feeder cells augmented expression of HNF4α, AFP and ALB as hepatocyte precursor markers and hepatocyte markers (FIG. 31). This suggested that established human iPS cell-derived liver sinusoidal endothelial cells and hepatic stellate cells support proliferation and differentiation potency of liver progenitor cells.

Example 9

Preparation of Human Liver Cellular Tissue Model (Co-Culturing of Mouse Hepatic Non-Parenchymal Cells and Human Liver Progenitor Cells)
(1) Digestion and Hemolysis of Mouse Embryo Liver Liver was surgically extracted from a 14.5-day-old mouse embryo (C57BL/6 mouse, Japan SLC, Inc.) using small scissors and forceps. The extracted liver tissue was minced with small scissors. The liver tissue was transferred to 10 to 20 ml of LPM (Thermo Fisher Scientific) and allowed to stand for 5 minutes in a warm bath at 37° C. The liquid was then replaced with Liver Digest Medium (Thermo Fisher Scientific), and stirring was conducted for 5 minutes in a warm bath at 37° C. Next, a disposable pipette was used to mechanically digest the liver tissue by pipetting. After centrifugal separation at 1800 rpm for 3 minutes and removal of the supernatant, it was suspended in DMEM containing 10% FBS. The cell suspension was passed through a 70 µm cell strainer, and after centrifugal separation at 1800 rpm for 3 minutes and removal of the supernatant, the obtained cells were suspended in a 5 ml ammonium chloride solution, reacted at 4° C. for 6 minutes, and subjected to hemolysis treatment. DMEM containing 10% FBS was then added, the mixture was passed through a 70 µm cell strainer, and after centrifugal separation at 1800 rpm for 3 minutes and removal of the supernatant, the cells were collected.
(2) Separation of Mouse Embryo Hepatic Non-Parenchymal Cells Hemolysis-treated cells were suspended in 1% BSA/PBS, mouse FcR (antibody (1:100 dilution)) was added, and the mixture was blocked at 4° C. for 15 minutes. Next, primary antibody (1:100 dilution) was reacted for 30 minutes. The primary antibody was biotin-labeled or FITC-labeled Stab2 antibody, biotin-labeled Msln antibody or APC-labeled p75NTR antibody. After removal of the primary antibody with 1% BSA/PBS, secondary antibody (1:100 dilution) was reacted for 20 minutes in the same manner. The secondary antibody was SA-APC antibody or SA-PE antibody. After removal of the secondary antibody with 1% BSA/PBS, reaction was conducted for 10 minutes with magnetic beads (Miltenyi Biotec K.K.) diluted 20-fold with MACS Running Buffer (Miltenyi Biotec K.K.). Next, auto MACS (Miltenyi Biotec K.K.) was used for magnetic cell separation. For separation of single cells, further separation was carried out using Moflo (Beckman Coulter).
(3) Culturing of Mouse Embryo Hepatic Non-Parenchymal Cells The separated mouse embryo hepatic non-parenchymal cells were cultured in a plate on collagen Type IC (Nitta Gelatin) and collagen Type IA (Nitta Gelatin), with EGM+MSC (1:1, LONZA) containing 2% B27 (Life Technology), 50 ng/ml rhVEGF (Peprotech), 10 µg/ml Y27632 (Wako) and 0.5 µM A83-01 (Tocris), under conditions of 37° C., 5% $CO_2$, 95% humidity.
(4) Culturing of Mouse Liver Sinusoidal Endothelial Cells Seeding was carried out in a plate on collagen Type IC (Nitta Gelatin) and collagen Type IA (Nitta Gelatin). The medium used was EGM (LONZA) with addition of 50 ng/ml rhVEGF (Peprotech), 10 µg/ml Y27632 (Wako) and 0.5 µM A83-01 (Tocris). Culturing was carried out under conditions of 37° C., 5% $CO_2$, 95% humidity.
(5) Culturing of Mouse Hepatic Stellate Cells Seeding was carried out in a plate on collagen Type IC (Nitta Gelatin) and collagen Type IA (Nitta Gelatin). The medium used was EGM+MSC (1:1, LONZA) with addition of 2% B27 (Life Technology), 50 ng/ml rhVEGF (Peprotech), 10 µg/ml Y27632 (Wako) and 0.5 µM A83-01 (Tocris). Culturing was carried out under conditions of 37° C., 5% $CO_2$, 95% humidity.
(6) Culturing of Mouse Liver Mesothelial Cells Seeding was carried out in a plate on collagen Type IV (Nitta Gelatin) and collagen Type IA (Nitta Gelatin). The medium used as αMEM, with addition of 10% FBS, 50 nmol/L mercaptoethanol, 10 ng/ml oncostatin M (OSM) (Peprotech) and 10 ng/ml bFGF (Peprotech). Culturing was carried out under conditions of 37° C., 5% $CO_2$, 95% humidity. Medium exchange was carried out every other day.
(7) Co-Culturing (Plate Culture)

Collagen 1 Gel (Nitta Gelatin) was added at 200 µl to each well of a 48-well plate, and gelling was carried out in an incubator for 30 minutes. After seeding the mouse-derived non-parenchymal cells of Example 9(3) above in the gel and culturing, they were used as feeder cells for co-culturing together with the liver progenitor cells prepared in Example 1, in maintenance medium in which liver progenitor cells can be maintained and proliferated, and in differentiation medium in which the liver progenitor cells can be induced to mature hepatocytes. DMEM-F12 medium used for culturing of the liver progenitor cells in Example 1(2) was used as the maintenance medium. The differentiation medium used was an HCM SingleQuots Kit with addition of 20 ng/ml rhOSM (Peprotech), 1% ITS premix (Life Technology), 0.5 µM dexamethasone and 0.5 µM A83-01 (Tocris) (LONZA, but without addition of rhEGF). The liver progenitor cells were also cultured alone in maintenance medium and differentiation medium.

Figure 32:
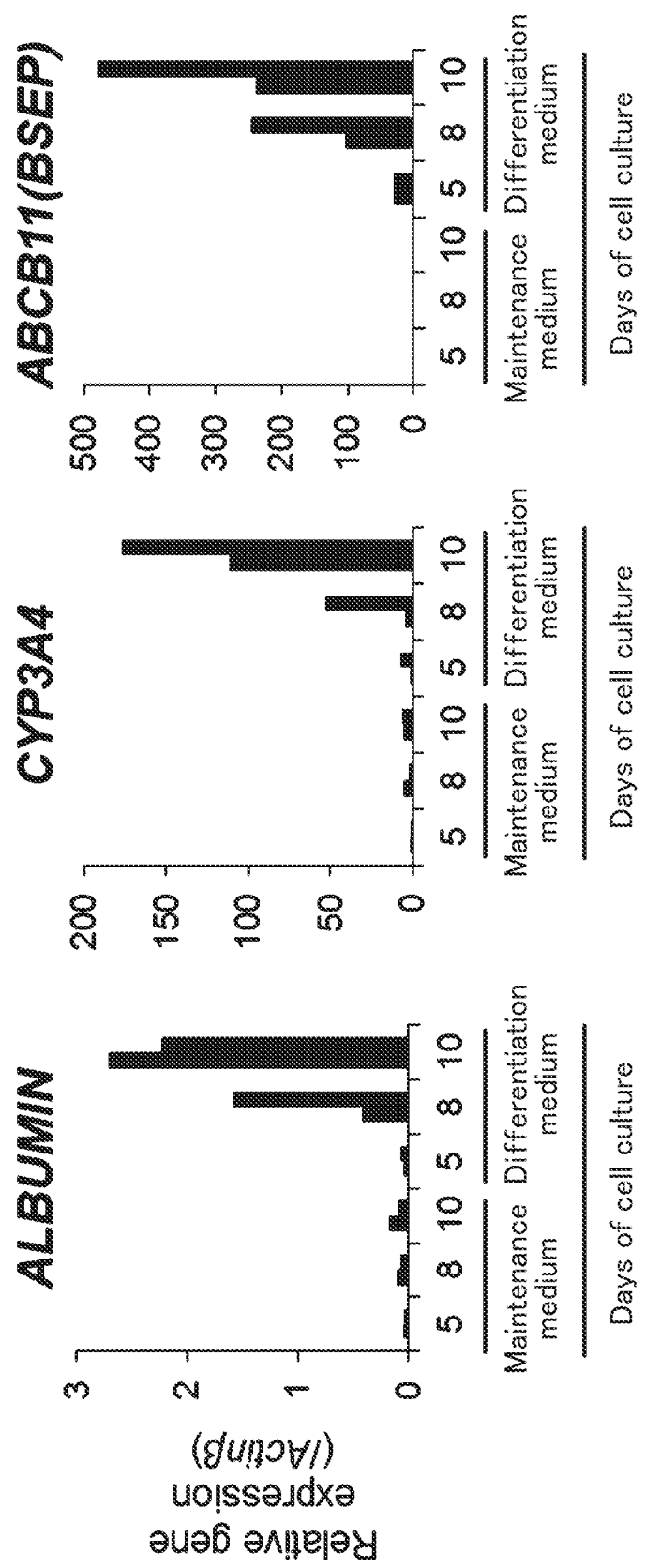
FIG. 32 shows the results of analyzing expression of genes associated with hepatocyte differentiation, when co-culturing human iPS cell-derived liver sinusoidal endothelial cells with mouse-derived non-parenchymal cells. The left-side bar represents the results for culturing iPS cell-derived liver progenitor cells alone, and the right-side bar represents the results for co-culturing human iPS cell-derived liver progenitor cells and mouse-derived non-parenchymal cells.

Expressions of genes involved in hepatocyte differentiation were analyzed by quantitative RT-PCR (FIG. 32). Specifically, expression levels of ALB which is a protein secreted by hepatocytes, CYP3A4 which is an enzyme involved in drug metabolism, and the ABC transporter ABCB11 which is involved in excretion of bile acid (Bile Salt Export Pump), were compared. Each hepatocyte marker had no change in expression level when culturing in the maintenance medium, but when culturing in the differentiation medium, increased expression was confirmed, with the highest expression level being exhibited when co-culturing with non-parenchymal cells.

Figure 33:
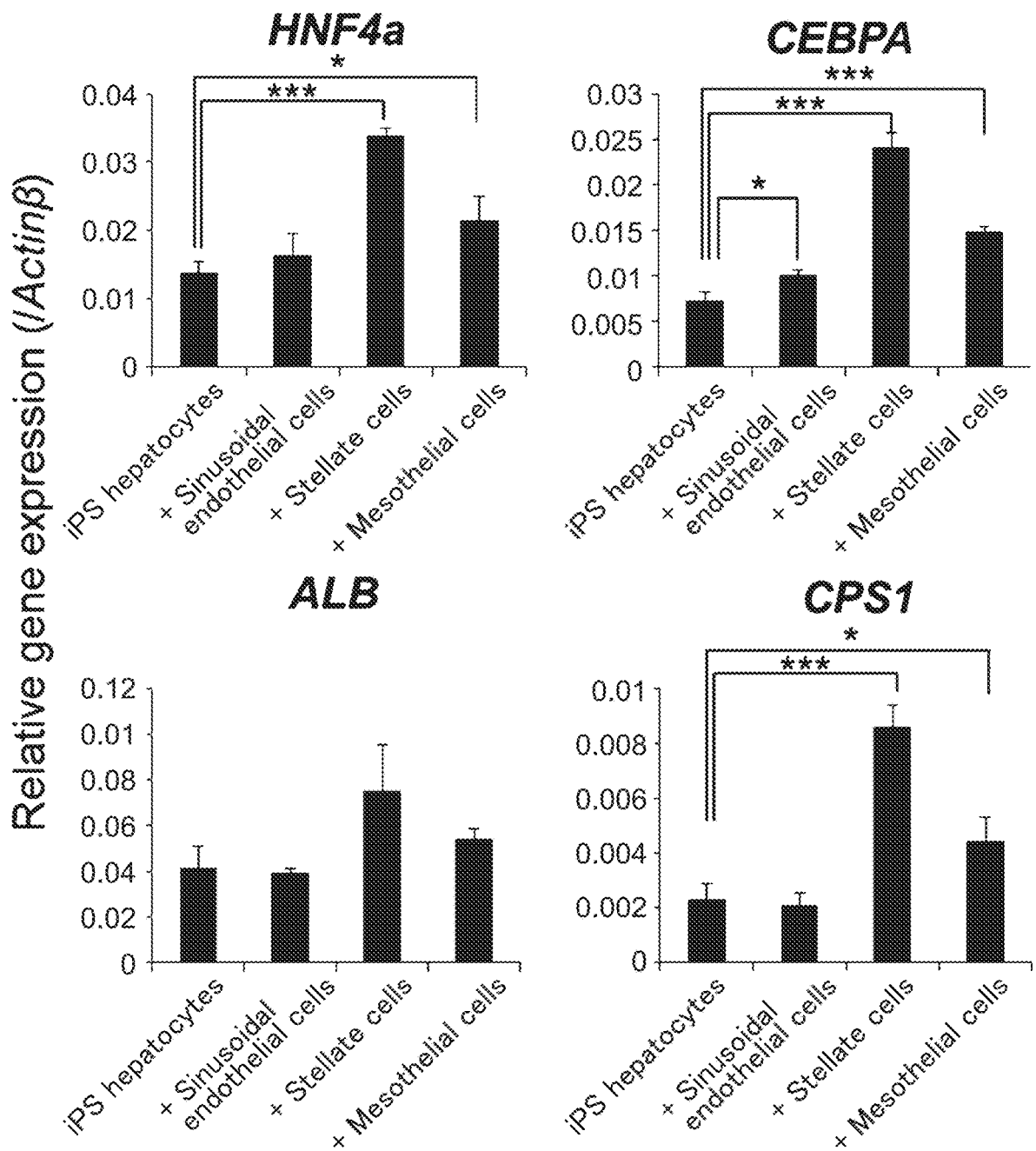
FIG. 33 shows the results of analyzing expression of genes associated with hepatocyte differentiation, when plate culturing human iPS cell-derived liver progenitor cells and mouse non-parenchymal cells. The label "iPS hepatocytes" in the graph represents human iPS cell-derived liver progenitor cells cultured alone. The label "+liver sinusoidal endothelial cells" represents co-culturing of human iPS cell-derived liver progenitor cells and mouse liver sinusoidal endothelial cells. The label "+stellate cells" represents co-culturing of human iPS cell-derived liver progenitor cells and mouse stellate cells. The label "+mesothelial cells" represents co-culturing of human iPS cell-derived liver progenitor cells and mouse mesothelial cells. n=3. mean±SEM. *p<0.05, ***p<0.001.
Figure 34:
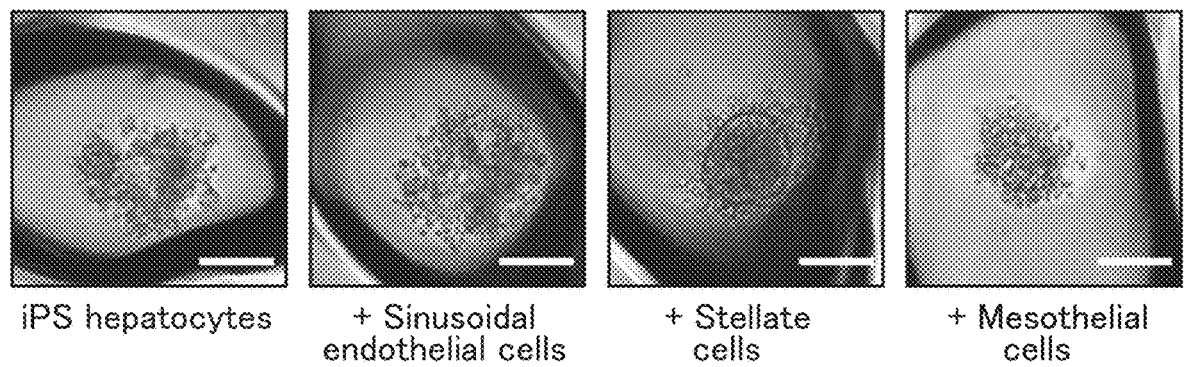
FIG. 34 shows a bright field image on the 2nd day of three-dimensional co-culturing of human iPS cell-derived liver progenitor cells and mouse non-parenchymal cells. The label "iPS hepatocytes" in the graph represents human iPS cell-derived liver progenitor cells cultured alone. The label "+liver sinusoidal endothelial cells" represents co-culturing of human iPS cell-derived liver progenitor cells and mouse liver sinusoidal endothelial cells. The label "+stellate cells" represents co-culturing of human iPS cell-derived liver progenitor cells and mouse stellate cells. The label "+mesothelial cells" represents co-culturing of human iPS cell-derived liver progenitor cells and mouse mesothelial cells. (Scale bar: 50 μm).

Also, a co-culturing system was prepared with the liver sinusoidal endothelial cells, hepatic stellate cells and liver mesothelial cells of Example 9(4)-(6) above, and the human iPS cell-derived liver progenitor cells of Example 1 above, and the effects on liver maturation of each of the cells was verified. The non-parenchymal cells were seeded on collagen gel, and after 2 days of culturing, they were used as feeder cells for co-culturing with iPS cell-derived hepatocyte precursors. In order to evaluate maturation to hepatocytes, gene expression analysis was carried out by quantitative RT-PCR. The results are shown in FIG. 33. The expression levels of HNF4A and CEBPA, which are transcription factors controlling differentiation from liver progenitor cells to hepatocytes, increased with co-culturing with hepatic stellate cells and liver mesothelial cells, compared to culturing of iPS hepatocytes alone. This suggested that hepatic stellate cells and liver mesothelial cells play a role in promoting hepatocyte differentiation. Albumin (ALB), a hepatocyte differentiation marker, was expressed at a level of 1.8-fold in co-culturing with hepatic stellate cells, compared to culturing alone. Expression of the enzyme CPS1 involved in the liver function of ammonia metabolism increased under co-culturing conditions with hepatic stellate cells or liver mesothelial cells, reaching an expression level under co-culturing conditions with hepatic stellate cells that was 3.8-fold compared to culturing alone.

(8) Co-Culturing (Three-Dimensional Culturing (Spheroid Culturing))

Figure 35:
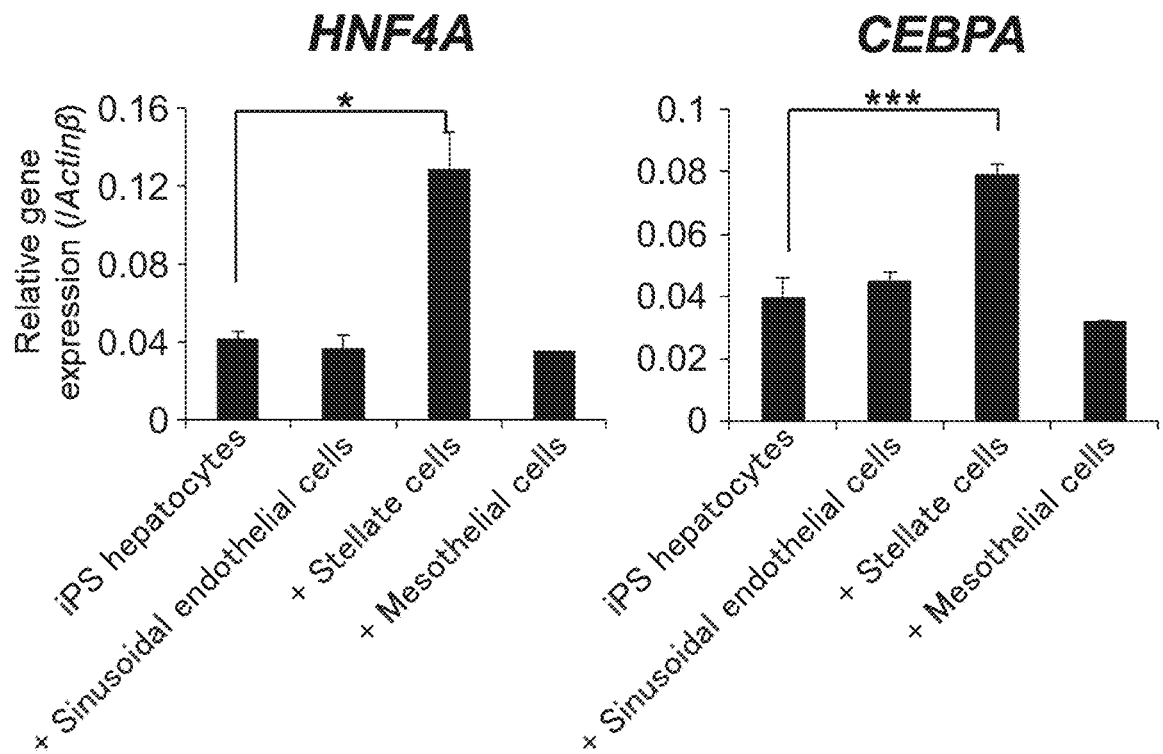
FIG. 35 shows the results of analyzing expression of genes associated with hepatocyte differentiation, for three-dimensional culturing of human iPS cell-derived liver progenitor cells and mouse non-parenchymal cells. The label "iPS hepatocytes" in the graph represents human iPS cell-derived liver progenitor cells cultured alone. The label "+liver sinusoidal endothelial cells" represents co-culturing of human iPS cell-derived liver progenitor cells and mouse liver sinusoidal endothelial cells. The label "+stellate cells" represents co-culturing of human iPS cell-derived liver progenitor cells and mouse stellate cells. The label "+mesothelial cells" represents co-culturing of human iPS cell-derived liver progenitor cells and mouse mesothelial cells. n=3. mean±SEM. ***P<0.005, *P<0.05.
Figure 36:
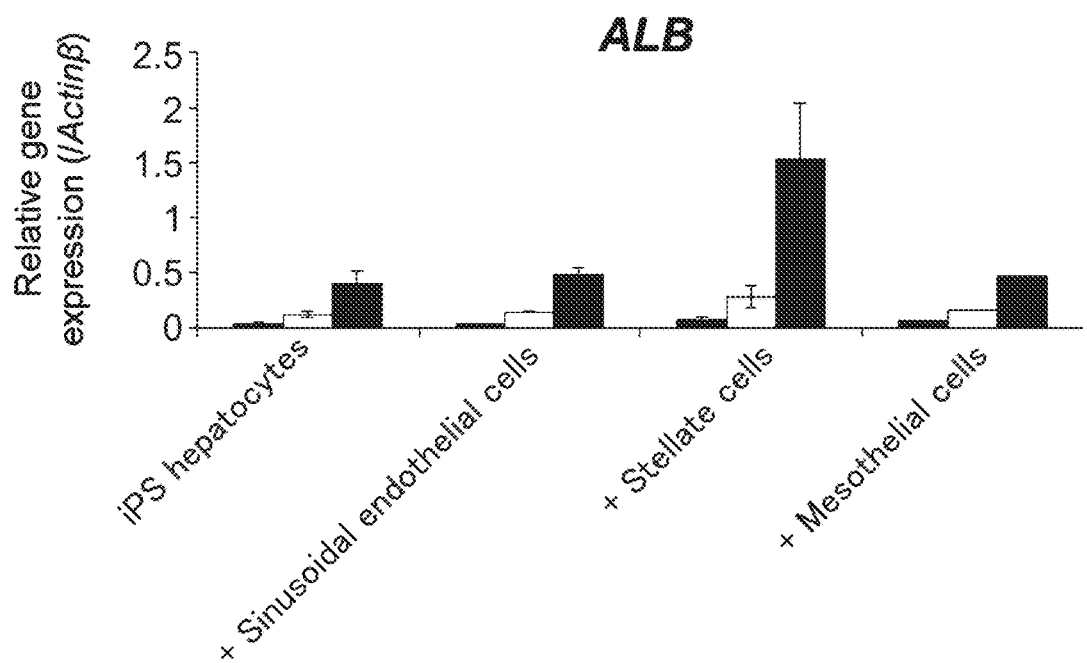
FIG. 36 shows the results of analyzing expression of albumin, for plate culturing and three-dimensional culturing of human iPS cell-derived liver progenitor cells and mouse non-parenchymal cells. The label "iPS hepatocytes" in the graph represents human iPS cell-derived liver progenitor cells cultured alone. The label "+liver sinusoidal endothelial cells" represents co-culturing of human iPS cell-derived liver progenitor cells and mouse liver sinusoidal endothelial cells. The label "+stellate cells" represents co-culturing of human iPS cell-derived liver progenitor cells and mouse stellate cells. The label "+mesothelial cells" represents co-culturing of human iPS cell-derived liver progenitor cells and mouse mesothelial cells. (Left-side bar: 4th day of plate culturing, center bar: 2nd day of three-dimensional culturing, right-side bar: 4th day of three-dimensional culturing)

Culturing was carried out in 96-well-EZsphere (IWAKI) at a density of $5 \times 10^4$ cells/well. The liver sinusoidal endothelial cells ($3 \times 10^4$ cells/well), hepatic stellate cells ($3 \times 10^4$ cells/well) or liver mesothelial cells ($3 \times 10^3$ cells/well) of Example 9(4)-(6) above were simultaneously seeded in the human iPS cell-derived liver progenitor cells of Example 1. The aforementioned differentiation medium was used for exchange of half of the medium on the 2nd day of culturing. Culturing was carried out under conditions of 37° C., 5% $CO_2$, 95% humidity. Spheroid formation was confirmed when three-dimensional culturing was carried out. The results of marker expression analysis are shown in FIG. 35. The expression levels of HNF4A and CEBPA were shown to be particularly increased when co-culturing with hepatic stellate cells. FIG. 36 shows results demonstrating the difference between albumin expression levels with plate culturing and three-dimensional culturing. Upon comparing the 4th day of plate culturing, the 2nd day of three-dimensional culturing and the 4th day of three-dimensional culturing, maturation was found to be efficiently promoted under the three-dimensional culturing conditions.

Figure 37:
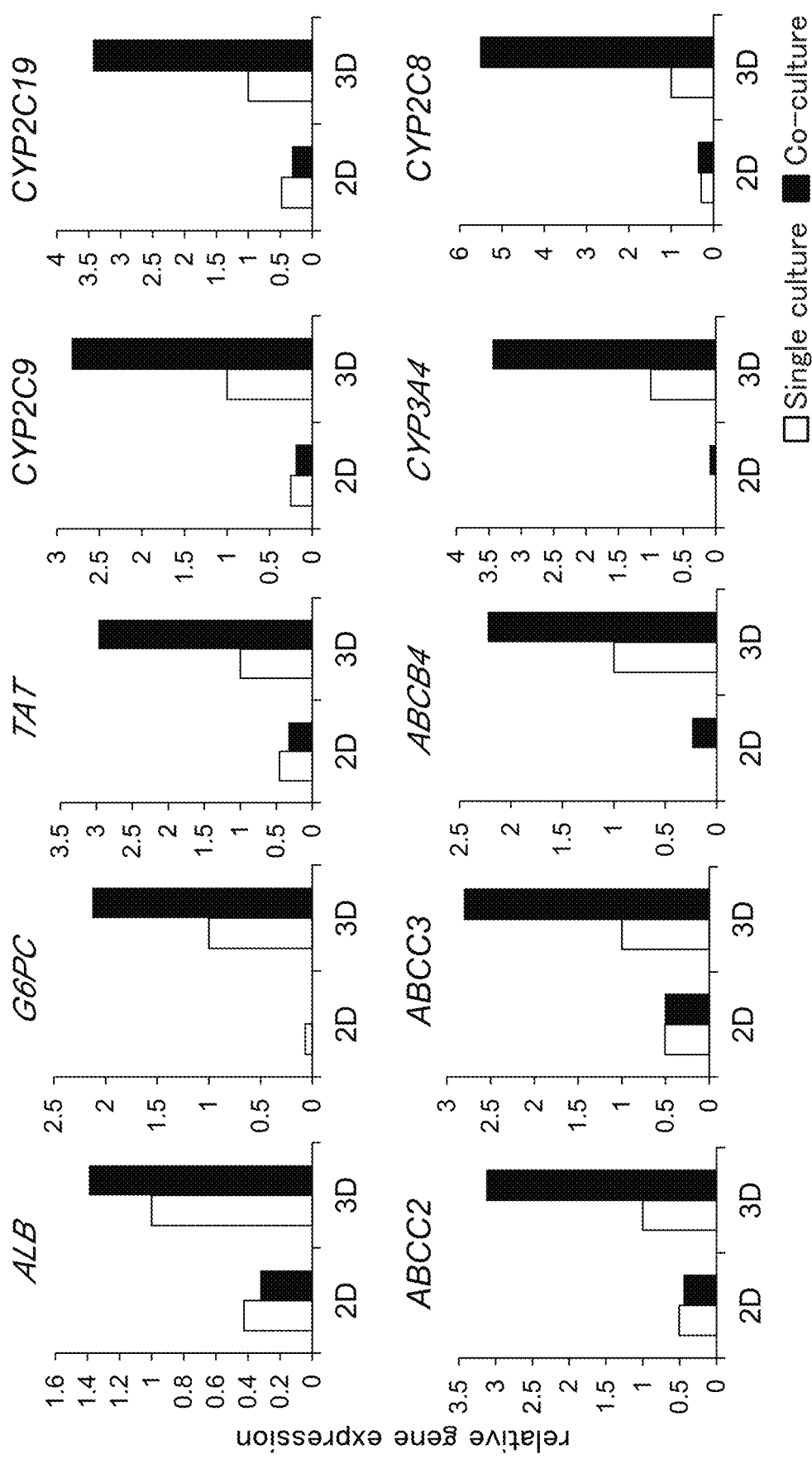
FIG. 37 shows the results of analyzing expression of liver function markers, for plate culturing (two-dimensional culturing) and three-dimensional culturing of human iPS cell-derived liver progenitor cells and mouse non-parenchymal cells. The label "2D" in the graphs represents the results for plate culturing, and the label "3D" in the graphs represents the results for three-dimensional culturing.

FIG. 37 shows the results of analyzing expression of genes associated with hepatocyte differentiation, when plate culturing and three-dimensional culturing the mouse non-parenchymal cells of Example 9(3) above and the human iPS cell-derived liver progenitor cells of Example 1 above. The liver function markers were highly expressed in the three-dimensional culture system.

Example 10

Preparation of Hepatocytes for Human Hepatitis B Disease Model

The human liver progenitor cells prepared in Example 1(1) and the human hepatocytes prepared in Example 2(2) were infected with HBV. The culture supernatants and cells were collected on the 16th day after HBV infection.

Figure 38:
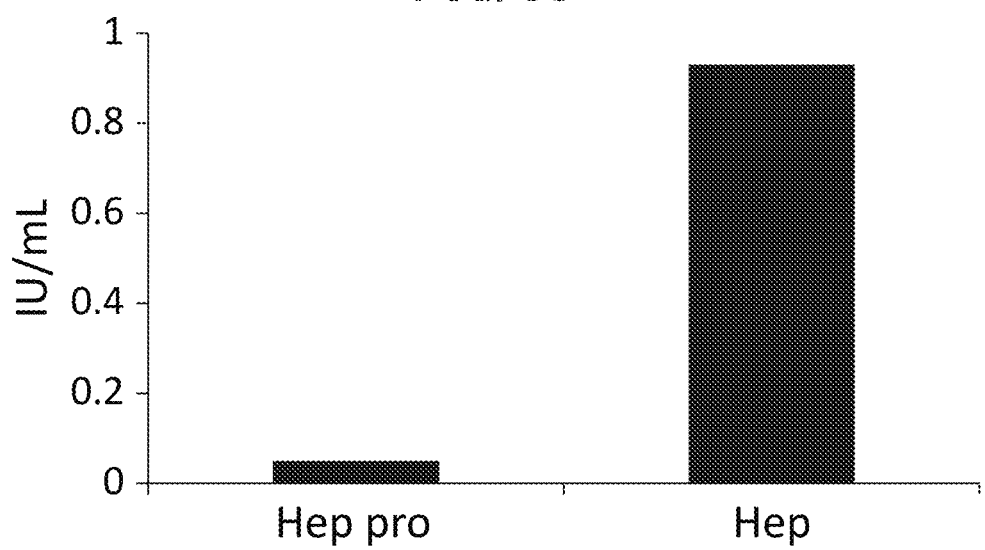
FIG. 38 shows the results of quantifying HBs antigen in culture supernatants of liver progenitor cells (Hep-pro) infected with hepatitis B virus (HBV), and hepatocytes (Hep) induced to differentiate from them.

The quantitation results for HBsAg in the culture supernatants are shown in FIG. 38. HBs antigen was even found in the culture supernatants of the liver progenitor cells and hepatocytes infected with HBV. The HBs antigen level was particularly high in the hepatocytes.

Figure 39:
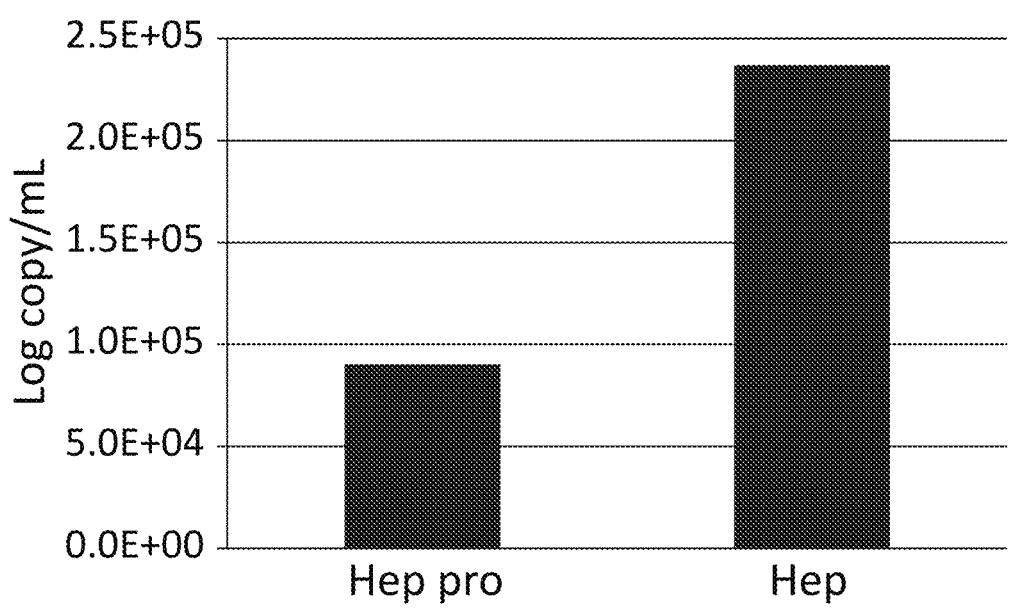
FIG. 39 shows levels of HBs antigen in culture supernatants of liver progenitor cells (Hep-pro) infected with HBV, and hepatocytes (Hep) induced to differentiate from them.

FIG. 39 shows the quantitation results for HBV DNA in the liver progenitor cells and hepatocytes infected with HBV. HBV DNA was found in liver progenitor cells and hepatocytes. It was particularly high in the hepatocytes.

Example 11

Analysis of Production of Substances Necessary for Pathogen Infection

Figure 40:
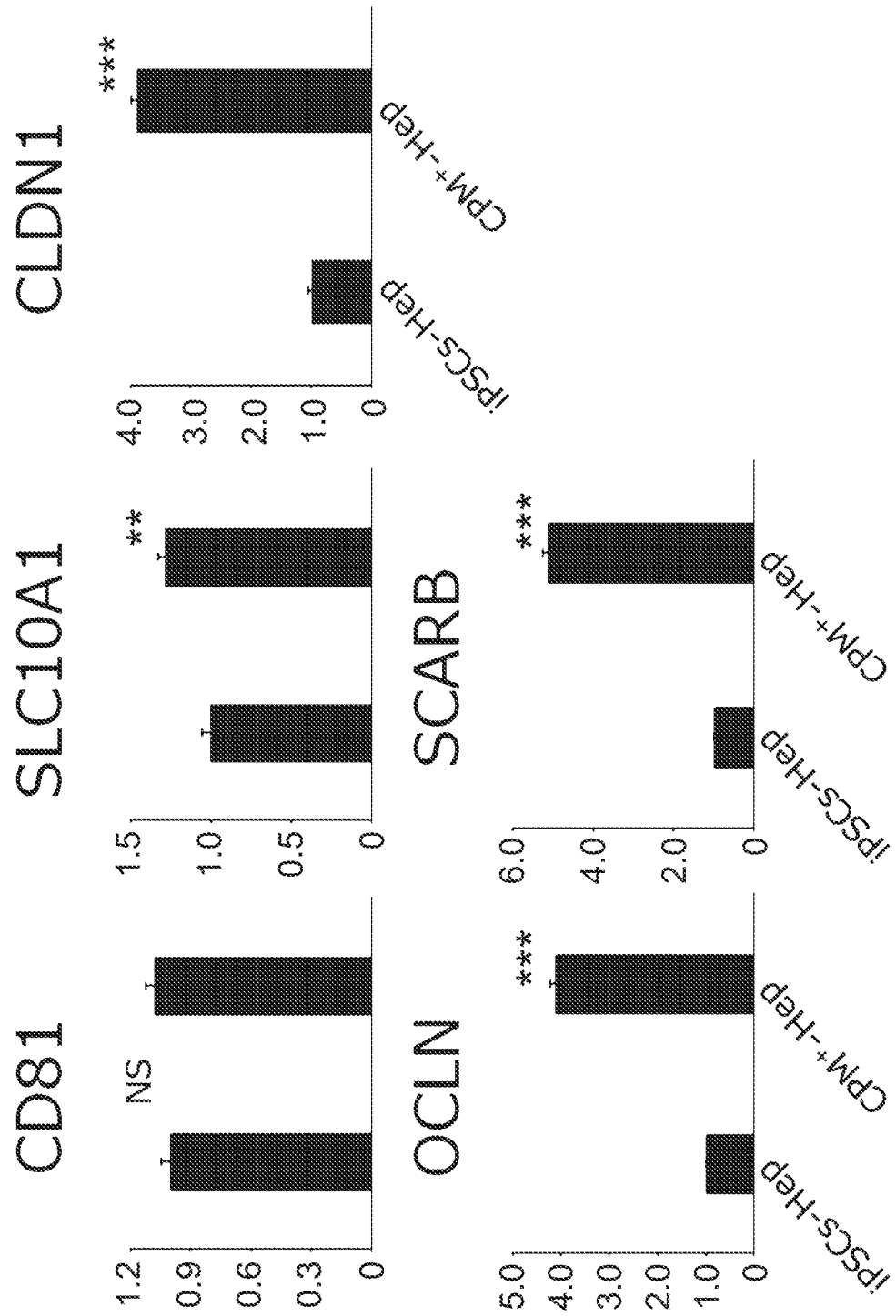
FIG. 40 shows the results of analyzing expression in hepatocytes of molecules that contribute to HBV, HCV and malaria infection. The labels "iPSCs-Hep" in the graphs represent human iPS cell-derived hepatocytes obtained by inducing differentiation of liver progenitor cells, without concentration using CPM-positivity as the marker. The labels "CPM$^+$-Hep" in the graphs represent human iPS cell-derived hepatocytes obtained by inducing differentiation of liver progenitor cells, concentrated using CPM-positivity as the marker. n=6, 3. mean±SEM. **P<0.017*P<0.001, NS: No significant difference.

Quantitative RT-PCR was used to analyze whether or not substances considered necessary for infection of cells with hepatitis B virus, hepatitis C virus and malaria protozoa are produced in the human hepatocytes prepared in Example 2(1) (hereunder referred to as "CPM$^+$-Hep"), and the hepatocytes prepared by inducing differentiation of iPS cells to liver progenitor cells in Example 1(1) and then inducing differentiation by the same procedure as Example 2(1), without a step of separating the liver progenitor cells using CPM-positivity as the marker (hereunder referred to as "iPSCs-Hep"). The results are shown in FIG. 40.

All of the tested hepatocytes expressed a molecule considered necessary for HBV infection (CD81), molecules considered necessary for HCV infection (CD81, CLDN1, OCLN) and molecules considered necessary for HBV infection (CD81, SCARB). The expression levels were higher for CPM$^+$-Hep than for iPSCs-Hep. These results indicate that using hepatocytes of the present invention, which are human iPS cell-derived hepatocytes obtained by inducing differentiation of liver progenitor cells separated by using CPM-positivity as the marker, can be used more suitably for creation of an infectious disease model than human iPS cell-derived hepatocytes obtained by inducing differentiation of liver progenitor cells without separation by using CPM-positivity as the marker.

Example 12

Analysis of Mouse Embryo Hepatocytes (Mouse Liver Progenitor Cells)

Liver was collected from a 12.5-day-old mouse embryo (C57BL/6 mouse). The liver was minced and digested for 15 minutes with Liver Digestion Medium (Life Technologies, California, US). The digested embryonic mouse hepatocytes were passed through a 40 μm cell strainer (BD Bioscience, New Jersey, US), to obtain a single cell suspension. The cells were blocked with Fc block reagent and incubated with PE-labeled anti-CPM antibody and FITC-labeled anti-DLK1 antibody. A PE- and FITC-labeled anti-isotype control was used as a negative control. CPM-positive (CPM$^+$) and CPM-negative (CPM$^-$) cells were isolated using a MoFlo XDP cell sorter (Beckman Coulter, Inc., California, US).

Figure 41:
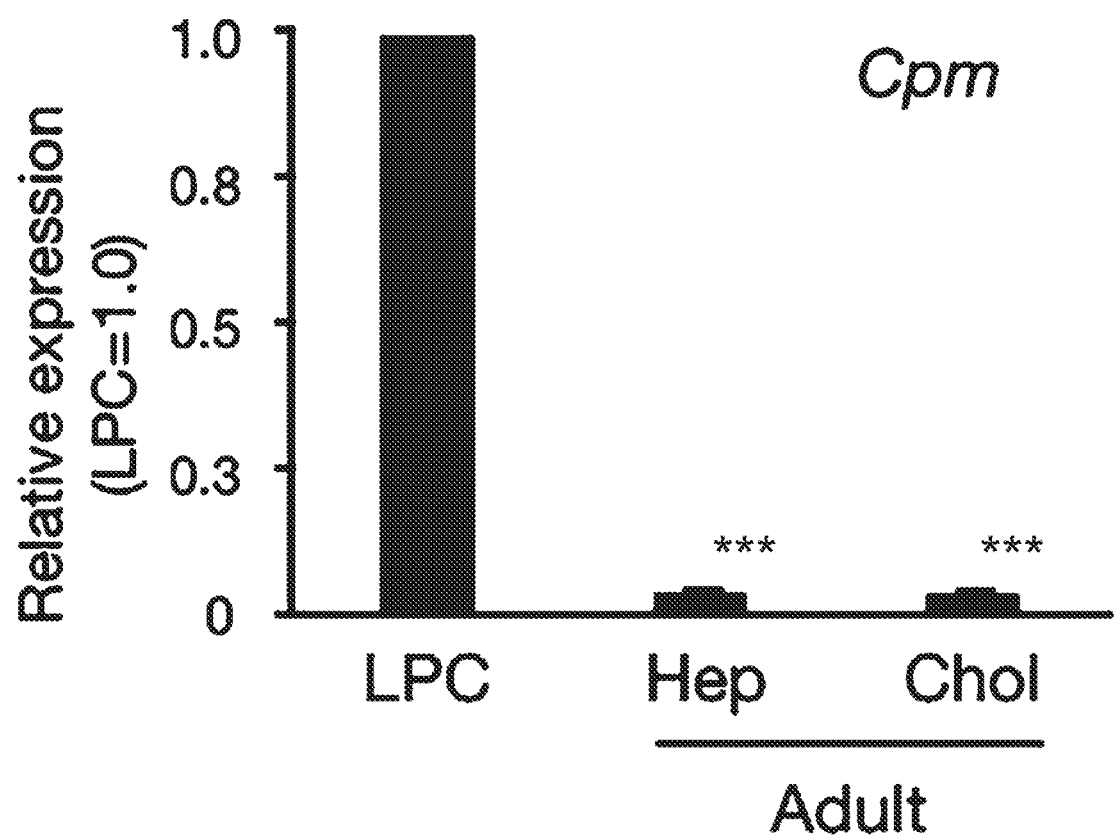
FIG. 41 shows the results of analyzing expression of CPM in mouse liver progenitor cells (LPC), mouse mature hepatocytes (Hep) and mouse cholangiocytes (Chol). The results are expressed as mean±SEM for at least four independent experiments. ***p<0.001.

CPM expression in the collected CPM-positive cells (liver progenitor cells), mouse mature hepatocytes and mouse cholangiocytes was analyzed by quantitative RT-PCR. The results are shown in FIG. 41. For liver progenitor cells, CPM is specific to liver progenitor cells and is virtually unexpressed in hepatocytes and cholangiocytes.

Example 13

Analysis of Mouse Embryo Hepatocytes (Mouse Liver Sinusoidal Endothelial Progenitor Cells)

Liver was collected from a 12.5-day-old mouse embryo (C57BL/6 mouse). The liver was minced and digested for 10 minutes with Liver Digestion Medium (Life Technologies, California, US). The digested embryonic mouse hepatocytes were subjected to hemolysis and passed through a 70 μm cell strainer (BD Bioscience, New Jersey, US). The cells were blocked for 20 minutes with FcR block reagent, and then labeled with FITC-labeled anti-CD31 antibody (BD Biosciences), PE-labeled anti-Flk1 antibody (eBioscience, San Diego, USA), biotin-labeled anti-CD34 antibody (eBioscience) and BV395-labeled anti-CD45 antibody (BD Biosciences), for 30 minutes. After rinsing the cells, they were labeled with streptavidin APC (BD Biosciences) and anti-FITC microbeads (Miltenyi Biotech), for 20 minutes. After concentrating the CD31$^+$ cells with an autoMACS Pro separator (Miltenyi Biotech), a MoFlo XDP cell sorter (Beckman Coulter, Inc, California, US) was used to isolate the CD45$^-$CD31$^+$Flk1$^+$CD34$^{+/-}$ cells.

Figure 42:
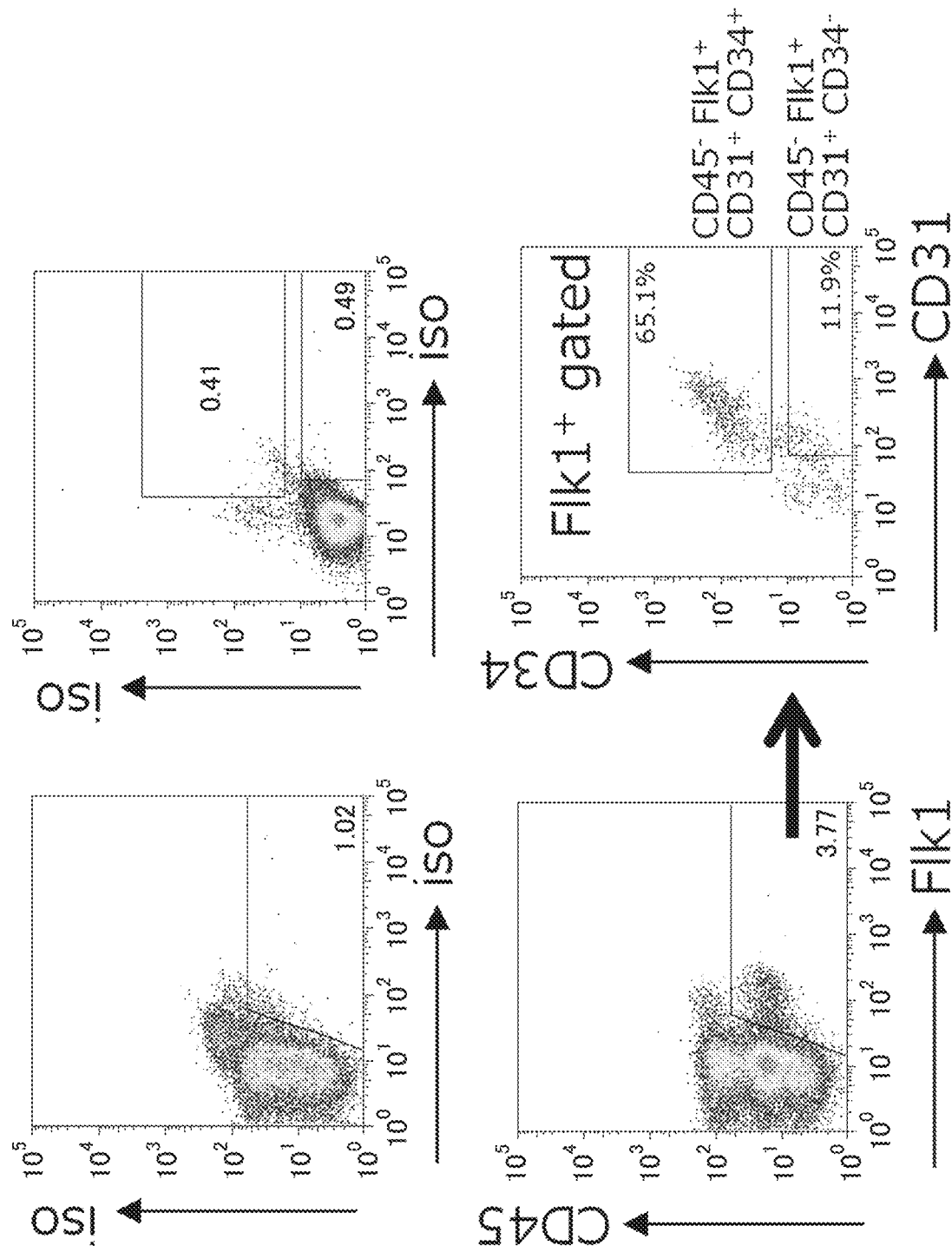
FIG. 42 shows the results of flow cytometry analysis of mouse embryonic liver at an embryonic age of 12.5 days. CD31$^+$CD34$^{+/-}$ cells are present in the CD45$^-$FLK1$^+$ cell fraction (left).
Figure 43:
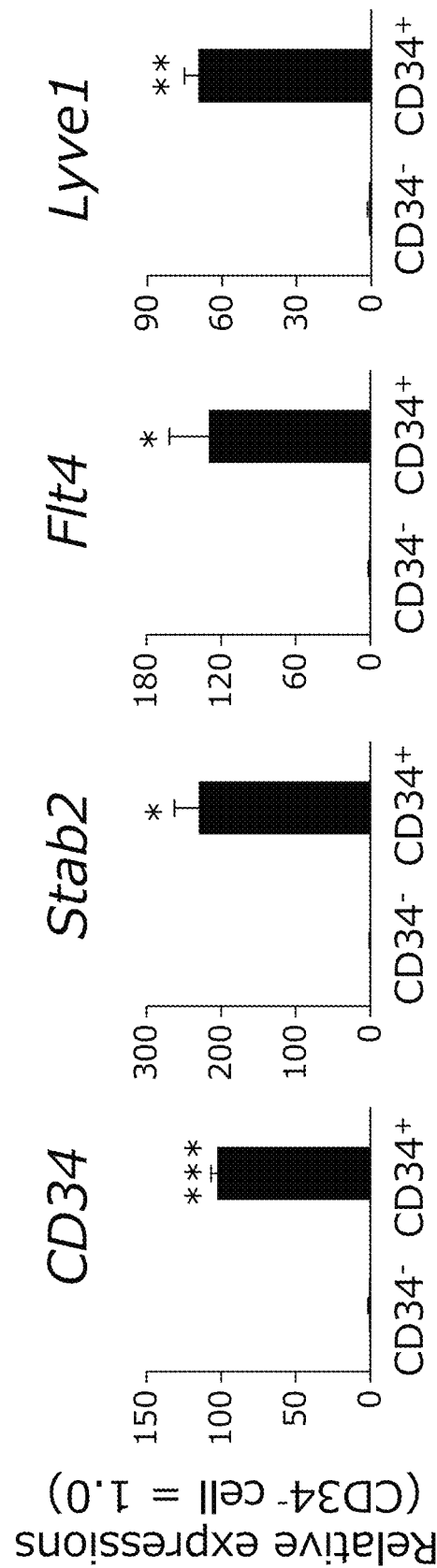
FIG. 43 shows the results of analyzing expression of liver sinusoidal endothelial progenitor cell marker molecules in mouse CD45$^-$FLK1$^+$CD31$^+$CD34$^-$ cells (CD34$^-$) and mouse CD45$^-$FLK1$^+$CD31$^+$CD34$^+$ cells (CD34$^+$). n=3. mean±SEM. *p<0.05, p<0.01, *p<0.001.

It has previously been reported that liver sinusoidal endothelial progenitor cells in mouse embryonic livers express the vascular endothelial cell marker molecules Flk1, CD31 and CD34. By flow cytometry analysis it was demonstrated that 12.5-day-old embryo mouse liver includes $CD45^-Flk1^+CD31^+$ vascular endothelial cells, with a $CD45^-Flk1^+CD31^+CD34^{+/-}$ subpopulation present in the fraction (FIG. 42). These were separated with a cell sorter and subjected to gene expression analysis, and the $CD45^-FLK1^+CD31^+CD34^+$ cells had higher expression of the liver sinusoidal endothelial progenitor cell-specific marker genes Stab2, Flt4 and Lyve1, compared to the $CD45^-FLK1^+CD31^+CD34^-$ cells (FIG. 43).

Figure 44:
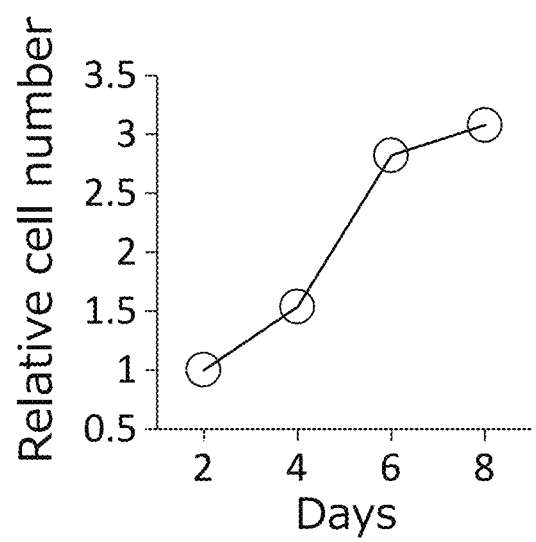
FIG. 44 shows proliferation potency of mouse CD45$^-$FLK1$^+$CD31$^+$CD34$^+$ cells (liver sinusoidal endothelial progenitor cells). n=1.

The $FLK1^+CD31^+CD34^+$ cells separated above were also seeded in a fibronectin-coated plate to 15,000 cells/cm² and cultured in endothelial cell medium. Proliferation was to approximately 3-fold by the 7th day of culturing (FIG. 44). The cell count was calculated using a hemocytometer, after dissociating the cells using 0.05% trypsin/0.5 mM EDTA.

Figure 45:
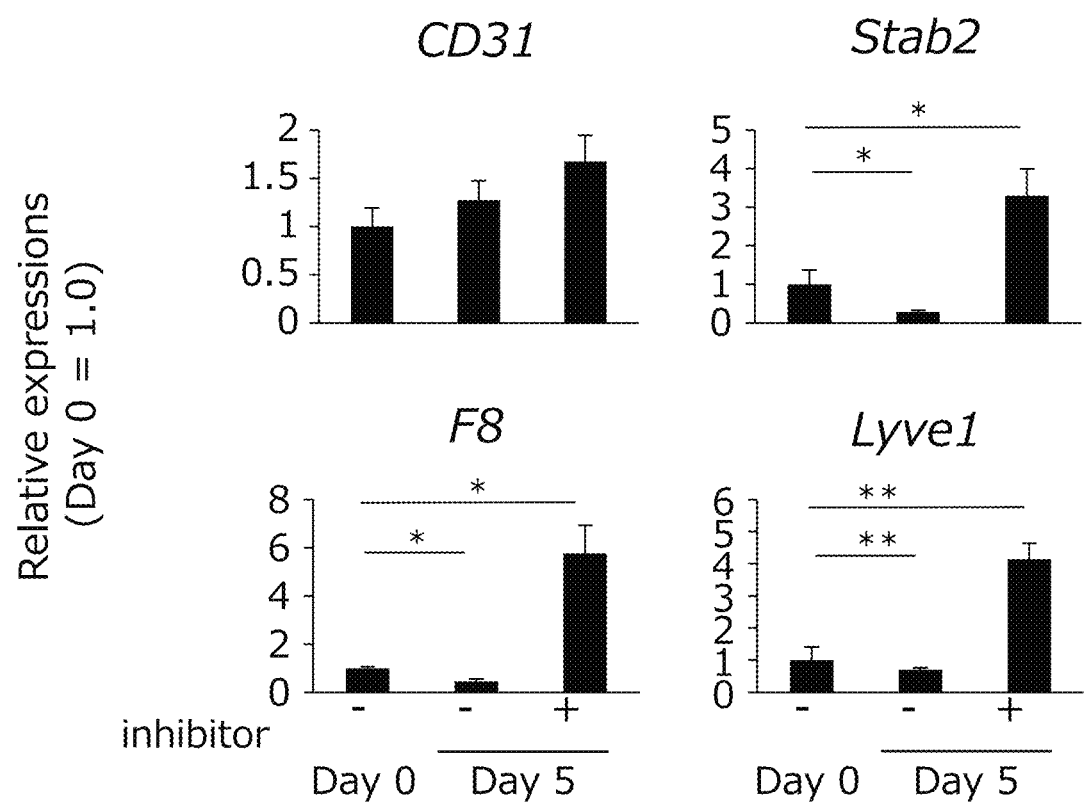
FIG. 45 shows the results of analyzing expression of liver sinusoidal endothelial cell marker molecules in mouse CD45$^-$FLK1$^+$CD31$^+$CD34$^+$ cells 5 days after addition of A83-01. Gene expression level before addition (day 0) was used as the control. n=3. mean±SEM. *p<0.05, **p<0.01.

Furthermore, adding the TGF-β inhibitor A83-01 (Tocris) to the $FLK1^+CD31^+CD34^+$ cell culturing system significantly induced expression of the mature liver sinusoidal endothelial cell marker genes Stab2, F8 and Lyve1 (FIG. 45).

INDUSTRIAL APPLICABILITY

According to the method of the invention it is possible to prepare homogeneous, highly functional hepatocytes, hepatic non-parenchymal cells and their precursor cells in an efficient manner. The obtained hepatocytes can be utilized for innovative drug screening, for example. Also, the obtained hepatocytes, hepatic non-parenchymal cells and their precursor cells can be used for cell therapy, for example. The obtained hepatocytes, hepatic non-parenchymal cells and their precursor cells can also be used to prepare disease models.

The invention claimed is:

1. A method of preparing hepatic stellate cells from induced pluripotent stem (iPS) cells, the method comprising:
    preparing a cell population by inducing differentiation of human iPS cells to mesoderm cells, wherein the cell population comprises hepatic stellate progenitor cells (HSC progenitor);
    separating hepatic stellate progenitor cells (HSC progenitor) from the cell population by sorting out ALCAM positive hepatic stellate progenitor cells; and
    inducing differentiation of hepatic stellate progenitor cells (HSC progenitor) to hepatic stellate cells (HSC) by contacting the HSC progenitor cells with a ROCK inhibitor.

2. The method according to claim 1, wherein the hepatic stellate progenitor cells (HSC progenitor) are hepatic stellate progenitor cells, that have proliferation potency, and have differentiation potency to hepatic stellate cells (HSC).

3. The method according to claim 1, wherein the hepatic stellate cells are positive for the following markers: HGF, NGFR, CYGB, and LRAT.

4. The method according to claim 2, wherein the hepatic stellate cells are positive for the following markers: HGF, NGFR, CYGB, and LRAT.

* * * * *

SEQUENCE LISTING

```
<160> NUMBER OF SEQ ID NOS: 108

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ttctttgcag ctccttcgtt                                              20

<210> SEQ ID NO 2
<211> LENGTH: 19
<212> TYPE: DNA
<213> ORGANISM: Artificial Sequence
<220> FEATURE:
<223> OTHER INFORMATION: primer

<400> SEQUENCE: 2
atggagggga atacagccc                                               19

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
tgggtagctc tctgcctgat                                              20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
tggtaggaac tgatggggat                                              20

<210> SEQ ID NO 5
<211> LENGTH: 20
<212> TYPE: DNA
<213> ORGANISM: Artificial Sequence
```

```
<220> FEATURE:
<223> OTHER INFORMATION: primer

<400> SEQUENCE: 5
tgtccagacg gctacatcaa                                          20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
ccagggatat ccaggacgta                                          20

<210> SEQ ID NO 7
<211> LENGTH: 18
<212> TYPE: DNA
<213> ORGANISM: Artificial Sequence
<220> FEATURE:
<223> OTHER INFORMATION: primer

<400> SEQUENCE: 7
ctctgcctcg gactcctc                                            18

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
ccccggtgtc aatcacata                                           19

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
cctccagcca aaagttcaaa                                          20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
tccaacacgg ggtaaaatgt                                          20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
ctggtgctct atgcaagcct                                          20
```

```
<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
agttgctgcc cattcatcac                                               20

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
tcatgtatag cctggatggg a                                             21

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
gatgagtcca cattgccaaa                                               20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
cccgtttaga accaacaagc                                               20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
gagtcgtgtc cagggactgt                                               20

<210> SEQ ID NO 17
<211> LENGTH: 17
<212> TYPE: DNA
<213> ORGANISM: Artificial Sequence
<220> FEATURE:
<223> OTHER INFORMATION: primer

<400> SEQUENCE: 17
gcacagagcc tcgcctt                                                  17

<210> SEQ ID NO 18
<211> LENGTH: 17
<212> TYPE: DNA
<213> ORGANISM: Artificial Sequence
<220> FEATURE:
<223> OTHER INFORMATION: primer
```

```
<400> SEQUENCE: 18
gttgtcgacg acgagcg                                                17

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
gaaggagaag ctggagcaaa                                             20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
cttctgcttc aggagcttgg                                             20

<210> SEQ ID NO 21
<211> LENGTH: 17
<212> TYPE: DNA
<213> ORGANISM: Artificial Sequence
<220> FEATURE:
<223> OTHER INFORMATION: primer

<400> SEQUENCE: 21
gatggagcca agcccac                                                17

<210> SEQ ID NO 22
<211> LENGTH: 18
<212> TYPE: DNA
<213> ORGANISM: Artificial Sequence
<220> FEATURE:
<223> OTHER INFORMATION: primer

<400> SEQUENCE: 22
ctcaggcagc cactccag                                               18

<210> SEQ ID NO 23
<211> LENGTH: 19
<212> TYPE: DNA
<213> ORGANISM: Artificial Sequence
<220> FEATURE:
<223> OTHER INFORMATION: primer

<400> SEQUENCE: 23
cggggaattc cagtatcac                                              19

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
aggccccaat acacttcaca                                             20

<210> SEQ ID NO 25
```

<210> SEQ ID NO 25
<211> LENGTH: 23
<212> TYPE: DNA
<213> ORGANISM: Artificial Sequence
<220> FEATURE:
<223> OTHER INFORMATION: primer

<400> SEQUENCE: 25
tggagaagtg gcatcagtca aca                                          23

<210> SEQ ID NO 26
<211> LENGTH: 23
<212> TYPE: DNA
<213> ORGANISM: Artificial Sequence
<220> FEATURE:
<223> OTHER INFORMATION: primer

<400> SEQUENCE: 26
tctacaatcc cttgcagtgt gag                                          23

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
cctgtgaaac ctgtgctgac                                              20

<210> SEQ ID NO 28
<211> LENGTH: 21
<212> TYPE: DNA
<213> ORGANISM: Artificial Sequence
<220> FEATURE:
<223> OTHER INFORMATION: primer

<400> SEQUENCE: 28
ccatcgccat ctagtccact g                                            21

<210> SEQ ID NO 29
<211> LENGTH: 16
<212> TYPE: DNA
<213> ORGANISM: Artificial Sequence
<220> FEATURE:
<223> OTHER INFORMATION: primer

<400> SEQUENCE: 29
acttccatct ggacca                                                  16

<210> SEQ ID NO 30
<211> LENGTH: 16
<212> TYPE: DNA
<213> ORGANISM: Artificial Sequence
<220> FEATURE:
<223> OTHER INFORMATION: primer

<400> SEQUENCE: 30
cctttttgct cacaag                                                  16

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31

```
cggctctttc gcttactgtt                                            20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
cctgtatgga ggaggaggaa                                            20

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
gccattcagc aagacaacac                                            20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
aagggttggg cgtaagagat                                            20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
agtttcagca cagcctttgg                                            20

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
agccttgggg tcatatgctt                                            20

<210> SEQ ID NO 37
<211> LENGTH: 23
<212> TYPE: DNA
<213> ORGANISM: Artificial Sequence
<220> FEATURE:
<223> OTHER INFORMATION: primer

<400> SEQUENCE: 37
cttttgcgat tctgctttag tgc                                        23

<210> SEQ ID NO 38
<211> LENGTH: 21
<212> TYPE: DNA
```

<213> ORGANISM: Artificial Sequence
<220> FEATURE:
<223> OTHER INFORMATION: primer

<400> SEQUENCE: 38
taggaggaaa tcttgcgtcc a                                              21

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
cttctgcctc ttgatctccg                                                20

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
aggtacgtca agtcggcaag                                                20

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
cgctgggagt actgtgcaat                                                20

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
ccctgtagcc ttctccttga                                                20

<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
tctatgccaa ctgcgaggac                                                20

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
tcctccatgt gcttgaactg                                                20

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
ctgctgctgt tgctgcttct					20

<210> SEQ ID NO 46
<211> LENGTH: 19
<212> TYPE: DNA
<213> ORGANISM: Artificial Sequence
<220> FEATURE:
<223> OTHER INFORMATION: primer

<400> SEQUENCE: 46
caggctttgc agcactcac					19

<210> SEQ ID NO 47
<211> LENGTH: 19
<212> TYPE: DNA
<213> ORGANISM: Artificial Sequence
<220> FEATURE:
<223> OTHER INFORMATION: primer

<400> SEQUENCE: 47
gaagctgctg gagggagag					19

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
atggacctca gaaccccttt					20

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
tactgcagat atggcacccc					20

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
ccaagactgc tgaagcaaga					20

<210> SEQ ID NO 51
<211> LENGTH: 20
<212> TYPE: DNA
<213> ORGANISM: Artificial Sequence
<220> FEATURE:

```
<223> OTHER INFORMATION: primer

<400> SEQUENCE: 51
gcaggctcaa gaaatgcttc                                               20

<210> SEQ ID NO 52
<211> LENGTH: 20
<212> TYPE: DNA
<213> ORGANISM: Artificial Sequence
<220> FEATURE:
<223> OTHER INFORMATION: primer

<400> SEQUENCE: 52
ggctgctgtc ctcatagctt                                               20

<210> SEQ ID NO 53
<211> LENGTH: 20
<212> TYPE: DNA
<213> ORGANISM: Artificial Sequence
<220> FEATURE:
<223> OTHER INFORMATION: primer

<400> SEQUENCE: 53
agaggagatg tgctggattg                                               20

<210> SEQ ID NO 54
<211> LENGTH: 20
<212> TYPE: DNA
<213> ORGANISM: Artificial Sequence
<220> FEATURE:
<223> OTHER INFORMATION: primer

<400> SEQUENCE: 54
gtggtcagtt tgcagcattc                                               20

<210> SEQ ID NO 55
<211> LENGTH: 21
<212> TYPE: DNA
<213> ORGANISM: Artificial Sequence
<220> FEATURE:
<223> OTHER INFORMATION: primer

<400> SEQUENCE: 55
tgctgatgag tcagctgaaa a                                             21

<210> SEQ ID NO 56
<211> LENGTH: 21
<212> TYPE: DNA
<213> ORGANISM: Artificial Sequence
<220> FEATURE:
<223> OTHER INFORMATION: primer

<400> SEQUENCE: 56
tcagccattt caccataggt t                                             21

<210> SEQ ID NO 57
<211> LENGTH: 20
<212> TYPE: DNA
<213> ORGANISM: Artificial Sequence
<220> FEATURE:
<223> OTHER INFORMATION: primer

<400> SEQUENCE: 57
ggatggaagc gttttttgaag                                              20
```

```
<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
ccacaacaag aacccacagg                                              20

<210> SEQ ID NO 59
<211> LENGTH: 23
<212> TYPE: DNA
<213> ORGANISM: Artificial Sequence
<220> FEATURE:
<223> OTHER INFORMATION: primer

<400> SEQUENCE: 59 tttttgtccta ccataagggc ttt                                          23

<210> SEQ ID NO 60
<211> LENGTH: 20
<212> TYPE: DNA
<213> ORGANISM: Artificial Sequence
<220> FEATURE:
<223> OTHER INFORMATION: primer

<400> SEQUENCE: 60
cacaggctgt tgaccatcat                                              20

<210> SEQ ID NO 61
<211> LENGTH: 20
<212> TYPE: DNA
<213> ORGANISM: Artificial Sequence
<220> FEATURE:
<223> OTHER INFORMATION: primer

<400> SEQUENCE: 61
ttgcttcctg atcaaaatgg                                              20

<210> SEQ ID NO 62
<211> LENGTH: 20
<212> TYPE: DNA
<213> ORGANISM: Artificial Sequence
<220> FEATURE:
<223> OTHER INFORMATION: primer

<400> SEQUENCE: 62
gtctctgtcc cagctccaag                                              20

<210> SEQ ID NO 63
<211> LENGTH: 20
<212> TYPE: DNA
<213> ORGANISM: Artificial Sequence
<220> FEATURE:
<223> OTHER INFORMATION: primer

<400> SEQUENCE: 63
atgaacagtg ctcgggactt                                              20

<210> SEQ ID NO 64
<211> LENGTH: 21
<212> TYPE: DNA
<213> ORGANISM: Artificial Sequence
<220> FEATURE:
<223> OTHER INFORMATION: primer
```

<400> SEQUENCE: 64
tggctatcaa gctttcaaca g                                              21

<210> SEQ ID NO 65
<211> LENGTH: 20
<212> TYPE: DNA
<213> ORGANISM: Artificial Sequence
<220> FEATURE:
<223> OTHER INFORMATION: primer

<400> SEQUENCE: 65
tggacttcca gaacacacca                                                20

<210> SEQ ID NO 66
<211> LENGTH: 18
<212> TYPE: DNA
<213> ORGANISM: Artificial Sequence
<220> FEATURE:
<223> OTHER INFORMATION: primer

<400> SEQUENCE: 66
cccattgagc acgaccac                                                  18

<210> SEQ ID NO 67
<211> LENGTH: 20
<212> TYPE: DNA
<213> ORGANISM: Artificial Sequence
<220> FEATURE:
<223> OTHER INFORMATION: primer

<400> SEQUENCE: 67
cttcgtaaac cagtggcagg                                                20

<210> SEQ ID NO 68
<211> LENGTH: 20
<212> TYPE: DNA
<213> ORGANISM: Artificial Sequence
<220> FEATURE:
<223> OTHER INFORMATION: primer

<400> SEQUENCE: 68
agggcttgtt aatggcagtg                                                20

<210> SEQ ID NO 69
<211> LENGTH: 20
<212> TYPE: DNA
<213> ORGANISM: Artificial Sequence
<220> FEATURE:
<223> OTHER INFORMATION: primer

<400> SEQUENCE: 69
ctcgggactt tatggattgc                                                20

<210> SEQ ID NO 70
<211> LENGTH: 20
<212> TYPE: DNA
<213> ORGANISM: Artificial Sequence
<220> FEATURE:
<223> OTHER INFORMATION: primer

<400> SEQUENCE: 70
cagtgccaac caagttttca                                                20

<210> SEQ ID NO 71
<211> LENGTH: 20

-continued

```
<212> TYPE: DNA
<213> ORGANISM: Artificial Sequence
<220> FEATURE:
<223> OTHER INFORMATION: primer

<400> SEQUENCE: 71
ctgcctacat gagcaaggtg                                           20

<210> SEQ ID NO 72
<211> LENGTH: 20
<212> TYPE: DNA
<213> ORGANISM: Artificial Sequence
<220> FEATURE:
<223> OTHER INFORMATION: primer

<400> SEQUENCE: 72
gggactgcag ctctgtcaac                                           20

<210> SEQ ID NO 73
<211> LENGTH: 20
<212> TYPE: DNA
<213> ORGANISM: Artificial Sequence
<220> FEATURE:
<223> OTHER INFORMATION: primer

<400> SEQUENCE: 73
ctctcaggca tcacctcctc                                           20

<210> SEQ ID NO 74
<211> LENGTH: 18
<212> TYPE: DNA
<213> ORGANISM: Artificial Sequence
<220> FEATURE:
<223> OTHER INFORMATION: primer

<400> SEQUENCE: 74
ggagggtccc gatgatct                                             18

<210> SEQ ID NO 75
<211> LENGTH: 20
<212> TYPE: DNA
<213> ORGANISM: Artificial Sequence
<220> FEATURE:
<223> OTHER INFORMATION: primer

<400> SEQUENCE: 75
acagaagcgt catcaaagca                                           20

<210> SEQ ID NO 76
<211> LENGTH: 21
<212> TYPE: DNA
<213> ORGANISM: Artificial Sequence
<220> FEATURE:
<223> OTHER INFORMATION: primer

<400> SEQUENCE: 76
ccactcagtg tgattccacc t                                         21

<210> SEQ ID NO 77
<211> LENGTH: 17
<212> TYPE: DNA
<213> ORGANISM: Artificial Sequence
<220> FEATURE:
<223> OTHER INFORMATION: primer

<400> SEQUENCE: 77
```

```
gacgctgggc aagctct                                              17

<210> SEQ ID NO 78
<211> LENGTH: 20
<212> TYPE: DNA
<213> ORGANISM: Artificial Sequence
<220> FEATURE:
<223> OTHER INFORMATION: primer

<400> SEQUENCE: 78
gtaatccggg tggtccttct                                           20

<210> SEQ ID NO 79
<211> LENGTH: 21
<212> TYPE: DNA
<213> ORGANISM: Artificial Sequence
<220> FEATURE:
<223> OTHER INFORMATION: primer

<400> SEQUENCE: 79
cctcaaagag ctggagaacc t                                         21

<210> SEQ ID NO 80
<211> LENGTH: 20
<212> TYPE: DNA
<213> ORGANISM: Artificial Sequence
<220> FEATURE:
<223> OTHER INFORMATION: primer

<400> SEQUENCE: 80
gacttgacca tcttcgccac                                           20

<210> SEQ ID NO 81
<211> LENGTH: 20
<212> TYPE: DNA
<213> ORGANISM: Artificial Sequence
<220> FEATURE:
<223> OTHER INFORMATION: primer

<400> SEQUENCE: 81
acagggctct gaacatgcac                                           20

<210> SEQ ID NO 82
<211> LENGTH: 20
<212> TYPE: DNA
<213> ORGANISM: Artificial Sequence
<220> FEATURE:
<223> OTHER INFORMATION: primer

<400> SEQUENCE: 82
ggcattgaaa aactcccgta                                           20

<210> SEQ ID NO 83
<211> LENGTH: 18
<212> TYPE: DNA
<213> ORGANISM: Artificial Sequence
<220> FEATURE:
<223> OTHER INFORMATION: primer

<400> SEQUENCE: 83
cttccacctc cagcagca                                             18

<210> SEQ ID NO 84
<211> LENGTH: 20
<212> TYPE: DNA
<213> ORGANISM: Artificial Sequence
```

```
<220> FEATURE:
<223> OTHER INFORMATION: primer

<400> SEQUENCE: 84
gccatgtacg tgtagggta                                                    20

<210> SEQ ID NO 85
<211> LENGTH: 20
<212> TYPE: DNA
<213> ORGANISM: Artificial Sequence
<220> FEATURE:
<223> OTHER INFORMATION: primer

<400> SEQUENCE: 85
aacctcatcc aggcagtgac                                                   20

<210> SEQ ID NO 86
<211> LENGTH: 20
<212> TYPE: DNA
<213> ORGANISM: Artificial Sequence
<220> FEATURE:
<223> OTHER INFORMATION: primer

<400> SEQUENCE: 86
aagcctgttt cctcgttgtc                                                   20

<210> SEQ ID NO 87
<211> LENGTH: 20
<212> TYPE: DNA
<213> ORGANISM: Artificial Sequence
<220> FEATURE:
<223> OTHER INFORMATION: primer

<400> SEQUENCE: 87
ccattggcat tctctttgaa                                                   20

<210> SEQ ID NO 88
<211> LENGTH: 22
<212> TYPE: DNA
<213> ORGANISM: Artificial Sequence
<220> FEATURE:
<223> OTHER INFORMATION: primer

<400> SEQUENCE: 88
tttggattca tatgccttct gt                                                22

<210> SEQ ID NO 89
<211> LENGTH: 21
<212> TYPE: DNA
<213> ORGANISM: Artificial Sequence
<220> FEATURE:
<223> OTHER INFORMATION: primer

<400> SEQUENCE: 89
ctgaattctc aatgcagggt c                                                 21

<210> SEQ ID NO 90
<211> LENGTH: 21
<212> TYPE: DNA
<213> ORGANISM: Artificial Sequence
<220> FEATURE:
<223> OTHER INFORMATION: primer

<400> SEQUENCE: 90
cccatctcct ttatctcagc c                                                 21
```

<210> SEQ ID NO 91
<211> LENGTH: 18
<212> TYPE: DNA
<213> ORGANISM: Artificial Sequence
<220> FEATURE:
<223> OTHER INFORMATION: primer

<400> SEQUENCE: 91
cctctgtacc ccttcccg                                                   18

<210> SEQ ID NO 92
<211> LENGTH: 20
<212> TYPE: DNA
<213> ORGANISM: Artificial Sequence
<220> FEATURE:
<223> OTHER INFORMATION: primer

<400> SEQUENCE: 92
ggggctccag agtagaggtt                                                 20

<210> SEQ ID NO 93
<211> LENGTH: 20
<212> TYPE: DNA
<213> ORGANISM: Artificial Sequence
<220> FEATURE:
<223> OTHER INFORMATION: primer

<400> SEQUENCE: 93
ttccaggaaa agcatgtgtg                                                 20

<210> SEQ ID NO 94
<211> LENGTH: 20
<212> TYPE: DNA
<213> ORGANISM: Artificial Sequence
<220> FEATURE:
<223> OTHER INFORMATION: primer

<400> SEQUENCE: 94
catttcgctc tcgatgttca                                                 20

<210> SEQ ID NO 95
<211> LENGTH: 20
<212> TYPE: DNA
<213> ORGANISM: Artificial Sequence
<220> FEATURE:
<223> OTHER INFORMATION: primer

<400> SEQUENCE: 95
gagggaccgg agttatgaca                                                 20

<210> SEQ ID NO 96
<211> LENGTH: 20
<212> TYPE: DNA
<213> ORGANISM: Artificial Sequence
<220> FEATURE:
<223> OTHER INFORMATION: primer

<400> SEQUENCE: 96
ttcacattgc acaaggcact                                                 20

<210> SEQ ID NO 97
<211> LENGTH: 21
<212> TYPE: DNA
<213> ORGANISM: Artificial Sequence
<220> FEATURE:
<223> OTHER INFORMATION: primer

```
<400> SEQUENCE: 97
ggaaaagaca ctgaaagggc t                                              21

<210> SEQ ID NO 98
<211> LENGTH: 20
<212> TYPE: DNA
<213> ORGANISM: Artificial Sequence
<220> FEATURE:
<223> OTHER INFORMATION: primer

<400> SEQUENCE: 98
cccaaggcat tttgaaatct                                                20

<210> SEQ ID NO 99
<211> LENGTH: 22
<212> TYPE: DNA
<213> ORGANISM: Artificial Sequence
<220> FEATURE:
<223> OTHER INFORMATION: primer

<400> SEQUENCE: 99
tcgtcttcaa tttcgtcttc tg                                             22

<210> SEQ ID NO 100
<211> LENGTH: 20
<212> TYPE: DNA
<213> ORGANISM: Artificial Sequence
<220> FEATURE:
<223> OTHER INFORMATION: primer

<400> SEQUENCE: 100
ctcccagctc cagatacagg                                                20

<210> SEQ ID NO 101
<211> LENGTH: 20
<212> TYPE: DNA
<213> ORGANISM: Artificial Sequence
<220> FEATURE:
<223> OTHER INFORMATION: primer

<400> SEQUENCE: 101
atcttggtct gtggctgctc                                                20

<210> SEQ ID NO 102
<211> LENGTH: 19
<212> TYPE: DNA
<213> ORGANISM: Artificial Sequence
<220> FEATURE:
<223> OTHER INFORMATION: primer

<400> SEQUENCE: 102
agaaggtgga gcaggtggt                                                 19

<210> SEQ ID NO 103
<211> LENGTH: 20
<212> TYPE: DNA
<213> ORGANISM: Artificial Sequence
<220> FEATURE:
<223> OTHER INFORMATION: primer

<400> SEQUENCE: 103
ggcagatcca gtgcaaagtc                                                20

<210> SEQ ID NO 104
```

```
<211> LENGTH: 18
<212> TYPE: DNA
<213> ORGANISM: Artificial Sequence
<220> FEATURE:
<223> OTHER INFORMATION: primer

<400> SEQUENCE: 104
tcactcccag gaggatgc                                                 18

<210> SEQ ID NO 105
<211> LENGTH: 20
<212> TYPE: DNA
<213> ORGANISM: Artificial Sequence
<220> FEATURE:
<223> OTHER INFORMATION: primer

<400> SEQUENCE: 105
catttatgat gagcagcccc                                               20

<210> SEQ ID NO 106
<211> LENGTH: 20
<212> TYPE: DNA
<213> ORGANISM: Artificial Sequence
<220> FEATURE:
<223> OTHER INFORMATION: primer

<400> SEQUENCE: 106
tagtcagatg ggggtgaagg                                               20

<210> SEQ ID NO 107
<211> LENGTH: 20
<212> TYPE: DNA
<213> ORGANISM: Artificial Sequence
<220> FEATURE:
<223> OTHER INFORMATION: primer

<400> SEQUENCE: 107
catcaagcag caggtcctta                                               20

<210> SEQ ID NO 108
<211> LENGTH: 21
<212> TYPE: DNA
<213> ORGANISM: Artificial Sequence
<220> FEATURE:
<223> OTHER INFORMATION: primer

<400> SEQUENCE: 108
agacggagag atagaagggg a                                             21
```